(12) United States Patent
Yu et al.

(10) Patent No.: US 12,391,700 B2
(45) Date of Patent: Aug. 19, 2025

(54) ORGANIC LIGHT EMITTING DIODE AND ORGANIC LIGHT EMITTING DEVICE INCLUDING THE SAME

(71) Applicants: LG DISPLAY CO., LTD., Seoul (KR); ROHM AND HAAS ELECTRONIC MATERIALS KOREA LTD., Cheonan-si (KR)

(72) Inventors: Young-Jun Yu, Paju-si (KR); Sang-Beom Kim, Paju-si (KR); Do-Han Kim, Paju-si (KR); Jeong-Dae Seo, Paju-si (KR); Chi-Sik Kim, Hwaseong-si (KR); Kyoung-Jin Park, Hwaseong-si (KR); Soo-Yong Lee, Hwaseong-si (KR); Seung-Hoon Yoo, Hwaseong-si (KR)

(73) Assignees: LG DISPLAY CO., LTD., Seoul (KR); DUPONT SPECIALTY MATERIALS KOREA LTD., Cheonan-si (KR)

( * ) Notice: Subject to any disclaimer, the term of this patent is extended or adjusted under 35 U.S.C. 154(b) by 867 days.

(21) Appl. No.: 17/538,294

(22) Filed: Nov. 30, 2021

(65) Prior Publication Data

US 2022/0209131 A1 Jun. 30, 2022

(30) Foreign Application Priority Data

Dec. 29, 2020 (KR) .................. 10-2020-0186055

(51) Int. Cl.
*H01L 51/50* (2006.01)
*C07C 15/28* (2006.01)
(Continued)

(52) U.S. Cl.
CPC ........... *H10K 85/657* (2023.02); *C07C 15/28* (2013.01); *C07D 209/86* (2013.01); *C07D 491/048* (2013.01); *C09K 11/06* (2013.01); *H10K 85/626* (2023.02); *H10K 85/654* (2023.02); *H10K 85/6572* (2023.02); *C07B 2200/05* (2013.01); *C07C 2603/24* (2017.05); *C09K 2211/1007* (2013.01); *C09K 2211/1011* (2013.01); *C09K 2211/1018* (2013.01); *H10K 50/11* (2023.02);
(Continued)

(58) Field of Classification Search
None
See application file for complete search history.

(56) References Cited

U.S. PATENT DOCUMENTS

2017/0117488 A1* 4/2017 Ahn .................... H10K 85/615

FOREIGN PATENT DOCUMENTS

CN 103467450 A 12/2013
CN 110993805 A 4/2020
(Continued)

*Primary Examiner* — Gregory D Clark
(74) *Attorney, Agent, or Firm* — Birch, Stewart, Kolasch & Birch, LLP

(57) ABSTRACT

An organic light emitting diode and an organic light emitting device including the same are discussed. The organic light emitting diode can include a first electrode, a second electrode facing the first electrode, and a first emitting part including a green emitting material layer and positioned between the first and second electrodes. The green emitting material layer can include a first host, a second host and a dopant, wherein at least one of the first host and the second host is deuterated.

19 Claims, 4 Drawing Sheets

(51) Int. Cl.
  *C07D 209/86* (2006.01)
  *C07D 491/048* (2006.01)
  *C09K 11/06* (2006.01)
  *H10K 85/60* (2023.01)
  *H10K 50/11* (2023.01)
  *H10K 50/19* (2023.01)
  *H10K 101/00* (2023.01)
  *H10K 101/10* (2023.01)
  *H10K 102/00* (2023.01)

(52) U.S. Cl.
  CPC ......... *H10K 50/19* (2023.02); *H10K 2101/10* (2023.02); *H10K 2101/90* (2023.02); *H10K 2102/351* (2023.02)

(56) References Cited

FOREIGN PATENT DOCUMENTS

| | | | | |
|---|---|---|---|---|
| CN | 111403614 A | 7/2020 | | |
| CN | 111509132 A | 8/2020 | | |
| EP | 3305871 A1 * | 4/2018 | ............. | H01L 51/00 |
| JP | 2009-277790 A | 11/2009 | | |
| KR | 10-2015-0116776 A | 10/2015 | | |
| KR | 10-2020-0081983 A | 7/2020 | | |
| KR | 10-2022-0009351 A | 1/2022 | | |
| WO | WO 2020/080417 A1 | 4/2020 | | |

\* cited by examiner

ORGANIC LIGHT EMITTING DIODE AND ORGANIC LIGHT EMITTING DEVICE INCLUDING THE SAME

CROSS-REFERENCE TO RELATED APPLICATIONS

The present application claims the priority benefit of Korean Patent Application No. 10-2020-0186055 filed in the Republic of Korea on Dec. 29, 2020, the entire contents of which are hereby incorporated by reference into the present application.

BACKGROUND

Field of Technology

The present disclosure relates to an organic light emitting diode (OLED) and an organic light emitting device, and more specifically, to an organic light emitting diode (OLED) having an improved lifespan and an organic light emitting device including the same.

Background Discussion

As requests for a flat panel display device having a small occupied area have been increased, an organic light emitting display device including an OLED has been the subject of recent research and development.

The OLED emits light by injecting electrons from a cathode as an electron injection electrode and holes from an anode as a hole injection electrode into an emitting material layer (EML), combining the electrons with the holes, generating an exciton, and transforming the exciton from an excited state to a ground state. A flexible substrate, for example, a plastic substrate, can be used as a base substrate where elements are formed. In addition, the organic light emitting display device can be operated at a voltage (e.g., 10V or below) lower than a voltage required to operate other display devices. Moreover, the organic light emitting display device has advantages in the power consumption and the color sense.

The OLED includes a first electrode as an anode over a substrate, a second electrode, which is spaced apart from and faces the first electrode, and an organic emitting layer therebetween.

The materials in the organic emitting layer have been studied and researched, but there can be still a limitation in the lifespan of the OLED.

SUMMARY OF THE DISCLOSURE

The present disclosure is directed to an OLED and an organic light emitting device including the OLED that substantially obviate one or more of the problems associated with the limitations and disadvantages of the related conventional art.

Additional features and advantages of the present disclosure are set forth in the description which follows, and will be apparent from the description, or evident by practice of the present disclosure. The objectives and other advantages of the present disclosure are realized and attained by the features described herein as well as in the appended drawings.

To achieve these and other advantages in accordance with the purpose of the embodiments of the present disclosure, as described herein, an aspect of the present disclosure is an organic light emitting diode comprising a first electrode; a second electrode facing the first electrode; and a first emitting part including a green emitting material layer and positioned between the first and second electrodes, the green emitting material layer including a first host, a second host and a dopant, wherein the first host is represented by Formula 1-1:

[Formula 1-1]

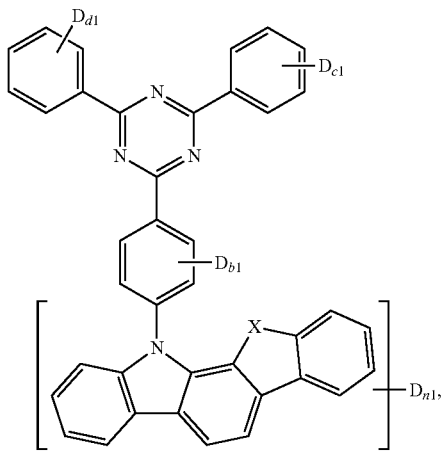

wherein X is oxygen or sulfur, a1 is an integer of 0 to 10, wherein b1 is an integer of 0 to 4, and each of c1 and d1 is independently an integer of 0 to 5, wherein the second host is represented by Formula 2-1:

[Formula 2-1]

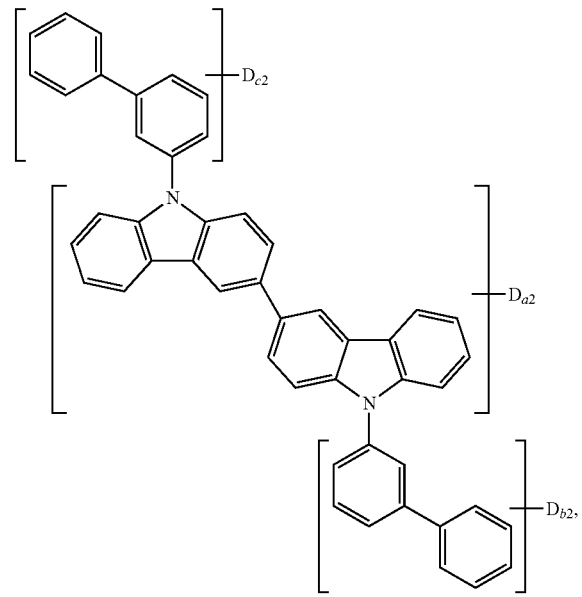

wherein a2 is an integer of 0 to 14, and each of b2 and c2 is independently an integer of 0 to 9, and wherein at least one of a1, a2, b1, b2, c1, c2 and d1 is a positive integer.

Another aspect of the present disclosure is an organic light emitting device comprising a substrate; and the above organic light emitting diode positioned on the substrate.

It is to be understood that both the foregoing general description and the following detailed description are exemplary and explanatory and are intended to further explain the present disclosure as claimed.

BRIEF DESCRIPTION OF THE DRAWINGS

The accompanying drawings, which are included to provide a further understanding of the present disclosure and are incorporated in and constitute a part of this specification, illustrate embodiments of the present disclosure and together with the description serve to explain the principles of the present disclosure.

DETAILED DESCRIPTION OF THE EMBODIMENTS

Reference will now be made in detail to some of the examples and preferred embodiments, which are illustrated in the accompanying drawings.

In the present disclosure, an aryl group, an arylene group, a heteroaryl group and a heteroarylene group can be unsubstituted or substituted with alkyl and/or aryl without specific definition.

Figure 1:
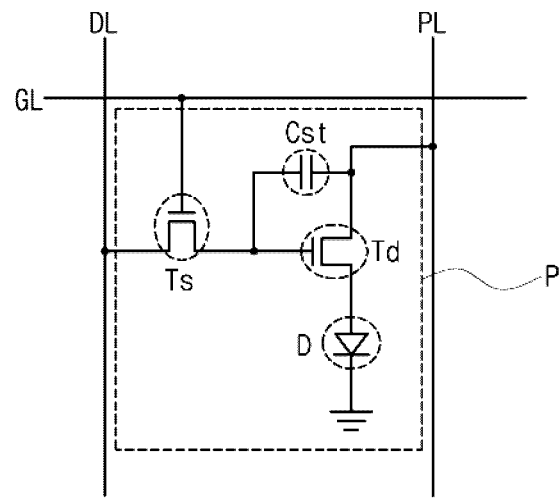
FIG. 1 is a schematic circuit diagram illustrating an organic light emitting display device of the present disclosure.

FIG. 1 is a schematic circuit diagram illustrating an organic light emitting display device of the present disclosure. All the components of each organic light emitting display device according to all embodiments of the present disclosure are operatively coupled and configured.

As illustrated in FIG. 1, a gate line GL and a data line DL, which cross each other to define a pixel region (pixel) P, and a power line PL are formed in an organic light emitting display device. A switching thin film transistor (TFT) Ts, a driving TFT Td, a storage capacitor Cst and an OLED D are formed in the pixel region P. The pixel region P can include a red pixel region, a green pixel region and a blue pixel region. In addition, the pixel region P can further include a white pixel region.

The switching thin film transistor Ts is connected to the gate line GL and the data line DL, and the driving thin film transistor Td and the storage capacitor Cst are connected between the switching thin film transistor Ts and the power line PL. The OLED D is connected to the driving thin film transistor Td. When the switching thin film transistor Ts is turned on by the gate signal applied through the gate line GL, the data signal applied through the data line DL is applied to a gate electrode of the driving thin film transistor Td and one electrode of the storage capacitor Cst through the switching thin film transistor Ts.

The driving thin film transistor Td is turned on by the data signal applied into the gate electrode so that a current proportional to the data signal is supplied from the power line PL to the OLED D through the driving thin film transistor Td. The OLED D emits light having a luminance proportional to the current flowing through the driving thin film transistor Td. In this case, the storage capacitor Cst is charged with a voltage proportional to the data signal so that the voltage of the gate electrode in the driving thin film transistor Td is kept constant during one frame. Therefore, the organic light emitting display device can display a desired image.

Figure 2:
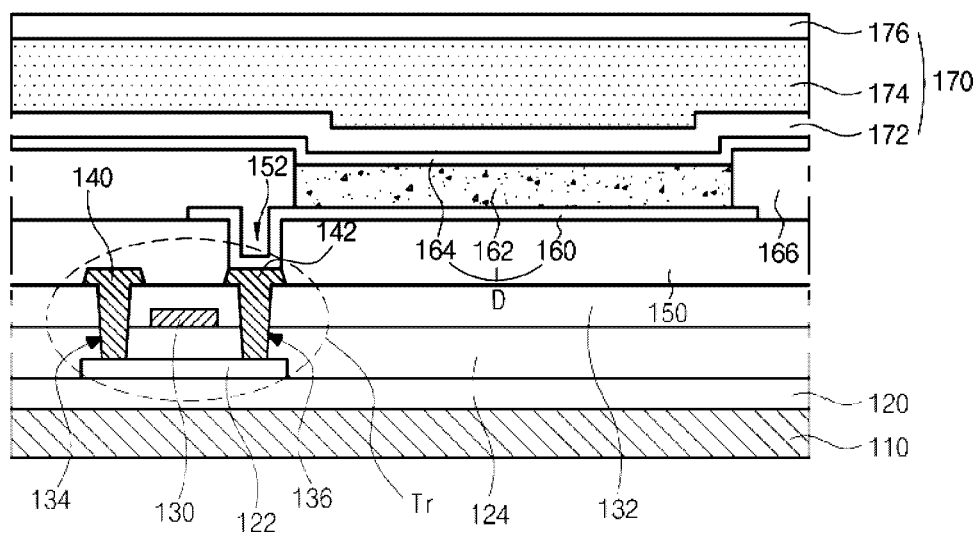
FIG. 2 is a schematic cross-sectional view illustrating an organic light emitting display device according to a first embodiment of the present disclosure.

FIG. 2 is a schematic cross-sectional view illustrating an organic light emitting display device according to a first embodiment of the present disclosure.

As illustrated in FIG. 2, the organic light emitting display device 100 includes a substrate 110, a TFT Tr and an OLED D connected to the TFT Tr. For example, the organic light emitting display device 100 can include a red pixel region, a green pixel region and a blue pixel region, and the OLED D can be formed in each of the red, green and blue pixel regions. Namely, the OLEDs D emitting red light, green light and blue light can be provided in the red, green and blue pixel regions, respectively.

The substrate 110 can be a glass substrate or a flexible substrate. For example, the flexible substrate can be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 120 is formed on the substrate, and the TFT Tr is formed on the buffer layer 120. The buffer layer 120 can be omitted.

A semiconductor layer 122 is formed on the buffer layer 120. The semiconductor layer 122 can include an oxide semiconductor material or polycrystalline silicon.

When the semiconductor layer 122 includes the oxide semiconductor material, a light-shielding pattern can be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities can be doped into both sides of the semiconductor layer 122.

A gate insulating layer 124 is formed on the semiconductor layer 122. The gate insulating layer 124 can be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 2, the gate insulating layer 124 is formed on an entire surface of the substrate 110. Alternatively, the gate insulating layer 124 can be patterned to have the same shape as the gate electrode 130.

An interlayer insulating layer 132, which is formed of an insulating material, is formed on the gate electrode 130. The interlayer insulating layer 132 can be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element. Namely, the TFT Tr can correspond to the driving TFT Td (of FIG. 1).

In the TFT Tr, the gate electrode 130, the source electrode 140, and the drain electrode 142 are positioned over the semiconductor layer 122. Namely, the TFT Tr has a coplanar structure.

Alternatively, in the TFT Tr, the gate electrode can be positioned under the semiconductor layer, and the source and drain electrodes can be positioned over the semiconductor layer such that the TFT Tr can have an inverted staggered structure. In this instance, the semiconductor layer can include amorphous silicon.

The gate line and the data line cross each other to define the pixel region, and the switching TFT is formed to be connected to the gate and data lines. The switching TFT is connected to the TFT Tr as the driving element.

In addition, the power line, which can be formed to be parallel to and spaced apart from one of the gate and data lines, and the storage capacitor for maintaining the voltage of the gate electrode of the TFT Tr in one frame can be further formed.

A planarization layer 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel region and on the planarization layer 150. The first electrode 160 can be an anode and can be formed of a conductive material having a relatively high work function. For example, the first electrode 160 can be formed of a transparent conductive material such as indium-tin-oxide (ITO) or indium-zinc-oxide (IZO).

When the organic light emitting display device 100 is operated in a bottom-emission type, the first electrode 160 can have a single-layered structure of the transparent conductive material layer. When the organic light emitting display device 100 is operated in a top-emission type, a reflection electrode or a reflection layer can be formed under the first electrode 160. For example, the reflection electrode or the reflection layer can be formed of silver (Ag) or aluminum-palladium-copper (APC) alloy. In this instance, the first electrode 160 can have a triple-layered structure of ITO/Ag/ITO or ITO/APC/ITO.

A bank layer 166 is formed on the planarization layer 150 to cover an edge of the first electrode 160. Namely, the bank layer 166 is positioned at a boundary of the pixel region and exposes a center of the first electrode 160 in the pixel region.

An organic emitting layer 162 is formed on the first electrode 160. The organic emitting layer 162 includes a single emitting part including an emitting material layer (EML). Alternatively, the organic emitting layer 162 includes a plurality of emitting parts, e.g., at least two emitting parts, each including the EML. In addition, the organic emitting layer 162 can further include a charge generation layer between adjacent emitting parts.

Each emitting part can further include at least one of a hole injection layer (HIL), a hole transporting layer (HTL), an electron blocking layer (EBL), a hole blocking layer (HBL), an electron transporting layer (ETL) and an electron injection layer (EIL) such that each emitting part has a multi-layered structure.

The organic emitting layer 162 is separated in each of the red, green and blue pixel regions. As illustrated below, in the OLED D in the green pixel region, the EML includes a first host including a fused-hetero ring moiety and a second host including a biscarbazole moiety, and at least one of the fused-hetero ring moiety and the biscarbazole moiety is deuterated. As a result, the lifespan of the OLED D and the organic light emitting display device 100 are improved.

The second electrode 164 is formed over the substrate 110 where the organic emitting layer 162 is formed. The second electrode 164 covers an entire surface of the display area and can be formed of a conductive material having a relatively low work function to serve as a cathode. For example, the second electrode 164 can be formed of aluminum (Al), magnesium (Mg), silver (Ag) or their alloy, e.g., Al—Mg alloy (AlMg) or Ag—Mg alloy (MgAg). In the top-emission type organic light emitting display device 100, the second electrode 164 can have a thin profile (small thickness) to provide a light transmittance property (or a semi-transmittance property).

The first electrode 160, the organic emitting layer 162 and the second electrode 164 constitute the OLED D.

An encapsulation film 170 is formed on the second electrode 164 to prevent penetration of moisture into the OLED D. The encapsulation film 170 includes a first inorganic insulating layer 172, an organic insulating layer 174 and a second inorganic insulating layer 176 sequentially stacked, but it is not limited thereto. The encapsulation film 170 can be omitted.

The organic light emitting display device 100 can further include a polarization plate for reducing an ambient light reflection. For example, the polarization plate can be a circular polarization plate. In the bottom-emission type organic light emitting display device 100, the polarization plate can be disposed under the substrate 110. In the top-emission type organic light emitting display device 100, the polarization plate can be disposed on or over the encapsulation film 170.

In addition, in the top-emission type organic light emitting display device 100, a cover window can be attached to the encapsulation film 170 or the polarization plate. In this instance, the substrate 110 and the cover window have a flexible property such that a flexible organic light emitting display device can be provided.

Figure 3:
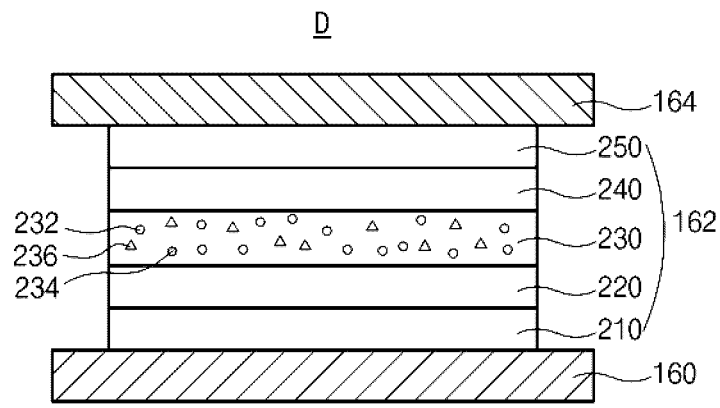
FIG. 3 is a schematic cross-sectional view illustrating an OLED according to a second embodiment.

FIG. 3 is a schematic cross-sectional view illustrating an OLED according to a second embodiment.

As shown in FIG. 3, the OLED D includes the first and second electrodes 160 and 164 facing each other and the organic emitting layer 162 between the first and second electrodes 160 and 164. The organic emitting layer 162 includes a green EML 230.

The organic light emitting display device 100 (of FIG. 2) can include a red pixel region, a green pixel region and a blue pixel region, and the OLED D can be positioned in the green pixel region.

The first electrode 160 is an anode injecting a hole, and the second electrode 164 is a cathode injecting an electron. One of the first and second electrodes 160 and 164 is a reflection electrode, and the other one of the first and second electrodes 160 and 164 is a transparent electrode (or a semi-transparent electrode).

For example, the first electrode 160 can include a transparent conductive material, e.g., ITO or IZO, and the second electrode 164 can be formed of Al, Mg, Ag, AlMg or MgAg.

The organic emitting layer 162 can further include at least one of an HTL 220 under the green EML 230 and an ETL 240 over the green EML 230. Namely, the HTL 220 is disposed between the green EML 230 and the first electrode 160, and the ETL 240 is disposed between the green EML 230 and the second electrode 164.

In addition, the organic emitting layer 162 can further include an HIL 210 under the HTL 220 and an EIL 250 over the ETL 240.

The organic emitting layer 162 can further include at least one of an EBL between the HTL 220 and the green EML 230 and an HBL between the green EML 230 and the ETL 240.

In the OLED D, the green EML 230 constitutes an emitting part, or the green EML 230 with at least one of the HIL 210, the HTL 220, the EBL, the HBL, the ETL 240 and the EIL 250 constitute the emitting part.

The green EML 230 includes a first host 232 as a first compound and a second host 234 as a second compound. The green EML 230 can have a thickness of 50 to 600 Å, preferably 200 to 400 Å. In the green EML 230, a weight % ratio of the first host 232 to the second host 234 can be 1:9 to 9:1, preferably 2:8 to 8:2, and more preferably 3:7 to 7:3. In an embodiment, in the green EML 230, the weight % of the first host 232 can be smaller than that of the second host 234. For example, in the green EML 230, the weight % ratio of the first host 232 to the second host 234 can be 2:8 to 4:6, preferably 3:7.

The first compound being the first host 232 in the green EML 230 includes a fused-hetero ring moiety (e.g., a fused-heterocyclic moiety), a diphenyltriazine moiety and a phenylene linker linking the fused-hetero ring moiety and the diphenyltriazine moiety. In addition, the second compound being the second host 234 in the green EML 230 includes a biscarbazole moiety and a biphenyl moiety linked (connected or combined) to both sides of the biscarbazole moiety. The first host 232 can be an N-type host, and the second host 234 can be a P-type host.

At least one of the first and second hosts 232 and 234 is substituted with deuterium atom. In other words, at least one of the first and second hosts 232 and 234 is deuterated. When at least one of hydrogen atoms in the first host 232 is substituted with deuterium atom (e.g., partially deuterated or wholly deuterated), the second host 234 is not substituted with deuterium atom (e.g., non-deuterated), or at least one of hydrogen atoms in the second host 234 is substituted with deuterium atom (e.g., partially deuterated or wholly deuterated). Alternatively, when the second host 234 is partially or wholly deuterated, the first host 232 is non-deuterated, partially deuterated or wholly deuterated.

The first host 232 (i.e., the first compound) is represented by Formula 1-1.

[Formula 1-1]

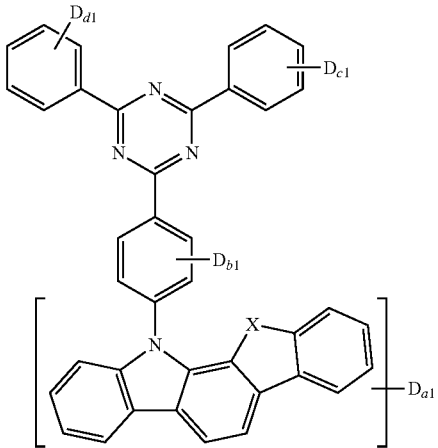

In Formula 1-1, X is oxygen (O) or sulfur (S). In Formula 1-1, a1 is an integer of 0 to 10, b1 is an integer of 0 to 4, and each of c1 and d1 is independently an integer of 0 to 5. (In Formula 1-1, D denotes deuterium atom, and each of a1, b1, c1 and d1 denotes a number of deuterium atom.)

The second host 234 (i.e., the second compound) is represented by Formula 2-1.

[Formula 2-1]

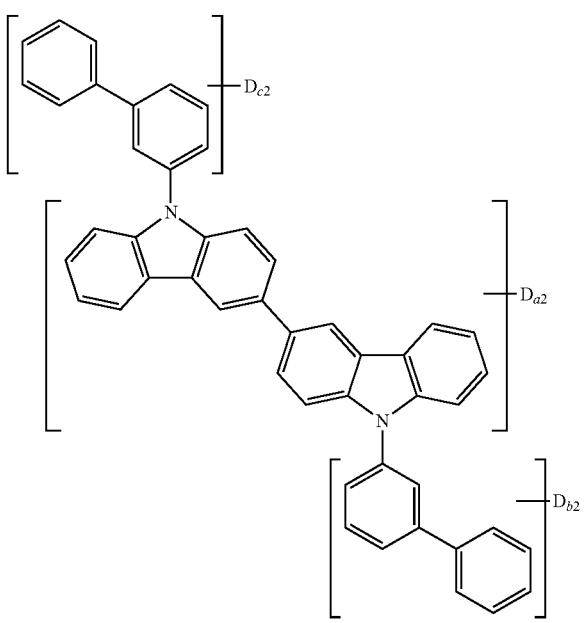

In Formula 2-1, a2 is an integer of 0 to 14, b2 is an integer of 0 to 9, and c2 is an integer of 0 to 9. (In Formula 2-1, D denotes deuterium atom, and each of a2, b2, and c2 denotes a number of deuterium atom.)

In this instance, at least one of a1, a2, b1, b2, c1, c2 and d1 is a positive integer.

For example, at least one of the fused-hetero ring moiety, e.g., benzofurocarbazole or benzothienocarbazole, of the first host 232 and the biscarbazole moiety of the second host 234 can be deuterated. Namely, the fused-hetero ring moiety of the first host 232 is partially or wholly deuterated, or the biscarbazole moiety of the second host 234 is partially or wholly deuterated. Alternatively, the fused-hetero ring moiety of the first host 232 is partially or wholly deuterated, and the biscarbazole moiety of the second host 234 is partially or wholly deuterated.

Namely, in the OLED D of the present disclosure, the green EML 230 includes the first host 232 being the compound in Formula 1-1 and the second host 234 being the compound in Formula 2-1, and at least one of a1 and a2 in Formulas 1-1 and 2-1 can be a positive integer.

For example, when the first host 232 in Formula 1-1 is represented by Formula 1-2 (i.e., a1=~1~10 (positive integer) and each of b1, c1 and d1 is 0), the second host 234 can be represented by Formula 2-1. (when a1=1~10 and each of b1, c1 and d1 is 0, a2=0~14 and each of b2 and c2 is 0~9)

[Formula 1-2]

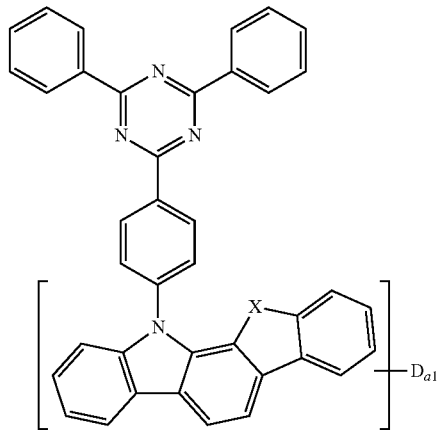

Alternatively, in the second host 234, the biscarbazole moiety except the biphenyl moiety can be partially or wholly deuterated. In this instance, the first host 232 can be non-deuterated, partially deuterated or wholly deuterated.

For example, when the second host 234 in Formula 2-1 is represented by Formula 2-2 (i.e., a2=1-14 (positive integer) and each of b2 and c2 is 0), the first host 232 can be represented by Formula 1-1. (when a2=1~14 and each of b2 and c2 is 0, a1=0~10, b1=0~4 and each of c1 and d1 is 0~5)

[Formula 2-2]

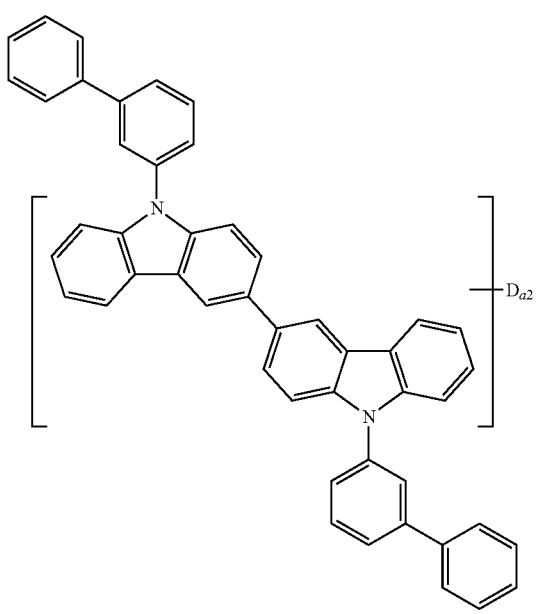

The first compound in Formula 1-1 can be selected from the compounds in Formula 3, and the first compound in Formula 1-2 can be the compound Host1-4 or the compound Host2-4.

[Formula 3]

Host 1-1

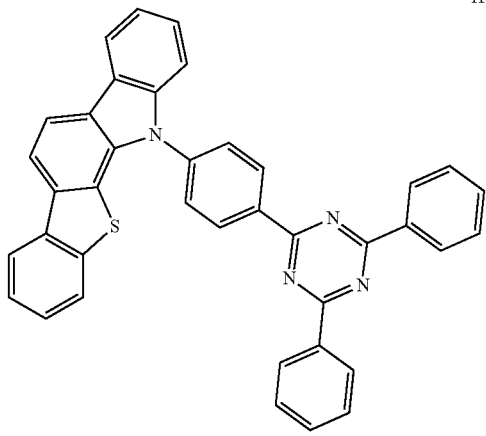

-continued
Host 1-2
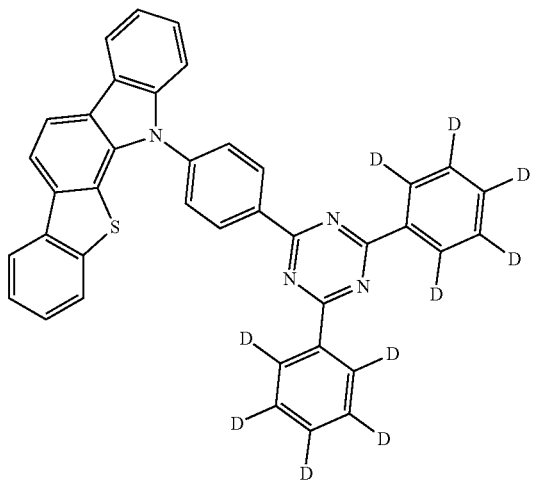
Host 1-3
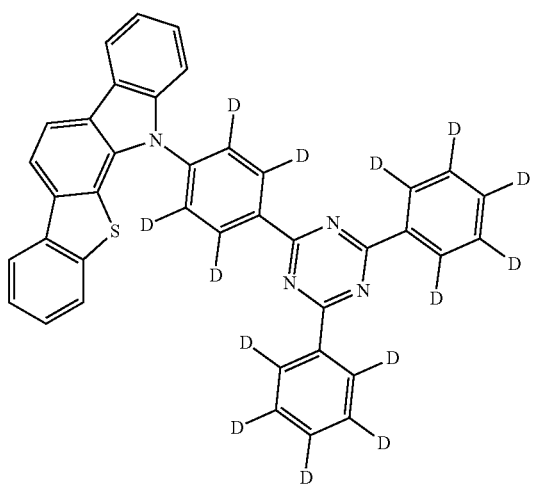
Host 1-4
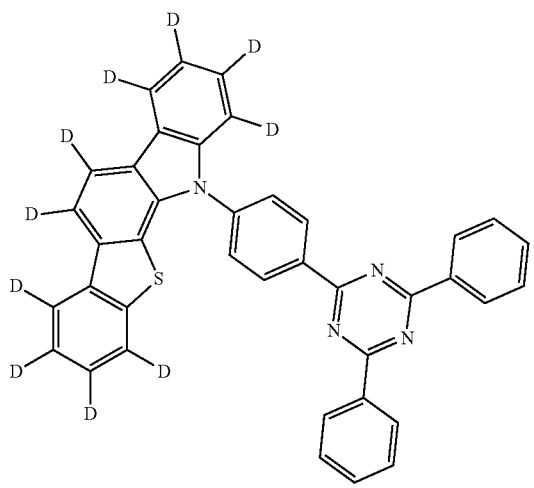
-continued
Host 1-5
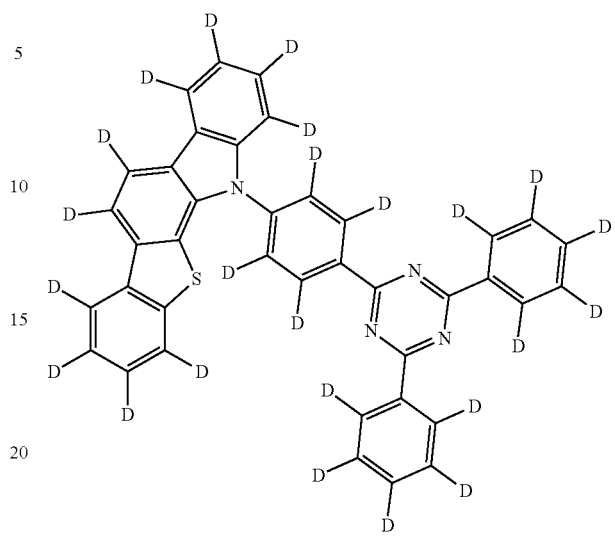
Host 2-1
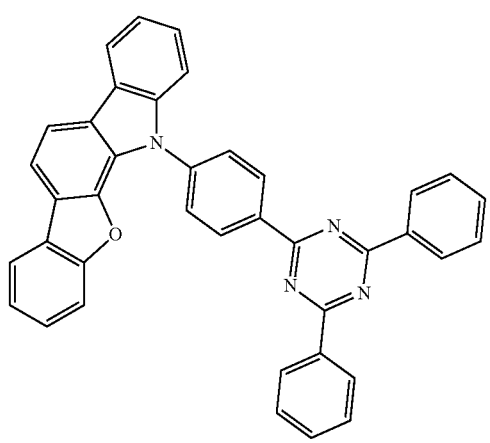
Host 2-2
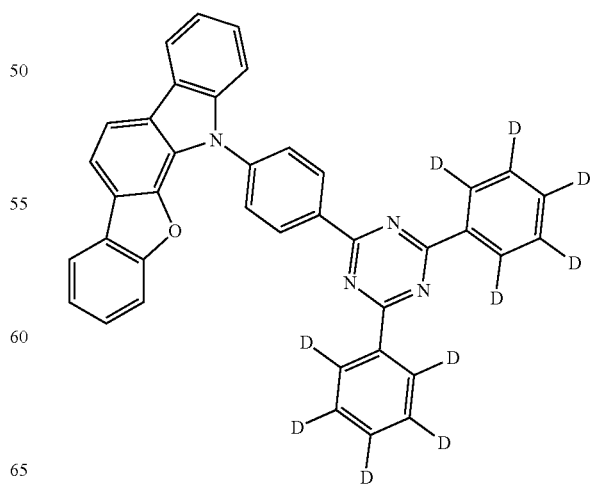

Host 2-3
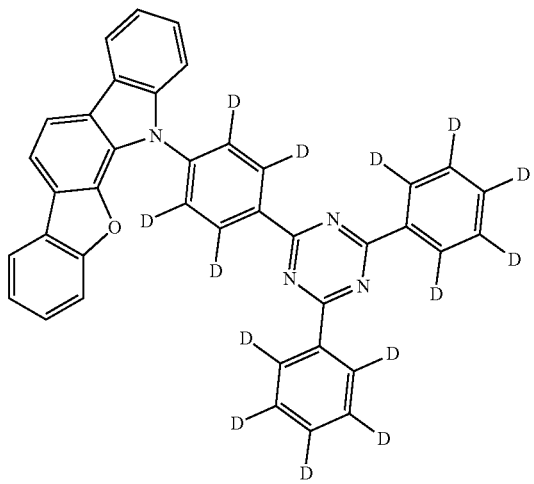
Host 2-5
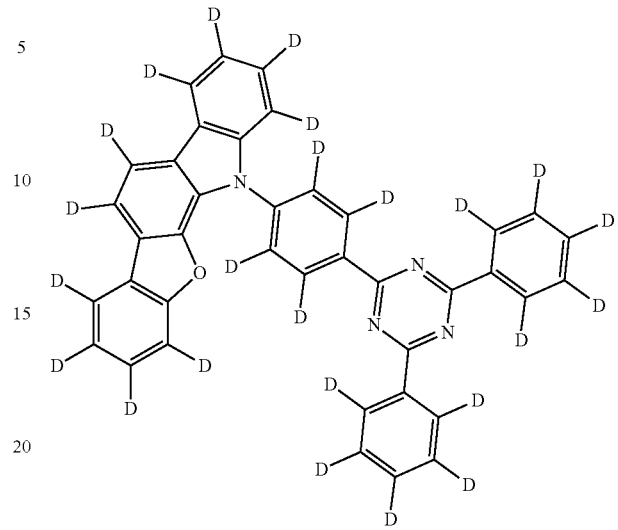
Host 2-4
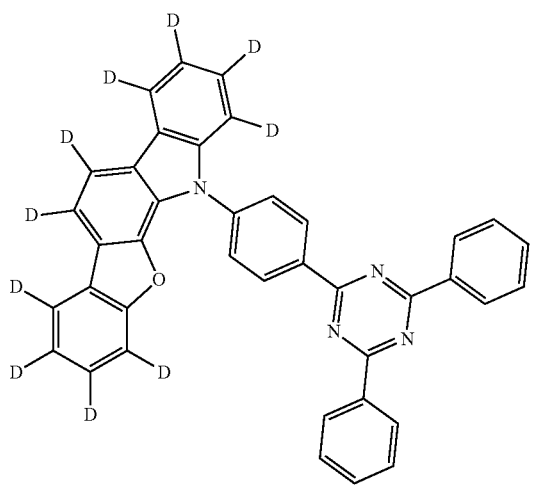
The second compound in Formula 2-1 can be selected from the compounds in Formula 4, and the second compound in Formula 2-2 can be the compound Host3-3.
[Formula 4]
Host 3-1
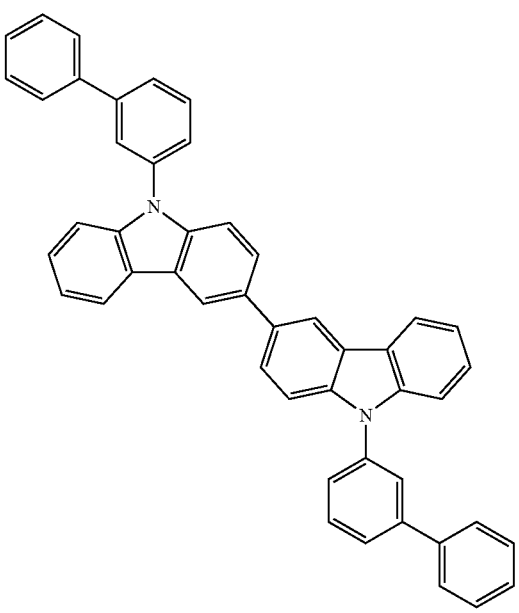

Host 3-2

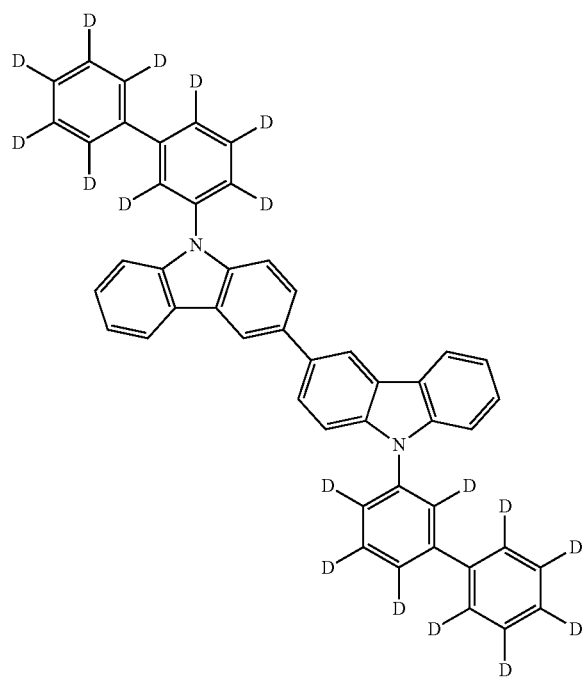

Host 3-4

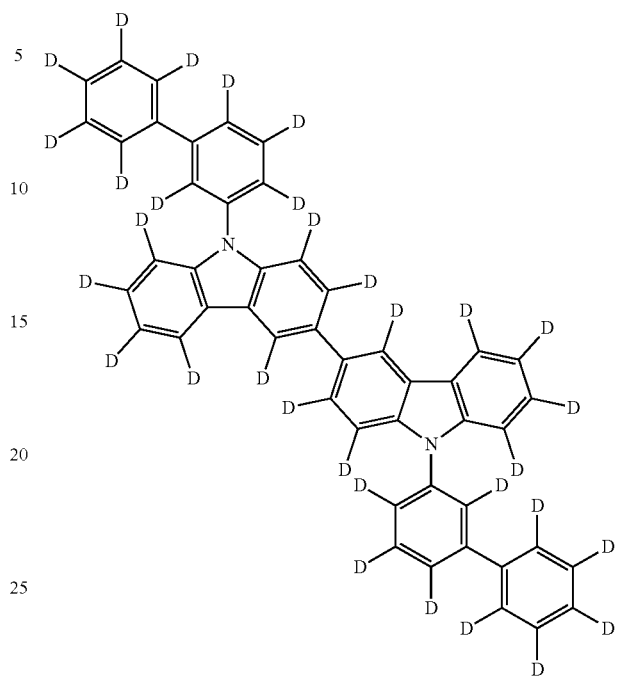

Host 3-3

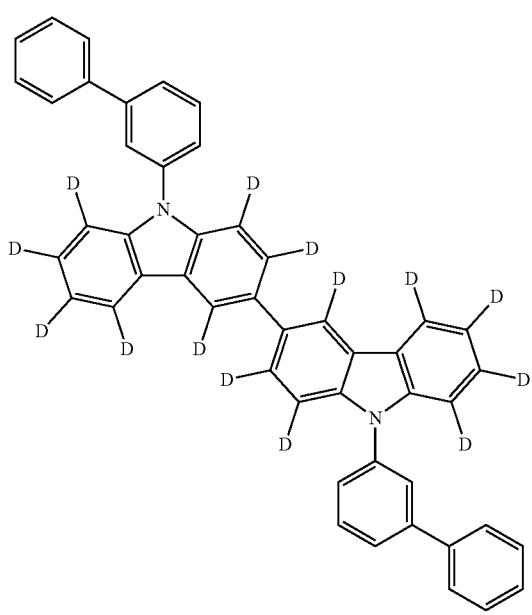

A case of the first host 232 being the compound Host1-1 or the compound Host2-1 and the second host 234 being the compound 3-1 is excluded from the present disclosure.

In the OLED D of the present disclosure, the green EML 230 includes the first host 232 in Formula 1-1 and the second host 234 in Formula 2-1, and at least one of the first and second hosts 232 and 234 is deuterated. As a result, the lifespan of the OLED D and the organic light emitting display device 100 is improved.

In addition, when only the fused-hetero ring moiety in the first host 232 is deuterated and/or only the biscarbazole moiety in the second host 234 is deuterated, the lifespan of the OLED D and the organic light emitting display device 100 is further improved.

[Synthesis]
1. Synthesis of the Compound Host1-1

[Reaction Formula 1]

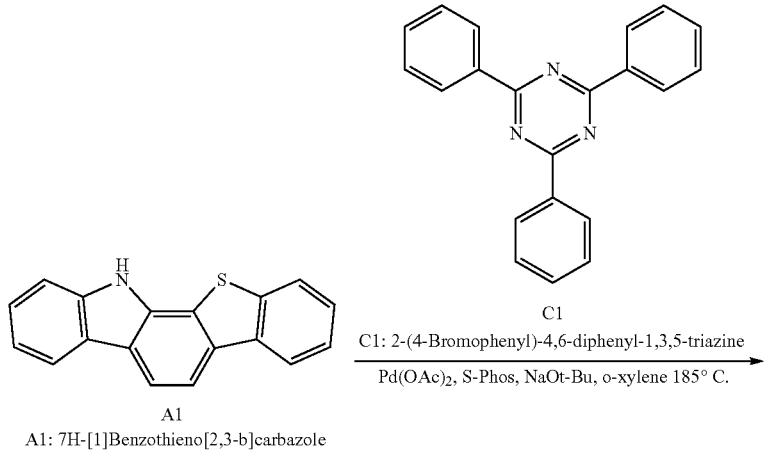

A1: 7H-[1]Benzothieno[2,3-b]carbazole
C1: 2-(4-Bromophenyl)-4,6-diphenyl-1,3,5-triazine
Pd(OAc)$_2$, S-Phos, NaOt-Bu, o-xylene 185° C.

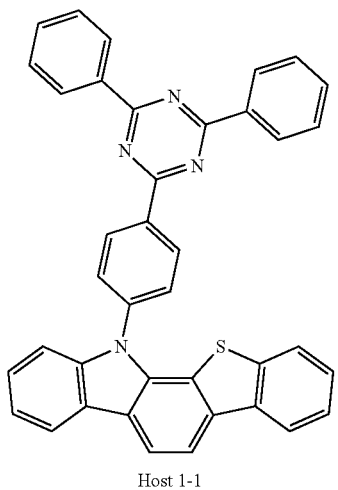

Host 1-1

In a flask, the compound A1 (13.67 g, 50 mmol), the compound C1 (23.30 g, 60 mmol), Pd(OAc)$_2$ (0.55 g, 2.49 mmol), S-Phos (2.04 g, 4.98 mmol), NaOt-Bu (8.6 g, 90.14 mmol) and o-xylene (500 ml) were mixed and heated at 185° C. for 4 hours. After cooling to room temperature, distilled water was added. The organic layer was extracted with ethyl acetate and distilled under reduced pressure. The obtained solid was separated by a column to obtain the compound Host1-1 (20.3 g, yield: 70.0%).

2. Synthesis of the Compound Host2-1

[Reaction Formula 2]

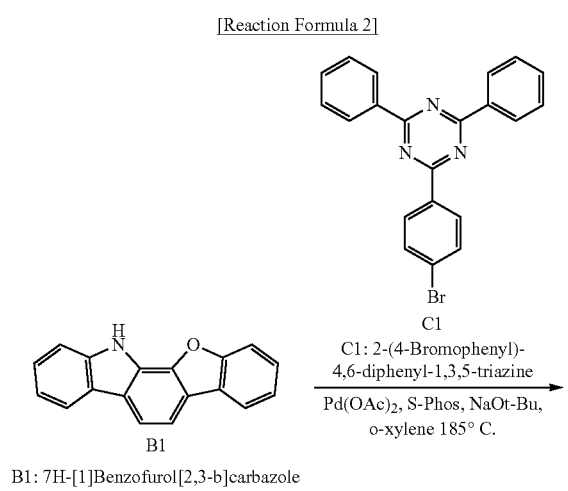

B1: 7H-[1]Benzofuro[2,3-b]carbazole

C1: 2-(4-Bromophenyl)-4,6-diphenyl-1,3,5-triazine

Pd(OAc)$_2$, S-Phos, NaOt-Bu, o-xylene 185° C.

Host 2-1

In a flask, the compound B1 (12.87 g, 50 mmol), the compound C1 (23.30 g, 60 mmol), Pd(OAc)$_2$ (0.55 g, 2.49 mmol), S-Phos (2.04 g, 4.98 mmol), NaOt-Bu (8.6 g, 90.14 mmol) and o-xylene (500 ml) were mixed and heated at 185° C. for 4 hours. After cooling to room temperature, distilled water was added. The organic layer was extracted with ethyl acetate and distilled under reduced pressure. The obtained solid was separated by a column to obtain the compound Host2-1 (19.76 g, yield: 70.0%).

3. Synthesis of the Compound Host1-2

(1) The Compound C2

[Reaction Formula 3-1]

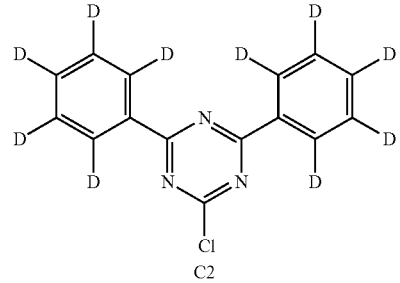

-continued

C2

In a flask, Mg (4.85 g, 200 mmol). THF (70 ml). I$_2$ (0.19 g, 0.70 mmol) were mixed, and bromobenzene-D5 (32.4 g, 200 mmol) was slowly added. Thereafter, the mixture was heated to 75° C. and cooled to room temperature after 30 minutes. 2,4,6-trichloro-1,3,5-triazine (14.75 g, 80 mmol) was dissolved in THF (120 ml). After cooling to 0° C., the Grignard reagent prepared above was slowly added. After stirring at room temperature for 12 hours, an aqueous NH$_4$Cl solution was added. The organic layer was extracted with ethyl acetate and residual moisture was removed using magnesium sulfate. Thereafter, the mixture was distilled under reduced pressure and separated by a column to obtain the compound C2 (14 g, yield: 63%).

(2) The Compound A2

[Reaction Formula 3-2]

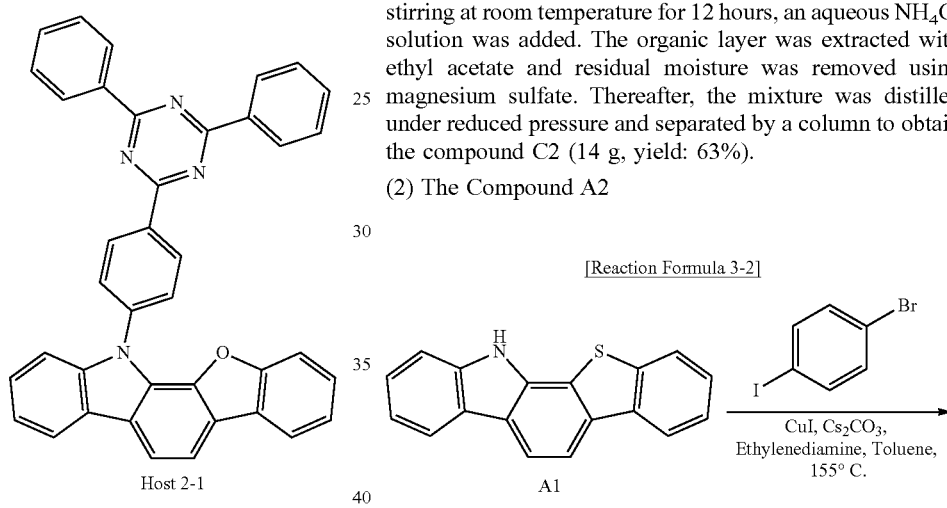

CuI, Cs$_2$CO$_3$, Ethylenediamine, Toluene, 155° C.

A1

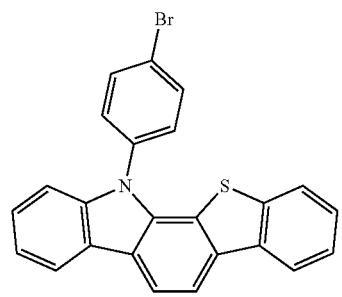

A2

In a flask, the compound A1 (25 g, 91.45 mmol), 4-bromoiodobenzene (51.58 g, 182.9 mmol), CuI (13.9 g, 73.16 mmol), toluene (1000 ml), Cs$_2$CO$_3$ (74.5 g, 228.6 mmol) and ethylenediamine (12.2 ml, 182.9 mmol) was added. It was heated to 155° C. and cooled to room temperature after 5 hours. Distilled water was added and the organic layer was extracted with ethyl acetate. After removing residual moisture using magnesium sulfate, the mixture was distilled under reduced pressure and separated by a column to obtain the compound A2 (18.5 g, yield: 47.23%).

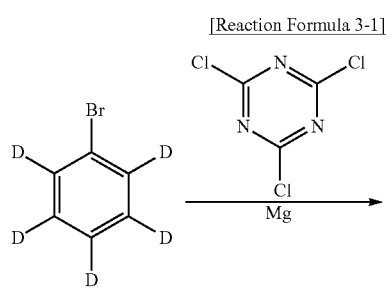

(3) The Compound A3

[Reaction Formula 3-3]

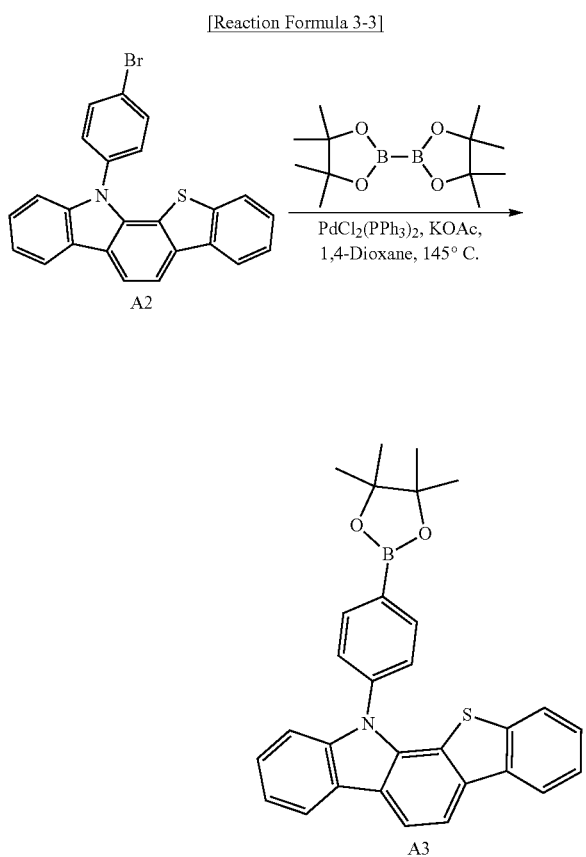

In a flask, the compound A2 (18.5 g, 43.18 mmol), 4,4,4',4',5,5,5',5'-octamethyl-2,2'-bi(1,3,2-dioxaborolane) (14.25 g, 56.14 mmol), PdCl$_2$(PPh$_3$), (1.5 g, 2.16 mmol), KOAc (8.5 g, 86.37 mmol), and 1,4-dioxane (800 ml) were added. The mixture was heated to 145° C. and cooled to room temperature after 4 hours. Distilled water was added and the organic layer was extracted with ethyl acetate. After removing residual moisture using magnesium sulfate, the mixture was distilled under reduced pressure and separated by a column to obtain the compound A3 (14 g, yield: 68.22%).

(4) The Compound Host1-2

[Reaction Formula 3-4]

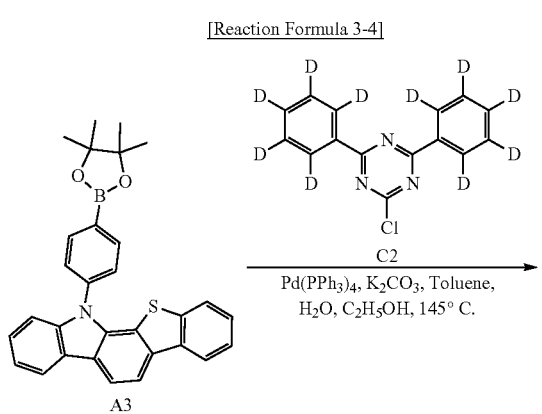

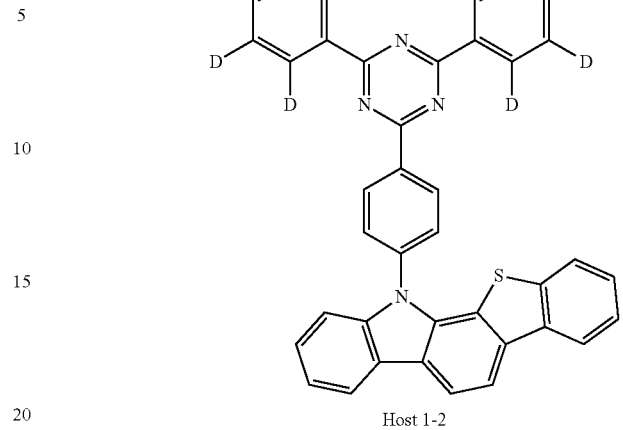

Host 1-2

In a flask, the compound A3 (14 g, 29.45 mmol), the compound C2 (8.9 g, 32.4 mmol), Pd(PPh$_3$)$_4$ (1.7 g, 1.47 mmol). K$_2$CO$_3$ (8.1 g, 58.89 mmol), toluene (400 ml), distilled water (60 ml) and ethanol (40 ml) were added. The mixture was heated to 145° C. and cooled to room temperature after 5 hours. Distilled water was added and the organic layer was extracted with ethyl acetate. After removing residual moisture using magnesium sulfate, the mixture was distilled under reduced pressure and separated by a column to obtain the compound Host1-2 (10.5 g, yield: 60.3%).

4. Synthesis of the Compound Host1-3

(1) 1-bromo-4-iodobenzene-d4

[Reaction Formula 4-1]

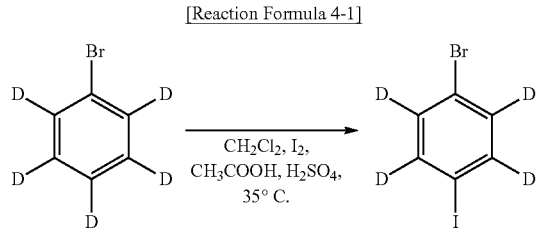 [SMILES: [2H]c1c([2H])c([2H])c(Br)c([2H])c1[2H] ; [2H]c1c([2H])c(I)c([2H])c([2H])c1Br]

In a flask, 5-bromobenzene-d5 (36 g, 222.16 mmol), dichloromethane (216 ml), 12 (45 g, 177.7 mmol), acetic acid (CH$_3$COOH, 108 ml) and sulfuric acid (H$_2$SO$_4$, 3.5 ml) were added and stirred for 10 minutes at 35° C. K$_2$S$_2$O$_8$ (18.01 g, 66.65 mmol) was added to the mixture. The reaction temperature was heated to 45° C. and cooled to room temperature after 4 hours. The reaction solution was slowly added to the aqueous potassium carbonate solution. After neutralization, the organic layer was extracted with dichloromethane. The organic layer was again put into sodium thiosulfate aqueous solution and stirred. The organic layer was separated from the water layer. After removing residual moisture using magnesium sulfate, the mixture was dried and separated by a column to obtain 1-bromo-4-iodobenzene-d4 (27 g, yield: 42.8%).

(2) The Compound A4

[Reaction Formula 4-2]

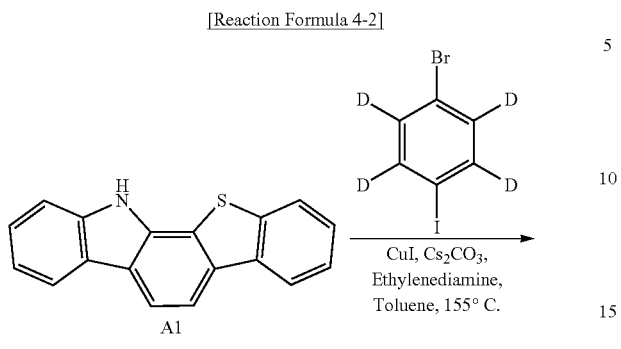

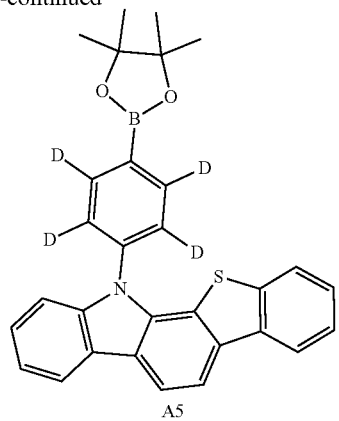

In a flask, the compound A1 (20 g, 73.16 mmol), 1-bromo-4-iodobenzene-d4 (27.29 g, 95.11 mmol), CuI (11.14 g, 58.53 mmol), toluene (700 ml), Cs₂CO₃ (59.59 g, 182.91 mmol) and ethylenediamine (9.8 ml, 146.3 mmol) was added. It was heated to 155° C. and cooled to room temperature after 19 hours. Distilled water was added and the organic layer was extracted with ethyl acetate. After removing residual moisture using magnesium sulfate, the mixture was distilled under reduced pressure and separated by a column to obtain the compound A4 (18.5 g, yield: 47.23%).

(3) The Compound A5

[Reaction Formula 4-3]

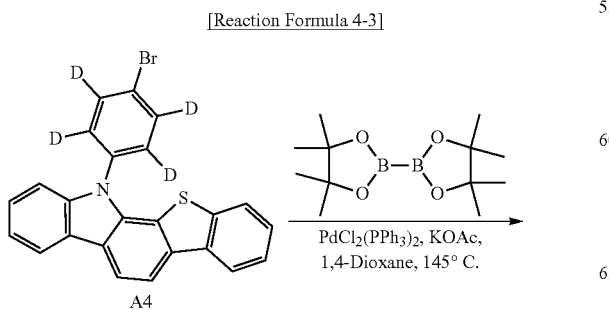

In a flask, the compound A4 (23 g, 53.19 mmol), 4,4,4',4',5,5,5'5'-octamethyl-2,2'-bi(1,3,2-dioxaborolane) (17.5 g, 69.15 mmol), PdCl₂(PPh₃)₂ (1.86 g, 2.66 mmol), KOAc (10.46 g, 106.4 mmol), and 1,4-dioxane (900 ml) were added. The mixture was heated to 145° C. and cooled to room temperature after 5 hours. Distilled water was added and the organic layer was extracted with ethyl acetate. After removing residual moisture using magnesium sulfate, the mixture was distilled under reduced pressure and separated by a column to obtain the compound A5 (14 g, yield: 54.9%).

(4) The Compound Host1-3

[Reaction Formula 4-4]

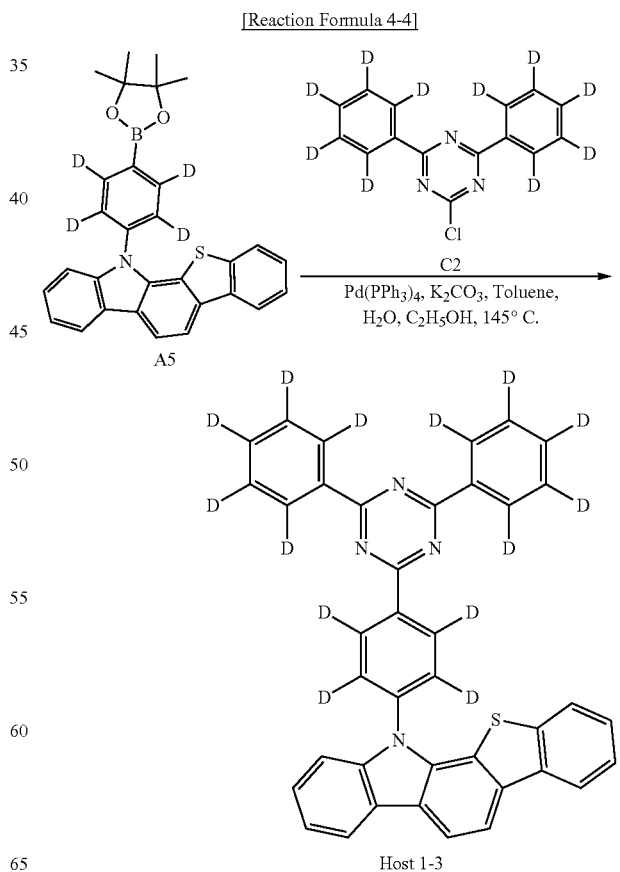

In a flask, the compound A5 (14 g, 29.20 mmol), the compound C2 (8.9 g, 32.12 mmol), Pd(PPh$_3$)$_4$ (1.68 g, 1.46 mmol), K$_2$CO$_3$ (8.0 g, 58.40 mmol), toluene (400 ml), distilled water (60 ml) and ethanol (40 ml) were added. The mixture was refluxed and stirred and cooled to room temperature after 5 hours. Distilled water was added and the organic layer was extracted with ethyl acetate. After removing residual moisture using magnesium sulfate, the mixture was distilled under reduced pressure and separated by a column to obtain the compound Host1-3 (10.5 g, yield: 60.45%).

5. Synthesis of the Compound Host1-4

(1) The Compound A6

[Reaction Formula 5-1]

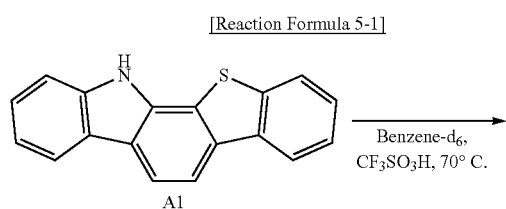

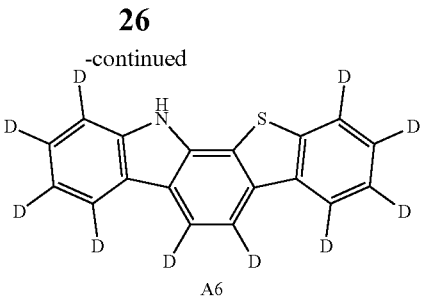

A6

In a flask, the compound A1 (20.0 g, 9.0 mmol) and benzene-d6 (1.4 kg) were added and refluxed and stirred. Triflic acid (65.88 g, 438.9 mmol) was added at 70° C. After 5 hours, it was cooled to room temperature. D20 (40 ml) was mixed and stirred for 10 minutes. The mixture was neutralized with an aqueous K$_3$PO$_4$ solution, and the organic layer was extracted with ethyl acetate. After removing residual moisture using magnesium sulfate, the mixture was distilled under reduced pressure and separated by a column to obtain the compound A6 (15 g, yield: 72.99%).

(2) The Compound Host1-4

[Reaction Formula 5-2]

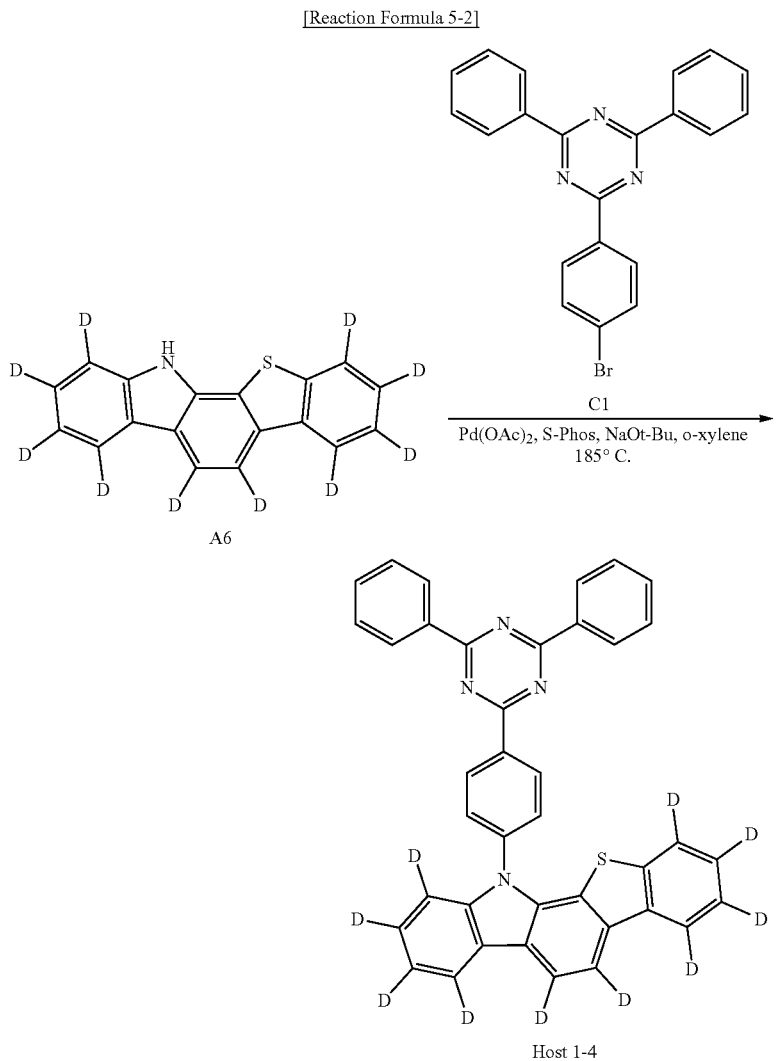

Host 1-4

In a flask, the compound A6 (14 g, 49.8 mmol), the compound C1 (23.21 g, 59.78 mmol), Pd(OAc)$_2$ (0.55 g, 2.49 mmol), S-Phos (2.04 g, 4.98 mmol), NaOt-Bu (8.6 g, 90.14 mmol) and o-xylene (500 ml) were mixed and heated at 185° C. for 4 hours. After cooling to room temperature, distilled water was added. The organic layer was extracted with ethyl acetate and distilled under reduced pressure. The obtained solid was separated by a column to obtain the compound Host1-4 (20.5 g, yield: 70.0%).

6. Synthesis of the Compound Host1-5

(1) The Compound A7

[Reaction Formula 6-1]

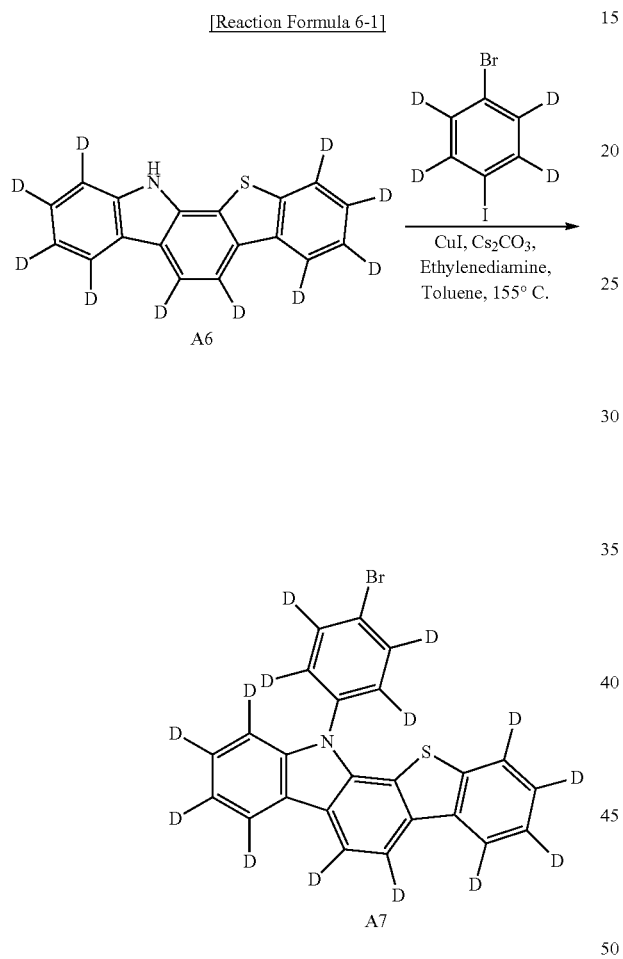

A6

A7

(2) The Compound A8

[Reaction Formula 6-2]

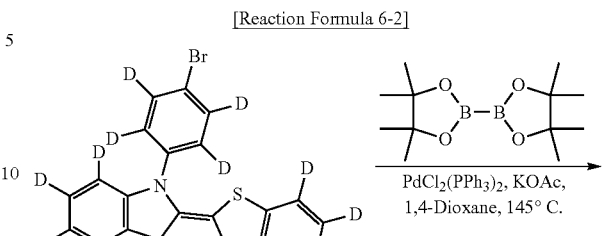

A7

A8

In a flask, the compound A6 (20.8 g, 73.16 mmol), 1-bromo-4-iodobenzene-d4 (27.29 g, 95.11 mmol), CuI (11.14 g, 58.53 mmol), toluene (700 ml), Cs$_2$CO$_3$ (59.59 g, 182.91 mmol) and ethylenediamine (9.8 ml, 146.3 mmol) was added. It was heated to 155° C. and cooled to room temperature after 19 hours. Distilled water was added and the organic layer was extracted with ethyl acetate. After removing residual moisture using magnesium sulfate, the mixture was distilled under reduced pressure and separated by a column to obtain the compound A7 (19.1 g, yield: 47.23%).

In a flask, the compound A7 (23.75 g, 53.19 mmol), 4,4,4',4',5,5,5',5'-octamethyl-2,2'-bi(1,3,2-dioxaborolane) (17.5 g, 69.15 mmol), PdCl$_2$(PPh$_3$)$_2$ (1.86 g, 2.66 mmol), KOAc (10.46 g, 106.4 mmol), and 1,4-dioxane (900 ml) were added. The mixture was heated to 145° C. and cooled to room temperature after 5 hours. Distilled water was added and the organic layer was extracted with ethyl acetate. After removing residual moisture using magnesium sulfate, the mixture was distilled under reduced pressure and separated by a column to obtain the compound A8 (14.4 g, yield: 54.9%).

(3) The Compound Host1-5
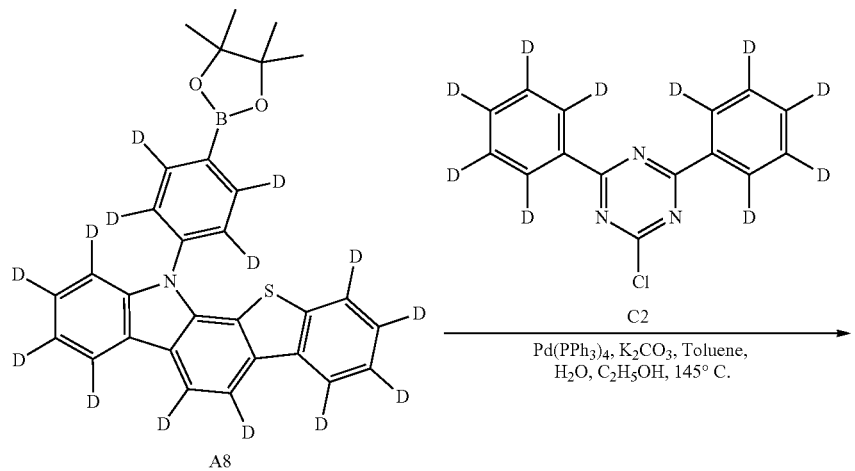
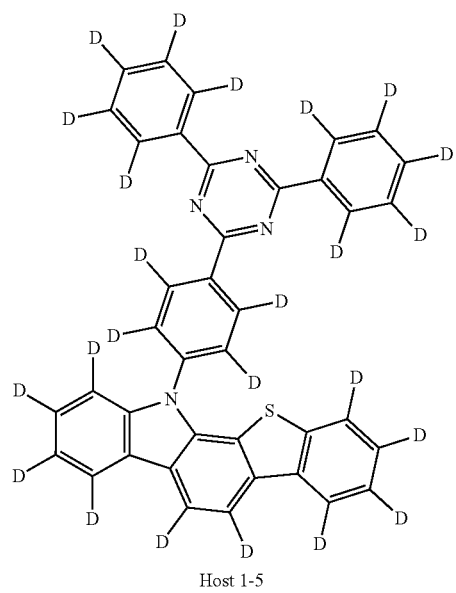
Host 1-5

In a flask, the compound A8 (14.4 g, 29.20 mmol), the compound C2 (8.9 g, 32.12 mmol), Pd(PPh₃)₄ (1.68 g, 1.46 mmol), K₂CO₃ (8.0 g, 58.40 mmol), toluene (400 ml), distilled water (60 ml) and ethanol (40 ml) were added. The mixture was refluxed and heated and cooled to room temperature after 5 hours. Distilled water was added and the organic layer was extracted with ethyl acetate. After removing residual moisture using magnesium sulfate, the mixture was distilled under reduced pressure and separated by a column to obtain the compound Host1-5 (10.67 g, yield: 60.45%).

7. Synthesis of the Compound Host2-2
(1) The Compound B2

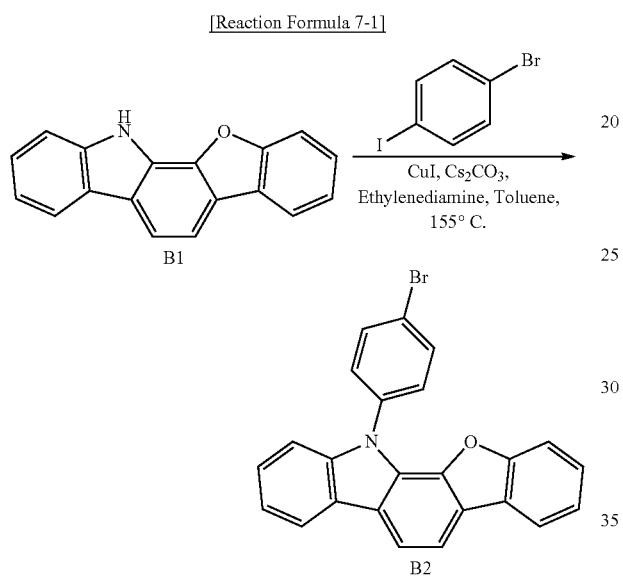

[Reaction Formula 7-1]

In a flask, the compound B1 (18.8 g, 73.16 mmol), 1-bromo-4-iodobenzene (27.29 g, 96.47 mmol), CuI (11.14 g, 58.53 mmol), toluene (700 ml), Cs₂CO₃ (59.59 g, 182.91 mmol) and ethylenediamine (9.8 ml, 146.3 mmol) was added. It was heated to 155° C. and cooled to room temperature after 19 hours. Distilled water was added and the organic layer was extracted with ethyl acetate. After removing residual moisture using magnesium sulfate, the mixture was distilled under reduced pressure and separated by a column to obtain the compound B2 (17.8 g, yield: 47.23%).

(2) The Compound B3

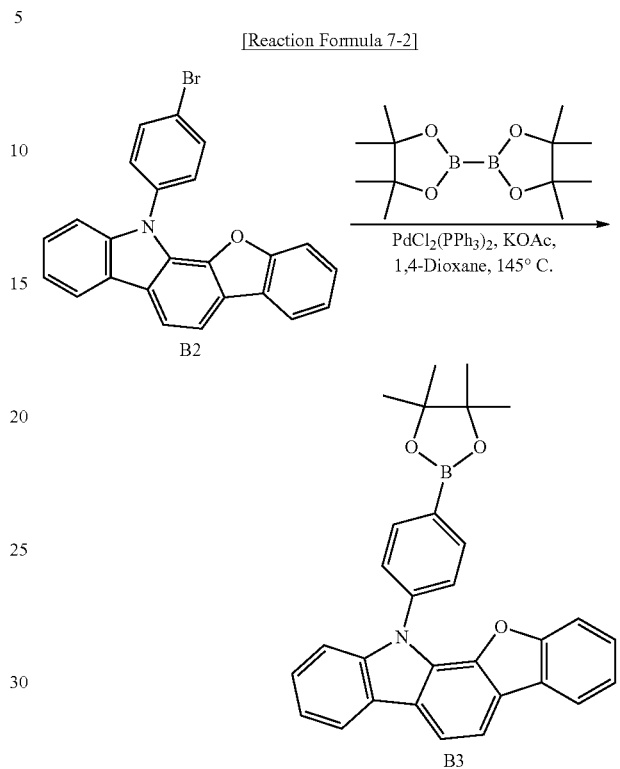

[Reaction Formula 7-2]

In a flask, the compound B2 (17.8 g, 43.18 mmol), 4,4,4,4',5,5,5',5'-octamethyl-2,2'-bi(1,3,2-dioxaborolane) (14.25 g, 56.14 mmol), PdCl₂ (PPh₃ (1.5 g, 2.16 mmol), KOAc (8.5 g, 86.37 mmol), and 1,4-dioxane (800 ml) were added. The mixture was heated to 145° C. and cooled to room temperature after 4 hours. Distilled water was added and the organic layer was extracted with ethyl acetate. After removing residual moisture using magnesium sulfate, the mixture was distilled under reduced pressure and separated by a column to obtain the compound B3 (13.53 g, yield: 68.22%).

(3) The Compound Host2-2

[Reaction Formula 7-3]

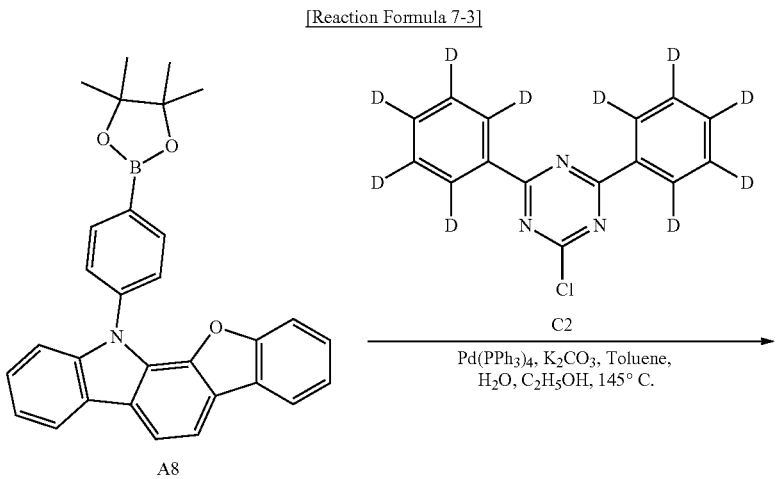

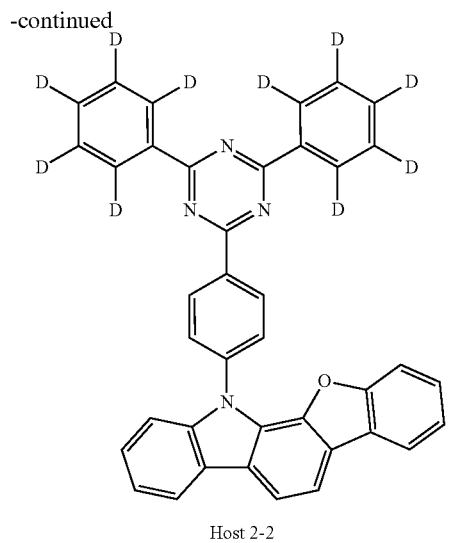

Host 2-2

In a flask, the compound B3 (13.52 g, 29.45 mmol), the compound C2 (8.9 g, 32.4 mmol), Pd(PPh$_3$)$_4$ (1.7 g, 1.47 mmol), K$_2$CO$_3$ (8.1 g, 58.89 mmol), toluene (400 ml), distilled water (60 ml) and ethanol (40 ml) were added. The mixture was heated to 145° C. and cooled to room temperature after 5 hours. Distilled water was added and the organic layer was extracted with ethyl acetate. After removing residual moisture using magnesium sulfate, the mixture was distilled under reduced pressure and separated by a column to obtain the compound Host2-2 (10.21 g, yield: 60.3%).

8. Synthesis of the Compound Host2-3

(1) the Compound B4 was added. It was heated to 155° C. and cooled to room temperature after 19 hours. Distilled water was added and the organic layer was extracted with ethyl acetate. After removing residual moisture using magnesium sulfate, the mixture was distilled under reduced pressure and separated by a column to obtain the compound B4 (17.81 g. yield: 47.23%).

(2) The Compound B5

[Reaction Formula 8-1]

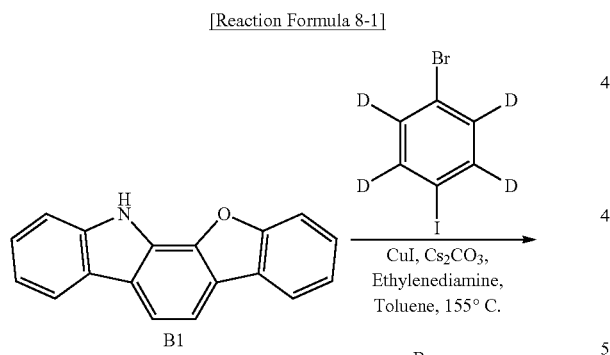

[Reaction Formula 8-2]

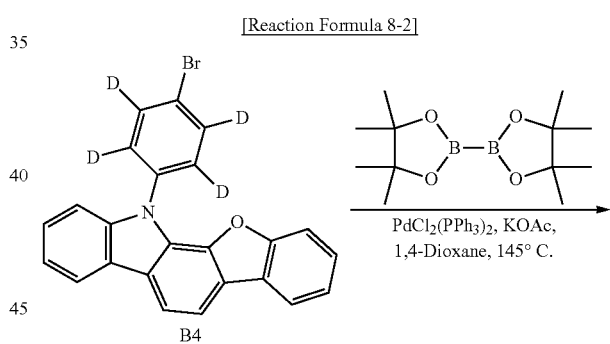

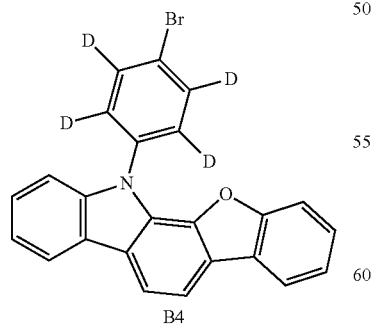

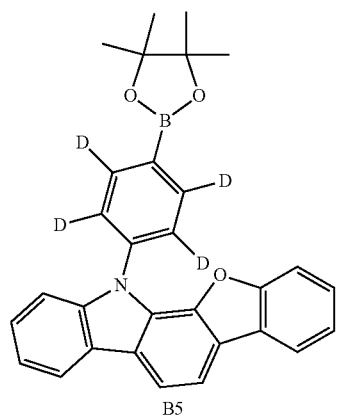

In a flask, the compound B1 (18.81 g, 73.16 mmol), 1-bromo-4-iodobenzene-d4 (27.29 g, 95.11 mmol), CuI (11.14 g, 58.53 mmol), toluene (700 ml), Cs$_2$CO$_3$ (59.59 g, 182.91 mmol) and ethylenediamine (9.8 ml, 146.3 mmol)

In a flask, the compound B4 (22.14 g, 53.19 mmol), 4,4,4',4',5,5,5'5'-octamethyl-2,2'-bi(1,3,2-dioxaborolane) (17.5 g, 69.15 mmol). PdCl$_2$(PPh$_3$)$_2$ (1.86 g, 2.66 mmol), KOAc (10.46 g, 106.4 mmol), and 1,4-dioxane (900 ml) were added. The mixture was heated to 145° C. and cooled to room temperature after 5 hours. Distilled water was added and the organic layer was extracted with ethyl acetate. After removing residual moisture using magnesium sulfate, the mixture was distilled under reduced pressure and separated by a column to obtain the compound B5 (13.53 g, yield: 54.9%).

(3) The Compound Host2-3

[Reaction Formula 8-3]

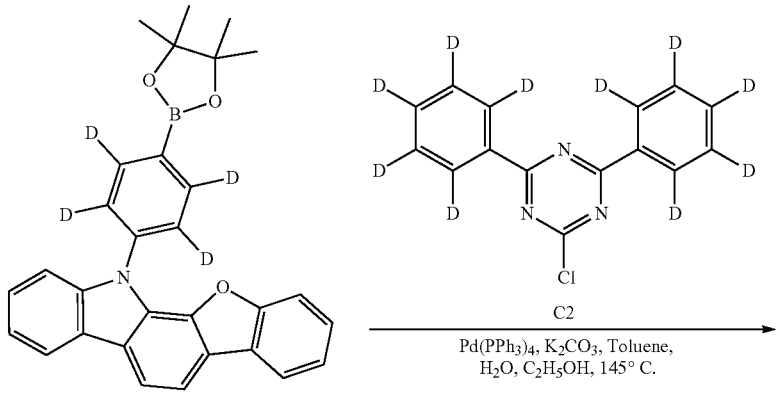

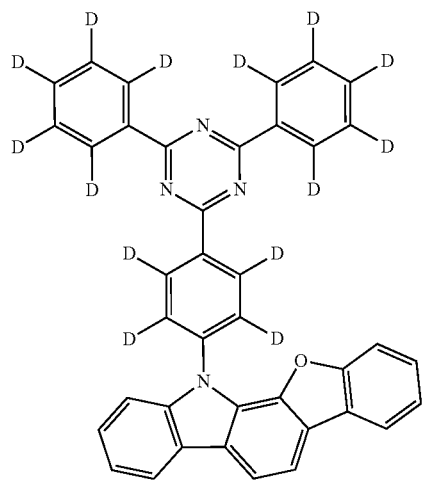

Host 2-3

In a flask, the compound B5 (13.53 g, 29.20 mmol), the compound C2 (8.9 g, 32.12 mmol), Pd(PPh$_3$)$_4$ (1.68 g, 1.46 mmol), K$_2$CO$_3$ (8.0 g, 58.40 mmol), toluene (400 ml), distilled water (60 ml) and ethanol (40 ml) were added. The mixture was refluxed and stirred and cooled to room temperature after 5 hours. Distilled water was added and the organic layer was extracted with ethyl acetate. After removing residual moisture using magnesium sulfate, the mixture was distilled under reduced pressure and separated by a column to obtain the compound Host2-3 (10.2 g, yield: 60.45%).

9. Synthesis of the Compound Host2-4

(1) The Compound B6

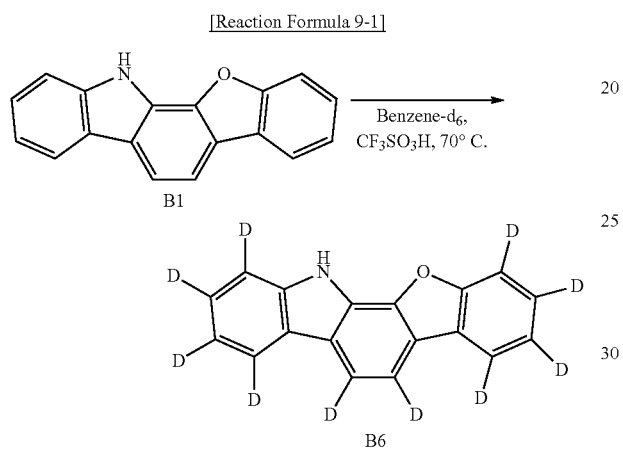

In a flask, the compound B1 (18.8 g, 9.0 mmol) and benzene-d6 (1.4 kg) were added and refluxed and stirred. Triflic acid (65.88 g, 438.9 mmol) was added at 70° C. After 5 hours, it was cooled to room temperature. D$_2$O (40 ml) was mixed and stirred for 10 minutes. The mixture was neutralized with an aqueous K$_3$PO$_4$ solution, and the organic layer was extracted with ethyl acetate. After removing residual moisture using magnesium sulfate, the mixture was distilled under reduced pressure and separated by a column to obtain the compound B6 (14.15 g, yield: 72.99%).

(2) The Compound Host2-4

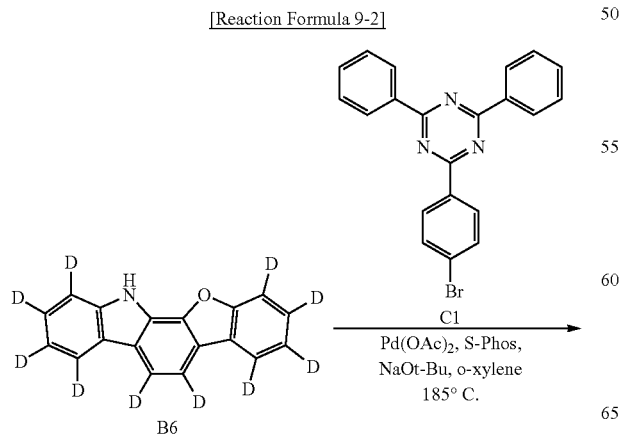

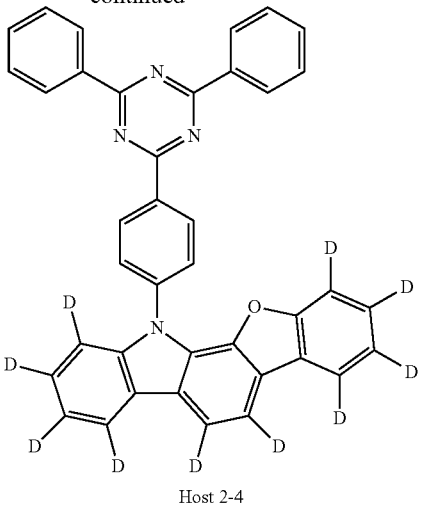

Host 2-4

In a flask, the compound B6 (13.20 g, 49.8 mmol), the compound C1 (23.21 g, 59.78 mmol), Pd(OAc)$_2$ (0.55 g, 2.49 mmol), S-Phos (2.04 g, 4.98 mmol), NaOt-Bu (8.6 g, 90.14 mmol) and o-xylene (500 ml) were mixed and heated at 185° C. for 4 hours. After cooling to room temperature, distilled water was added. The organic layer was extracted with ethyl acetate and distilled under reduced pressure. The obtained solid was separated by a column to obtain the compound Host2-4 (19.9 g, yield: 70.0%).

10. Synthesis of the Compound Host2-5

(1) The Compound B7

[Reaction Formula 10-1]

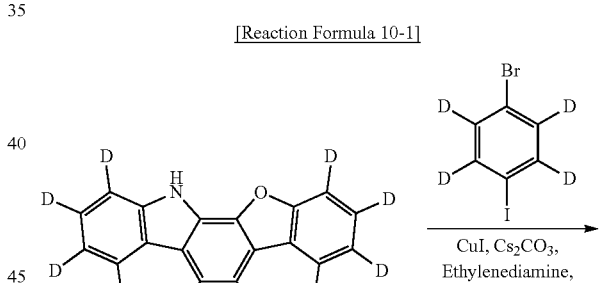

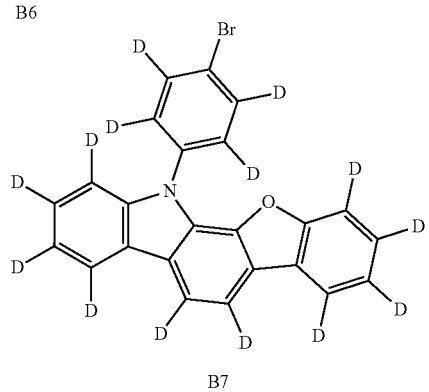

B7

In a flask, the compound B6 (19.6 g, 73.16 mmol), 1-bromo-4-iodobenzene-d4 (27.29 g, 95.11 mmol), CuI (11.14 g, 58.53 mmol), toluene (700 ml), Cs$_2$CO$_3$ (59.59 g, 182.91 mmol) and ethylenediamine (9.8 ml, 146.3 mmol)

was added. It was heated to 155° C. and cooled to room temperature after 19 hours. Distilled water was added and the organic layer was extracted with ethyl acetate. After removing residual moisture using magnesium sulfate, the mixture was distilled under reduced pressure and separated by a column to obtain the compound B7 (18.4 g, yield: 47.23%).

(2) The Compound B8

[Reaction Formula 10-2]

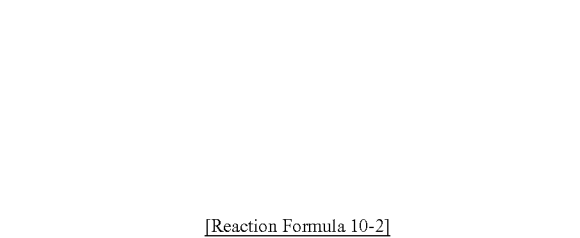

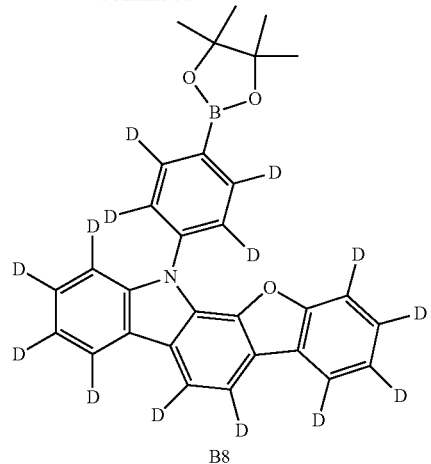

In a flask, the compound B7 (22.88 g, 53.19 mmol), 4,4,4',4',5,5,5',5'-octamethyl-2,2'-bi(1,3,2-dioxaborolane) (17.5 g, 69.15 mmol), PdCl$_2$(PPh$_3$)$_2$ (1.86 g, 2.66 mmol), KOAc (10.46 g, 106.4 mmol), and 1,4-dioxane (900 ml) were added. The mixture was heated to 145° C. and cooled to room temperature after 5 hours. Distilled water was added and the organic layer was extracted with ethyl acetate. After removing residual moisture using magnesium sulfate, the mixture was distilled under reduced pressure and separated by a column to obtain the compound B8 (13.9 g. yield: 54.9%).

(3) The Compound Host2-5

[Reaction Formula 10-3]

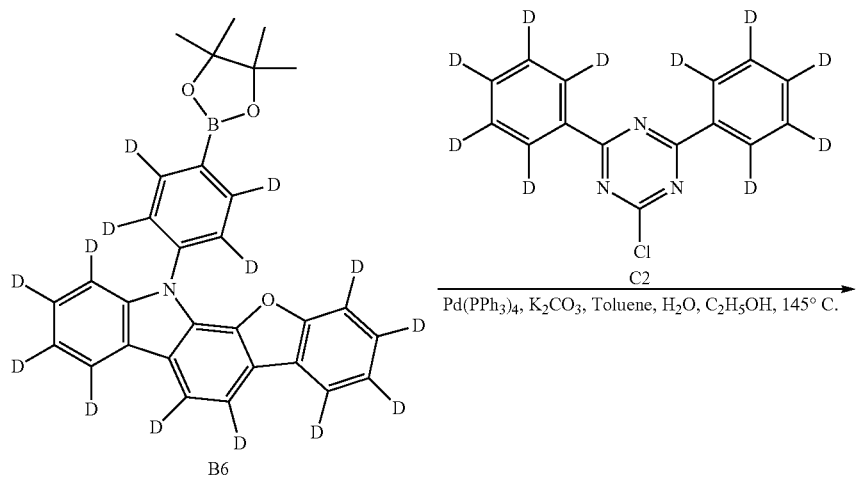

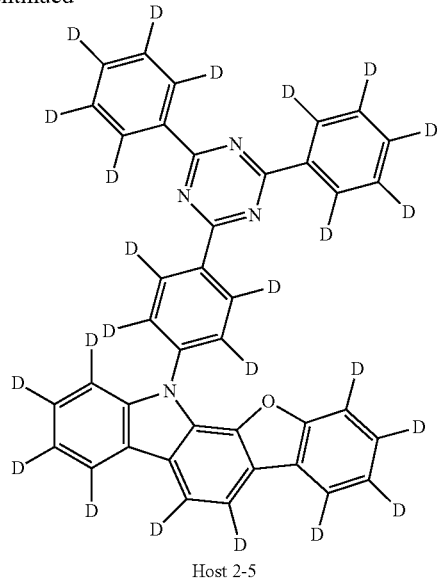

Host 2-5

In a flask, the compound B8 (13.9 g, 29.20 mmol), the compound C2 (8.9 g, 32.12 mmol), Pd(PPh₃)₄ (1.68 g, 1.46 mmol), K₂CO₃ (8.0 g, 58.40 mmol), toluene (400 ml), distilled water (60 ml) and ethanol (40 ml) were added. The mixture was refluxed and heated and cooled to room temperature after 5 hours. Distilled water was added and the organic layer was extracted with ethyl acetate. After removing residual moisture using magnesium sulfate, the mixture was distilled under reduced pressure and separated by a column to obtain the compound Host2-5 (10.39 g, yield: 60.45%).

11. Synthesis of the Compound Host3-2

(1) 3-bromobiphenyl-d9

[Reaction Formula 11-1]

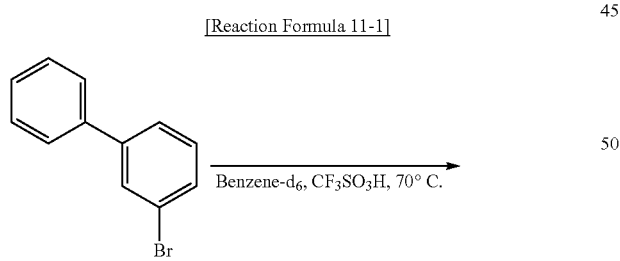

In a flask, 3-bromobiphenyl (21.0 g, 9.0 mmol) and benzene-d6 (1.4 kg) were added and refluxed and stirred. Triflic acid (65.88 g, 438.9 mmol) was added at 70° C. After 5 hours, it was cooled to room temperature. D20 (40 ml) was mixed and stirred for 10 minutes. The mixture was neutralized with an aqueous K₃PO₄ solution, and the organic layer was extracted with ethyl acetate. After removing residual moisture using magnesium sulfate, the mixture was distilled under reduced pressure and separated by a column to obtain 3-bromobiphenyl-d9 (15.92 g, yield: 72.99%).

(2) The Compound Host3-2

[Reaction Formula 11-2]

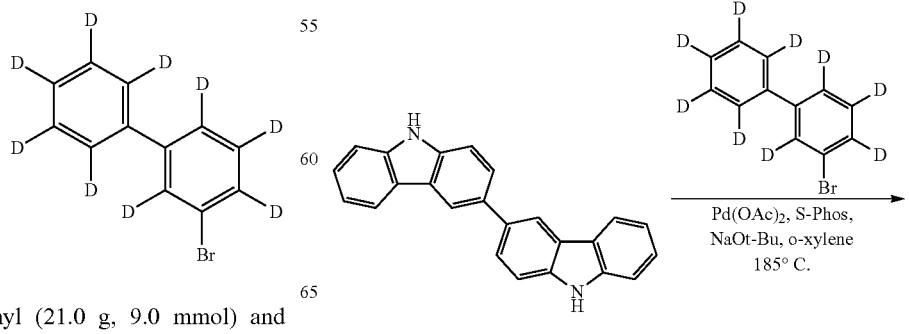

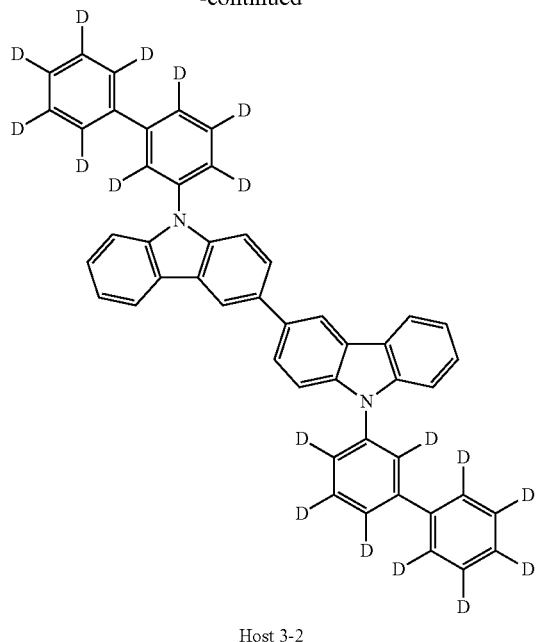

Host 3-2

In a flask, 3,3'-biscarbazole (16.55 g, 49.8 mmol), 3-bromobiphenyl-d9 (26.63 g, 110 mmol), Pd(OAc)$_2$ (0.55 g, 2.49 mmol), S-Phos (2.04 g, 4.98 mmol), NaOt-Bu (10.5 g, 90.14 mmol) and o-xylene (500 ml) were mixed and heated at 185° C. for 4 hours. After cooling to room temperature, distilled water was added. The organic layer was extracted with ethyl acetate and distilled under reduced pressure. The obtained solid was separated by a column to obtain the compound Host3-2 (22.82 g, yield: 70.0%).

12. Synthesis of the Compound Host3-3
(1) 3,3'-Biscarbazole-d14

[Reaction Formula 12-1]

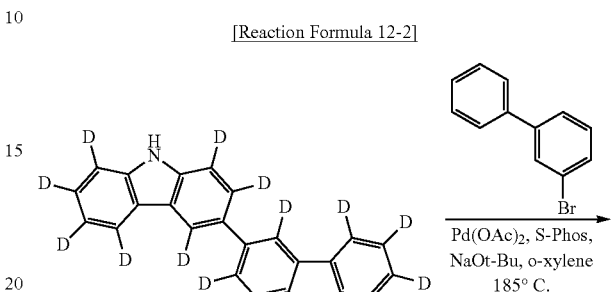

In a flask, 3,3'-biscarbazole (29.9 g, 90 mmol) and benzene-d6 (1.4 kg) were added and refluxed and stirred. Triflic acid (65.88 g, 438.9 mmol) was added at 70° C. After 5 hours, it was cooled to room temperature. D20 (40 ml) was mixed and stirred for 10 minutes. The mixture was neutralized with an aqueous K$_3$PO$_4$ solution, and the organic layer was extracted with ethyl acetate. After removing residual moisture using magnesium sulfate, the mixture was distilled under reduced pressure and separated by a column to obtain 3,3'-biscarbazole-d14 (22.76 g, yield: 72.99%).

(2) The Compound Host3-3

[Reaction Formula 12-2]

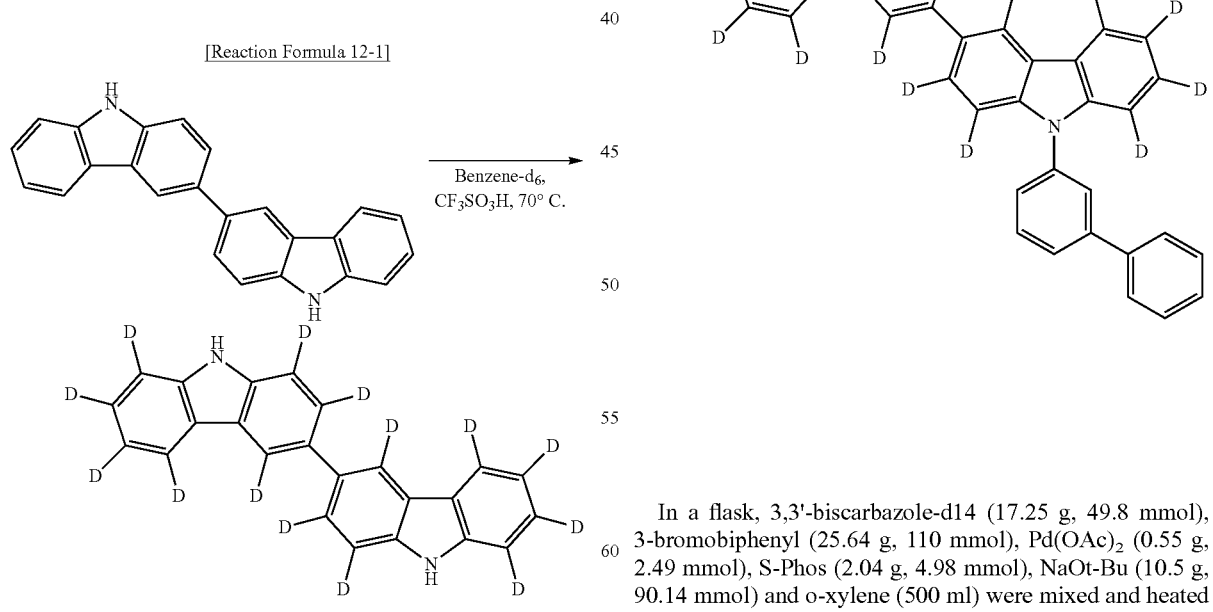

In a flask, 3,3'-biscarbazole-d14 (17.25 g, 49.8 mmol), 3-bromobiphenyl (25.64 g, 110 mmol), Pd(OAc)$_2$ (0.55 g, 2.49 mmol), S-Phos (2.04 g, 4.98 mmol), NaOt-Bu (10.5 g, 90.14 mmol) and o-xylene (500 ml) were mixed and heated at 185° C. for 4 hours. After cooling to room temperature, distilled water was added. The organic layer was extracted with ethyl acetate and distilled under reduced pressure. The obtained solid was separated by a column to obtain the compound Host3-3 (22.69 g, yield: 70.0%).

13. Synthesis of the Compound Host3-4

[Reaction Formula 13]

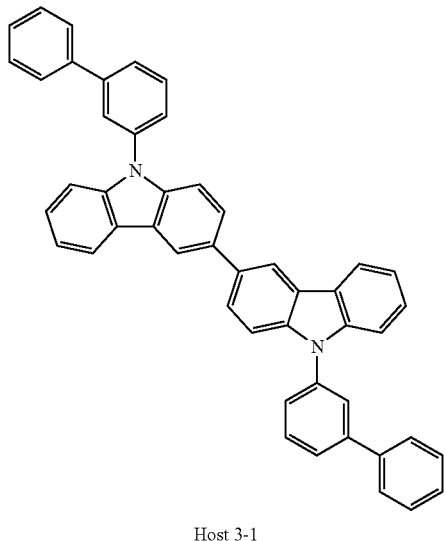

Host 3-1

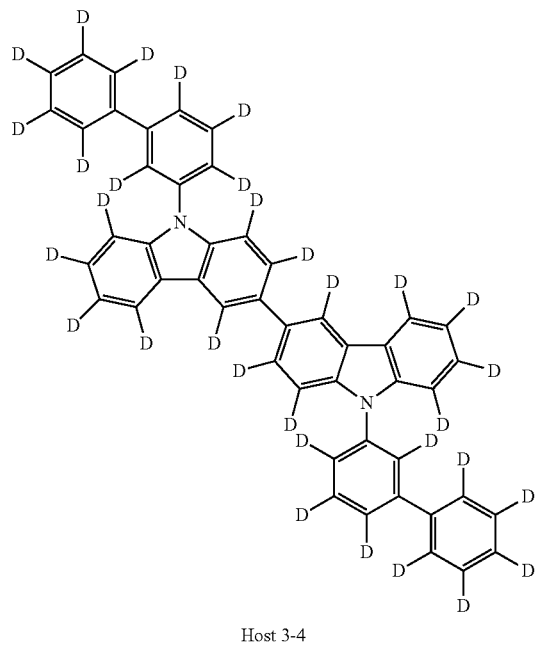

Host 3-4

In a flask, the compound Host3-1 (15.0 g, 42.9 mmol) and benzene-do (900 ml) were added and heated. Triflic acid (25.4 g, 169.5 mmol) was added at 70° C. After 3 hours, it was cooled to room temperature. D20 (30 ml) was mixed and stirred for 10 minutes. The mixture was neutralized with an aqueous $K_3PO_4$ solution, and the organic layer was extracted with ethyl acetate. After removing residual moisture using magnesium sulfate, the mixture was distilled under reduced pressure and separated by a column to obtain the compound Host3-4 (12 g, yield: 77.0%).

The green EML 230 can further include a dopant, e.g., an emitter, 236. In the green EML 230, a weight % of each of the first host 232 and the second host 234 can be greater than that of the dopant 236. The dopant 236 can be one of a phosphorescent compound, a fluorescent compound and a delayed fluorescent compound and can have a weight % of 3 weight % to 30 weight % in the green EML 230, preferably 5 weight % to 15 weight %.

The dopant 236 in the green EML 230 can be an iridium complex and can be represented by Formula 5.

[Formula 5]

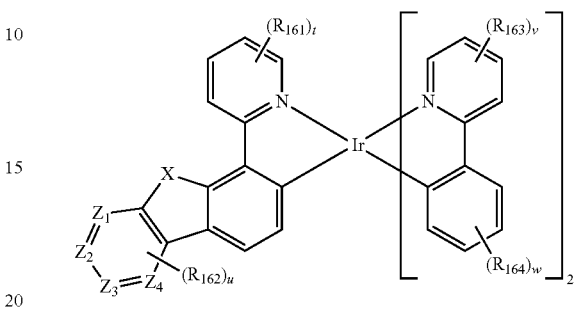

In Formula 5, each of $R_{161}$ to $R_{164}$ is independently selected from the group consisting of deuterium, halogen atom, C1 to C6 alkyl group, C3 to C6 cycloalkyl group, C6 to C10 aryl group and C3 to C10 heteroaryl group. Each oft, v and w is independently an integer of 0 to 4, and u is an integer of 0 to 3. X is oxygen atom or sulfur atom. Each of $Z_1$ to $Z_4$ is independently nitrogen or $CR_{165}$, and $R_{165}$ is selected from hydrogen, deuterium, halogen atom, C1 to C6 alkyl group. C3 to C6 cycloalkyl group, C6 to C10 aryl group and C3 to C10 heteroaryl group. (t, u, v and w are the number of substituents)

In the present disclosure, aryl group can be selected from the group consisting of phenyl group, biphenyl group, terphenyl group, naphthyl group, anthracenyl group, pentalenyl group, indenyl group, indenoindenyl group, heptalenyl group, biphenylenyl group, indacenyl group, phenalenyl group, phenanthrenyl group, benzophenanthrenyl group, dibenzophenanthrenyl group, azulenyl group, pyrenyl group, fluoranthenyl group, triphenylenyl group, chrysenyl group, tetraphenyl group, tetracenyl group, pleiadenyl group, picenyl group, pentaphenyl group, pentacenyl group, fluorenyl group, indenofluorenyl group, and spiro-fluorenyl group without specific definition. The above definition of the aryl group can be applied to arylene group, except that arylene group is a divalent group.

In the present disclosure, heteroaryl group can be selected from the group consisting of pyrrolyl group, pyridinyl group, pyrimidinyl group, pyrazinyl group, pyridazinyl group, triazinyl group, tetrazinyl group, imidazolyl group, pyrazolyl group, indolyl group, isoindolyl group, indazolyl group, indolizinyl group, pyrrolizinyl group, carbazolyl group, benzocarbazolyl group, dibenzocarbazolyl group, indolocarbazolyl group, indenocarbazolyl group, benzofurocarbazolyl group, benzothienocarbazolyl group, quinolinyl group, isoquinolinyl group, phthalazinyl group, quinoxalinyl group, cinnolinyl group, quinazolinyl group, quinolizinyl group, purinyl group, benzoquinolinyl group, benzoisoquinolinyl group, benzoquinazolinyl group, benzoquinoxalinyl group, acridinyl group, phenanthrolinyl group, perimidinyl group, phenanthridinyl group, pteridinyl group, cinnolinyl group, naphtharidinyl group, furanyl group, pyranyl group, oxazinyl group, oxazolyl group, oxadiazolyl group, triazolyl group, dioxinyl group, benzofuranyl group, dibenzofuranyl group, thiopyranyl group, xanthenyl group, chromaenyl group, isochromenyl group, thioazinyl group, thiophenyl group, benzothiophenyl group, dibenzothiophenyl group, difuropyrazinyl group, benzofurodibenzofuranyl group, benzothienobenzothiophenyl group, benzothienodibenzothiophenyl group, benzothienobenzofuranyl group, and benzothienodibenzofuranyl group without specific definition. The above definition of the heteroaryl group can be applied to heteroarylene group, except that heteroarylene group is a divalent group.

The dopant 236 in the green EML 230 can be one of the compounds in Formula 6.

[Formula 6]

S1
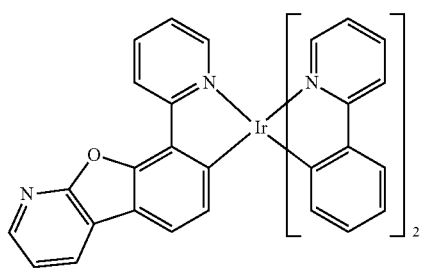

S2
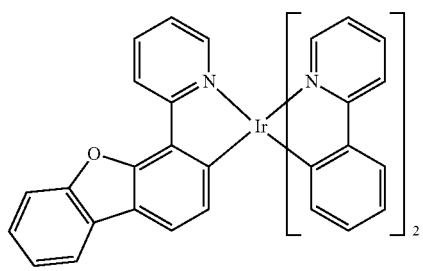

S3
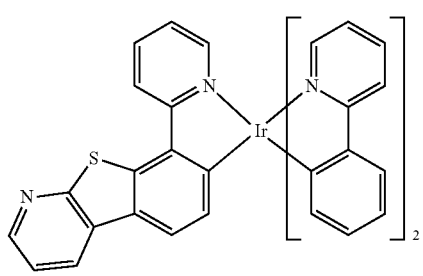

S4
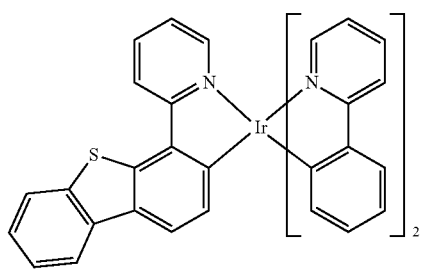

[Formula 7-1]

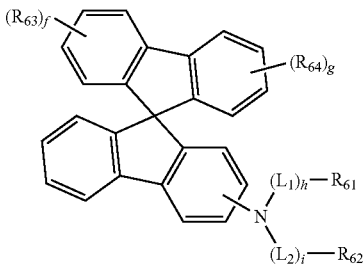

In Formula 7-1, each of $R_{61}$ and $R_{62}$ is independently selected from the group consisting of C6 to C30 aryl group and C3 to C30 heteroaryl group, and each of $R_{63}$ and $R_{64}$ is independently C1 to C20 alkyl group. Each of f and g is a number of substituent and is independently an integer of 0 to 4. Each of $L_1$ and $L_2$ is independently C6 to C30 arylene group, and each of h and i is 0 or 1.

For example, each of the aryl group, the heteroaryl group and the arylene group can be unsubstituted or substituted with at least one of C1 to C10 alkyl and C6 to C20 aryl.

For example, in Formula 7-1, each of $L_1$ and $L_2$ can be phenylene unsubstituted or substituted with C1 to C10 alkyl or C6 to C20 aryl. e.g., phenyl, and each of $R_{61}$ and $R_{62}$ can be independently selected from the group consisting of phenyl, naphthyl, fluorenyl, dibenzofuranyl and carbazolyl, each of which can be unsubstituted or substituted with C1 to C10 alkyl or C6 to C30 aryl, e.g., phenyl.

In Formula 7-1, f, g, h and i can be 0 (zero), $R_{61}$ can be biphenylyl, and $R_{62}$ can be dimethyl-substituted fluorenyl. Namely, the compound in Formula 7-1 can be represented by Formula 7-2.

[Formula 7-2]

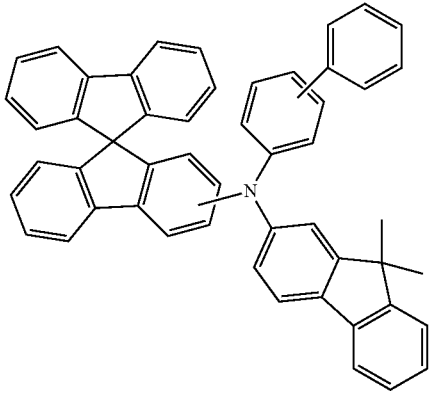

The HIL 210 can include a compound in Formula 7-1 as a hole injection material.

For example, the compound in Formula 7-1 can be one of the compounds in Formula 8, but it is not limited thereto.
[Formula 8]
E1
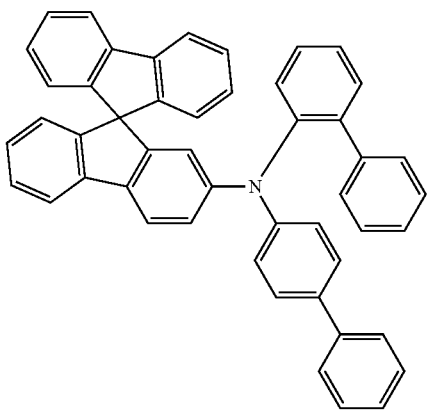
E2
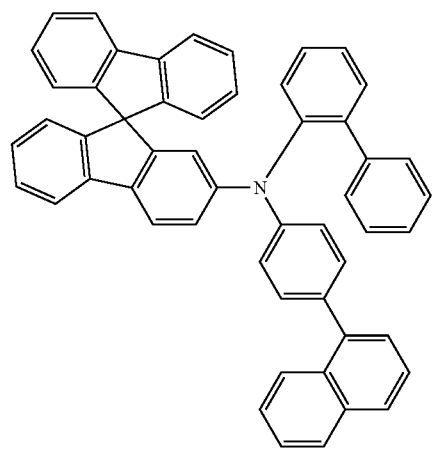
E3
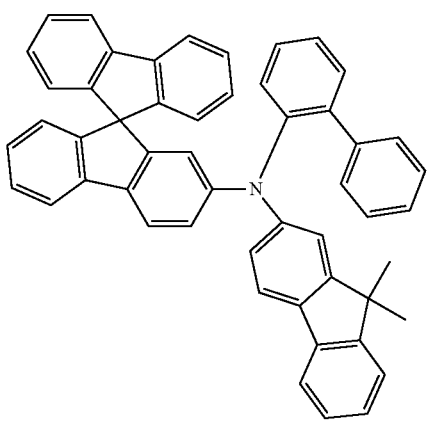
E4
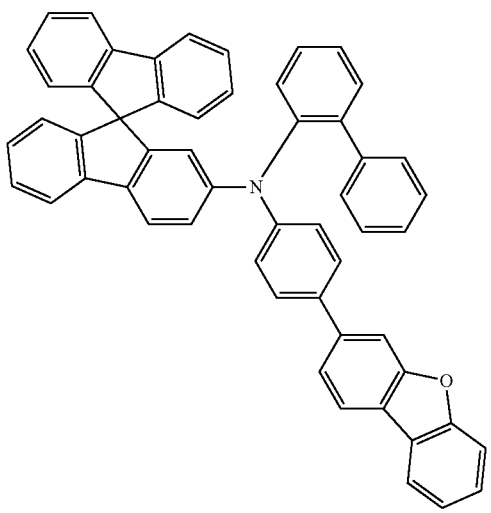
E5
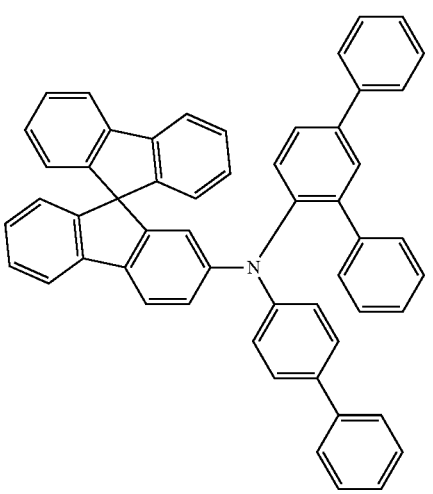
E6
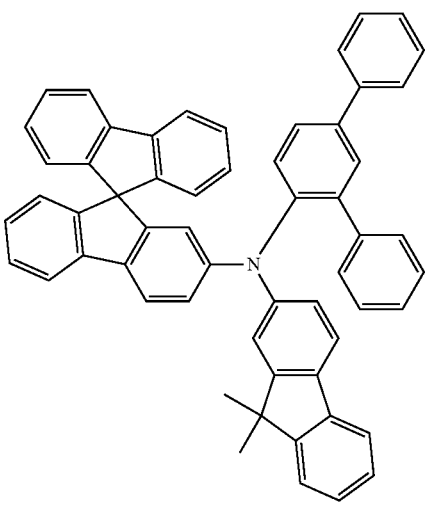

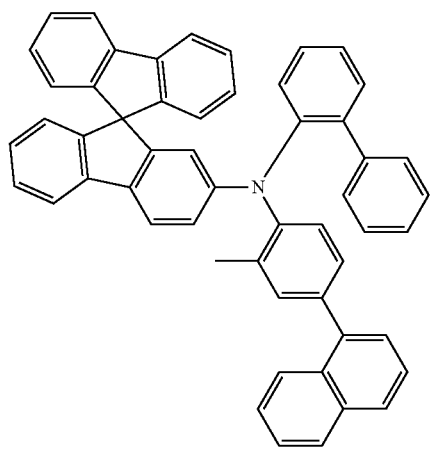
E7
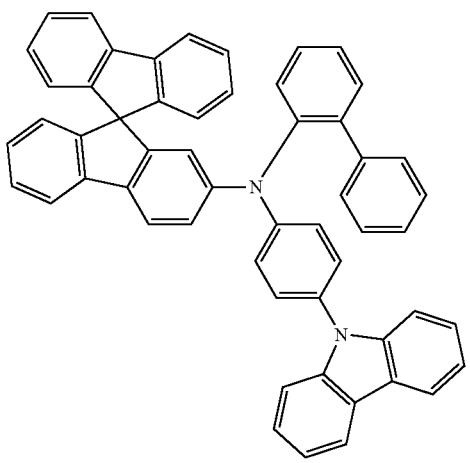
E10
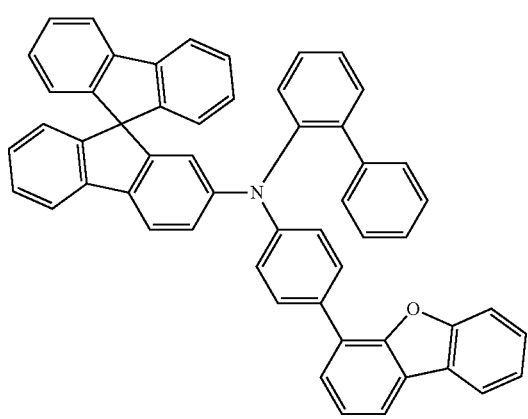
E8
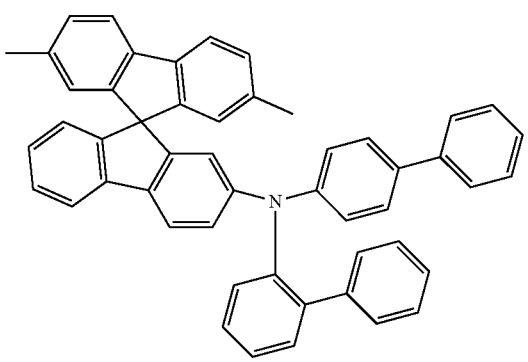
E11
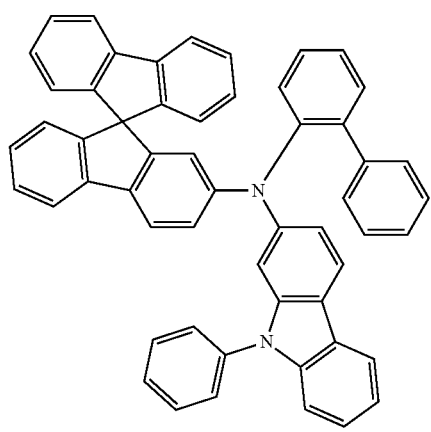
E9
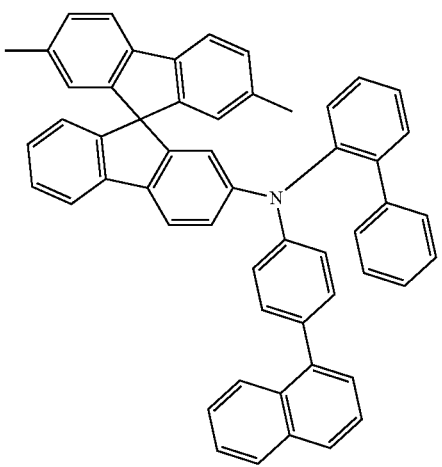
E12

E13
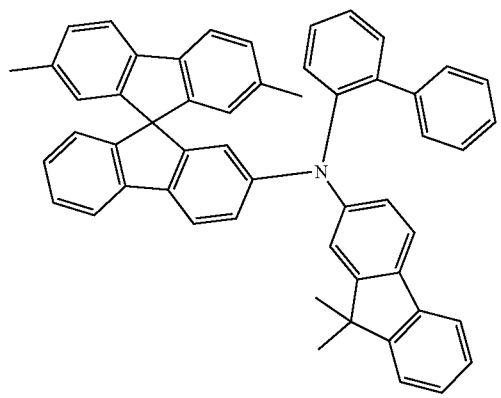
E14
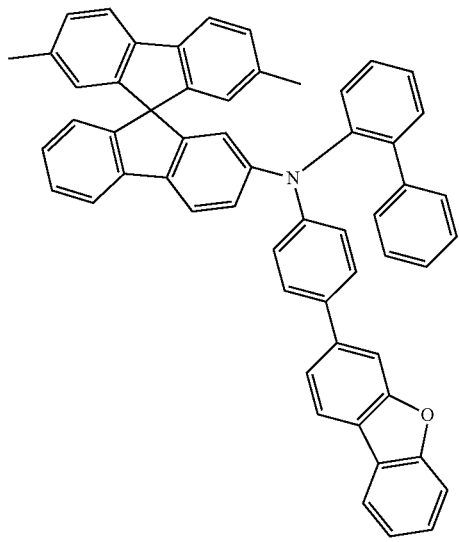
E15
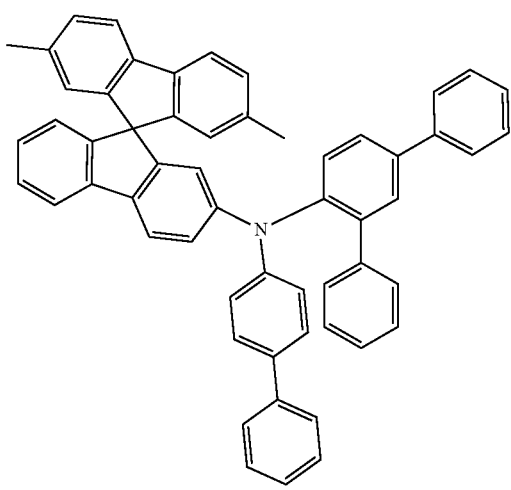
E16
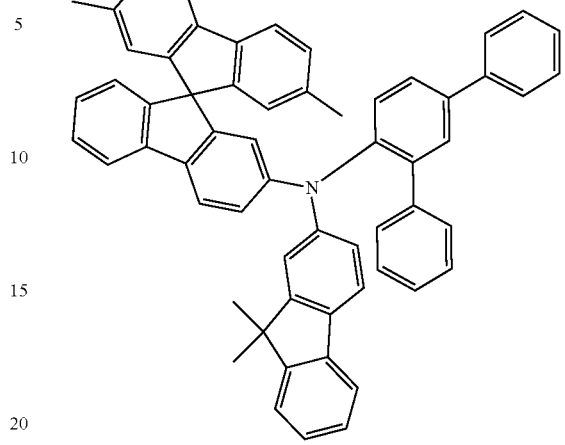
E17
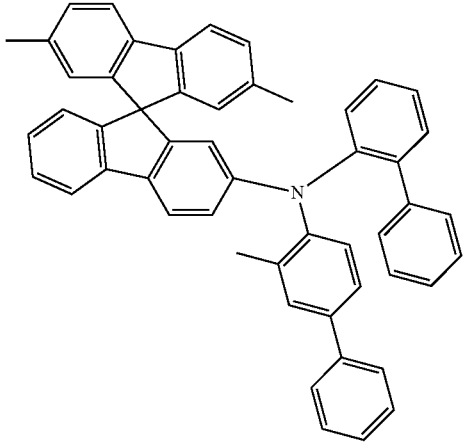
E18
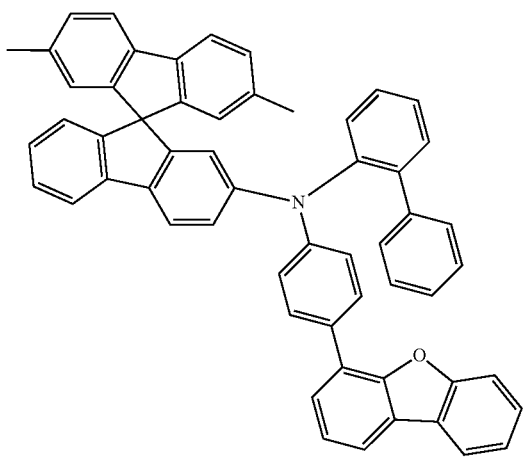

E19

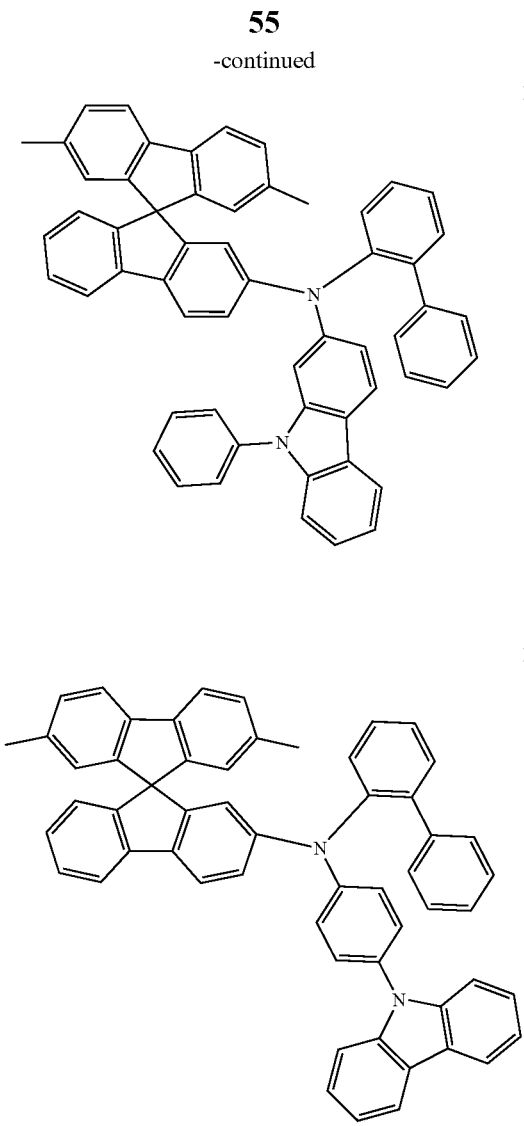

E20

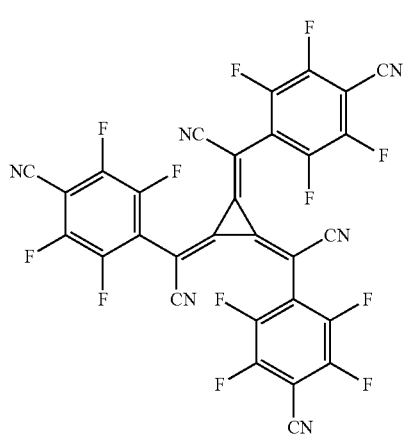

For example, the HIL 210 can further include a compound having a radialene structure in Formula 9 as a dopant, e.g., a p-type dopant.

[Formula 9]

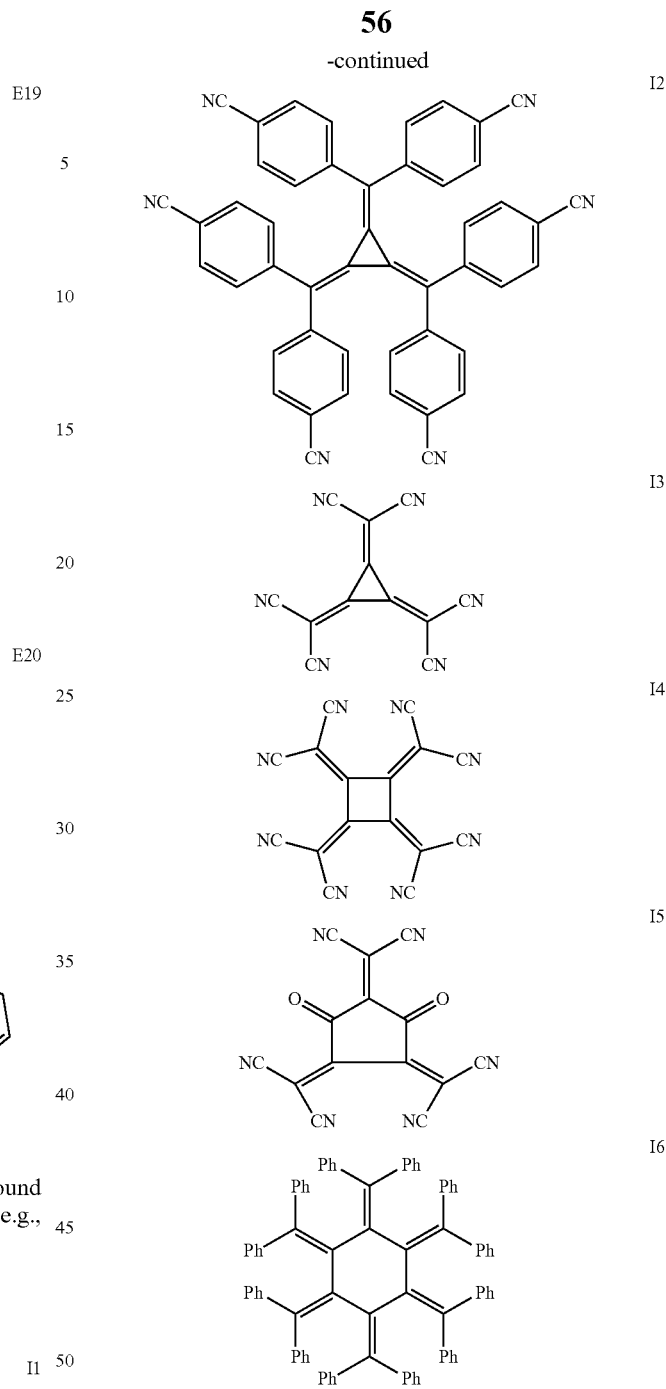

For example, in the HIL 210, the dopant can have a weight % of 0.1 weight % to 20 weight %, preferably 5 weight % to 15 weight %. The HIL 210 can have a thickness of 10 to 200 Å, preferably 30 to 100 Å.

The HTL 220 can include the compound in Formula 7-1 as a hole transporting material. For example, the HTL 220 can have a thickness of 50 to 400 Å, preferably 150 to 300 Å.

The hole injection material in the HIL 210 and the hole transporting material in the HTL 220 can be a compound having the same structure, e.g., the same compound. In this instance, the interfacial property between the HIL 210 and the HTL 220 is improved such that the emitting efficiency and the lifespan of the OLED can be further increased.

The ETL 240 can have a thickness of 50 to 400 Å. The ETL 240 can include a compound in Formula 10 as an electron transporting material, e.g., a first electron transporting material.

[Formula 10]

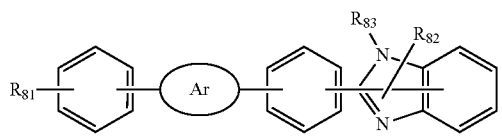

In Formula 10, Ar is C10 to C30 arylene group, and $R_{81}$ is C6 to C30 aryl group or C5 to C30 heteroaryl group, each of the C6 to C30 aryl group and the C5 to C30 heteroaryl group is optionally substituted with C1 to C10 alkyl group. Each of $R_{82}$ and $R_{83}$ is independently hydrogen, C1 to C10 alkyl group or C6 to C30 aryl group.

In Formula 10, Ar can be naphthylene or anthracenylene, and $R_{81}$ can be phenyl unsubstituted or substituted with C1 to C10 alkyl, or benzimidazole group. $R_{82}$ can be methyl, ethyl or phenyl, and $R_{83}$ can be hydrogen, a methyl group or a phenyl group.

For example, the compound in Formula 10 can be one of the compounds in Formula 11.

[Formula 11]

G1
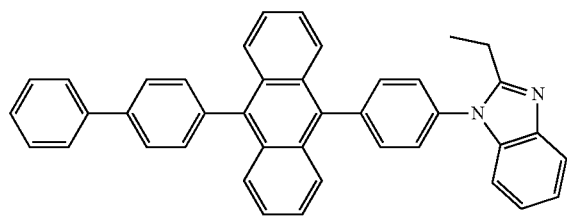

G2
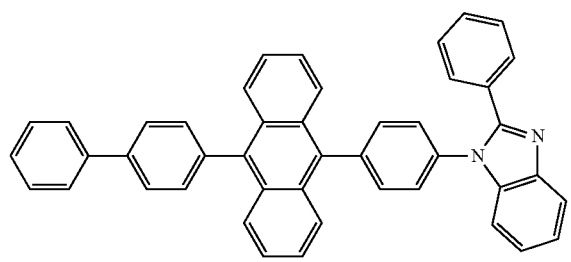

G3
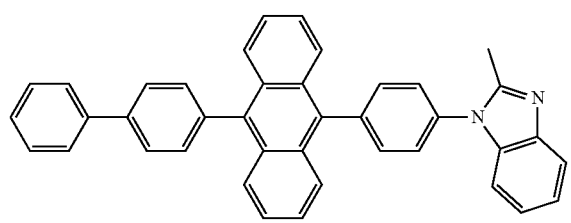

-continued

G4
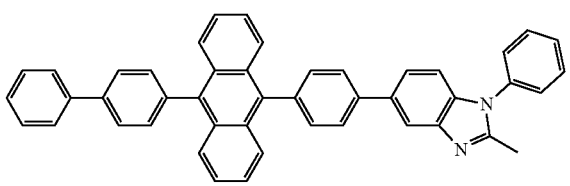

G5
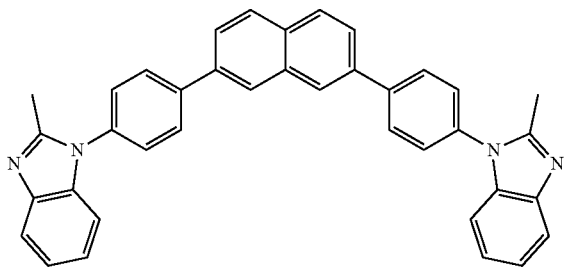

G6
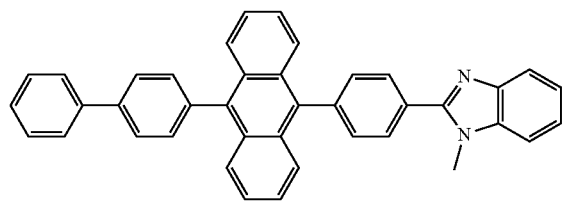

Alternatively, the ETL 240 can include a compound in Formula 12 as an electron transporting material, e.g., a second electron transporting material.

[Formula 12]

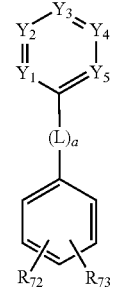

In Formula 12, each of $Y_1$ to $Y_5$ is independently $CR_{71}$ or nitrogen atom (N), and one to three of $Y_1$ to $Y_5$ is N. $R_{71}$ is hydrogen or C6 to C30 aryl group, and L is C6 to C30 arylene group. Each of $R_{72}$ and $R_{73}$ is independently selected from the group consisting of hydrogen, and C5 to C30 heteroaryl group, and at least one of $R_{72}$ and $R_{73}$ is C5 to C30 heteroaryl group. In addition, a is 0 or 1.

In Formula 12, one or two of $Y_1$ to $Y_5$ can be N. The heteroaryl group for $R_{72}$ and $R_{73}$ can be carbazolyl, and L can be phenylene.

For example, the compound in Formula 12 can be one of the compounds in Formula 13.

[Formula 13]
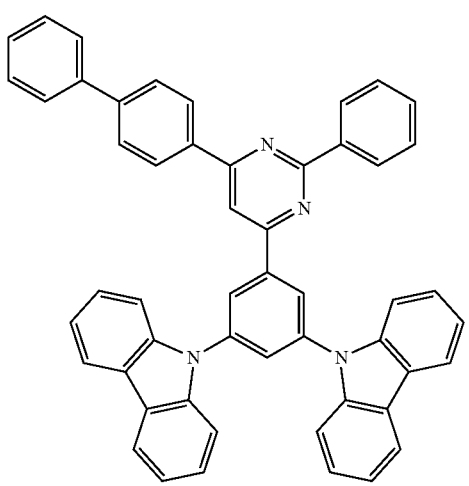
F1
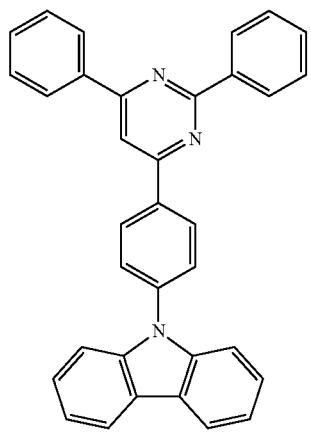
F4
F2
F5
F3
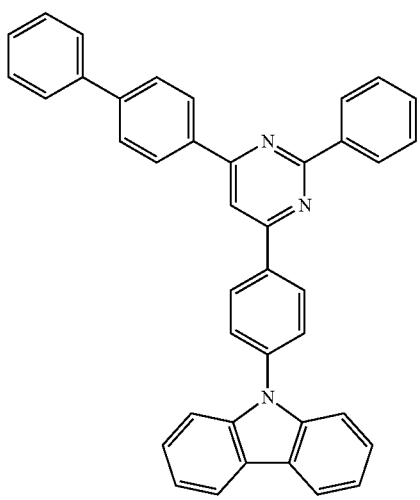
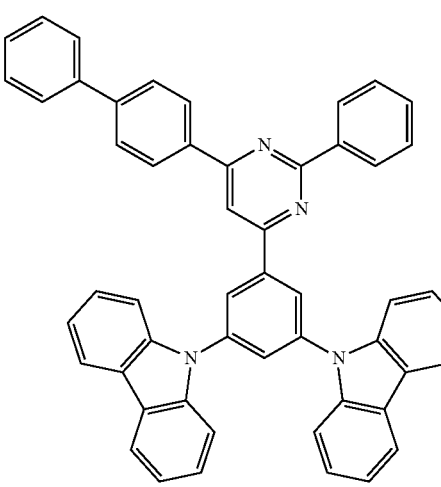
F6

F7
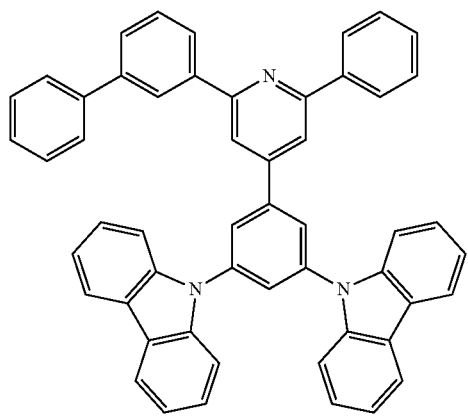
F8
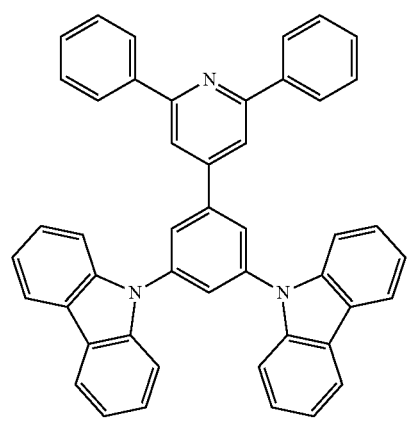
F9
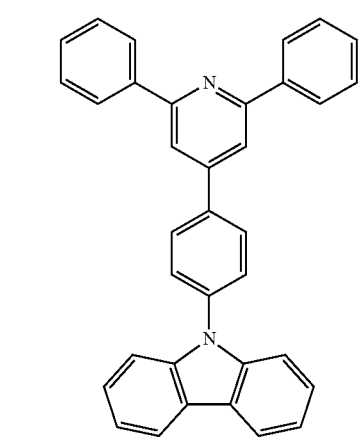
F10
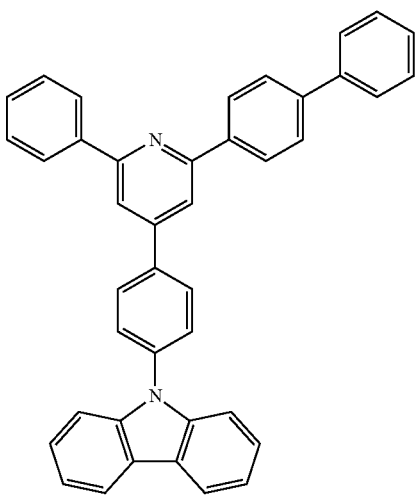
F11
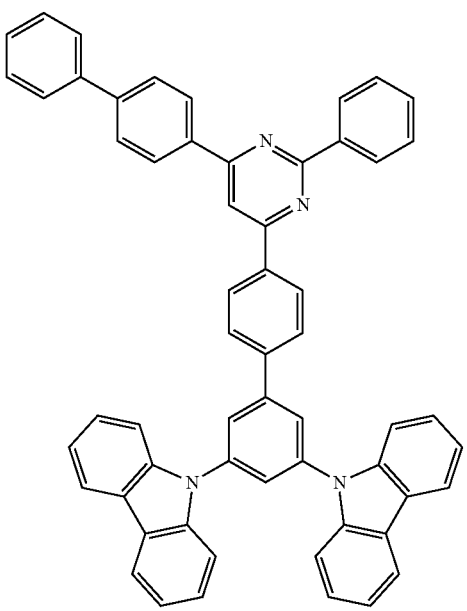
F12
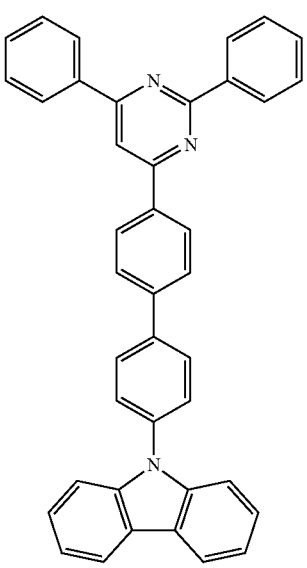

-continued

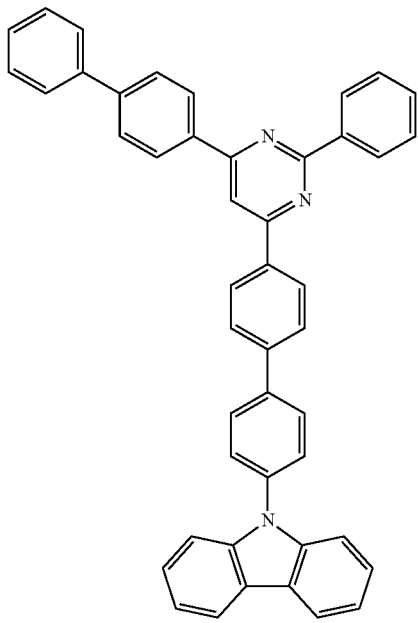

F13

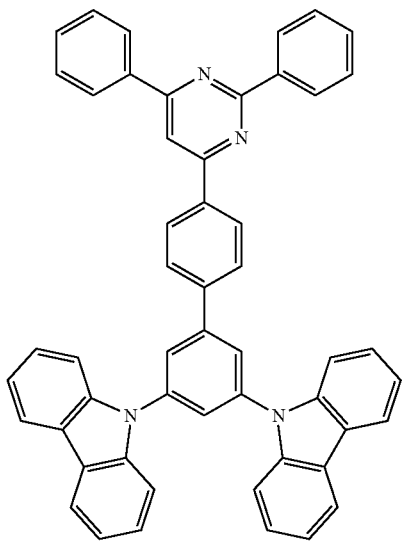

F14

[Formula 14]

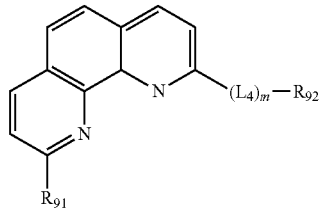

In Formula 14, $R_{91}$ is hydrogen or C6 to C30 aryl group, and $R_{92}$ is C6 to C30 aryl group or C5 to C30 heteroaryl group. The C6 to C30 aryl group or C5 to C30 heteroaryl group can be unsubstituted or substituted. $L_4$ is C6 to C30 arylene group or C5 to C30 heteroarylene group, and m is 1 or 2.

In this instance, the aryl group, the arylene group and the heteroarylene group can be unsubstituted or substituted with C1 to C10 alkyl.

For example, in Formula 14, $R_{91}$ can be hydrogen, phenyl unsubstituted or substituted with methyl, or naphthyl unsubstituted or substituted with methyl, and $R_{92}$ can be phenyl unsubstituted or substituted with methyl, naphthyl unsubstituted or substituted with methyl or phenanthrenyl unsubstituted or substituted with methyl. $L_4$ can be phenylene, naphthylene, anthracenylene or phenanthrenylene.

The compound in Formula 14 can be one of the compounds in Formula 15.

[Formula 15]

H1

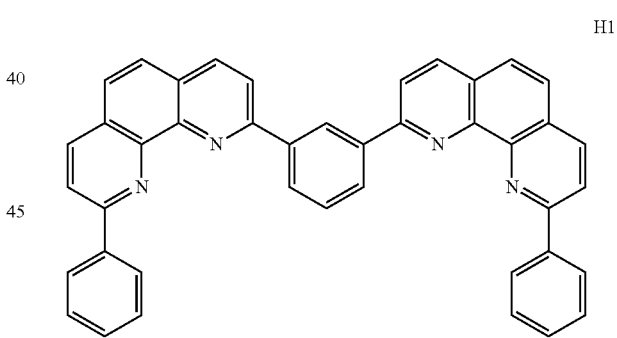

H2

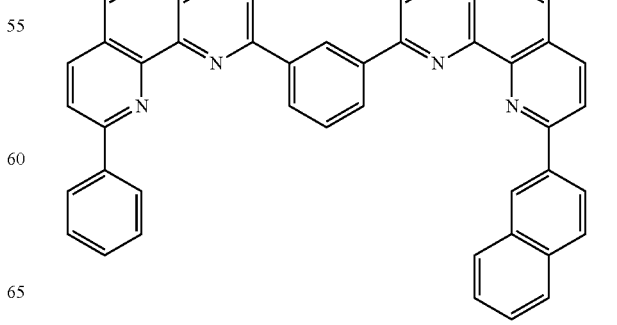

The ETL 240 can include both the compound in Formula 10 and the compound in Formula 12. In this instance, the compound in Formula 10 and the compound in Formula 12 can have the same weight %.

The EIL 250 can have a thickness of 10 to 400 Å, preferably 100 to 300 Å.

The EIL 250 can include a compound in Formula 14 as an electron injection material.

H3

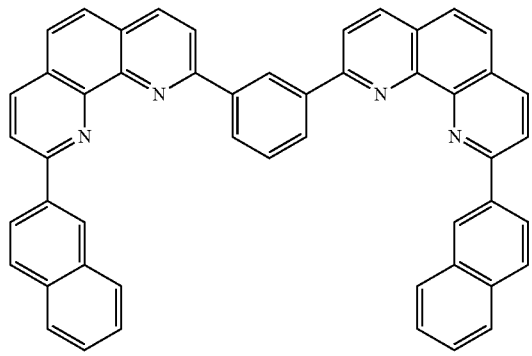

H4

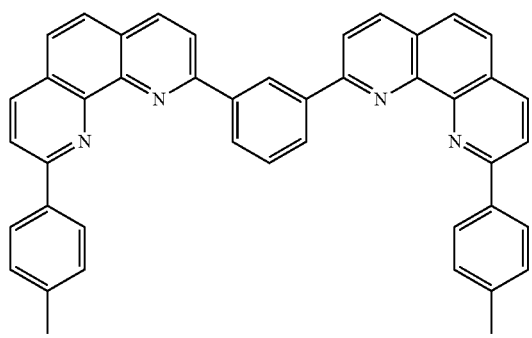

H5

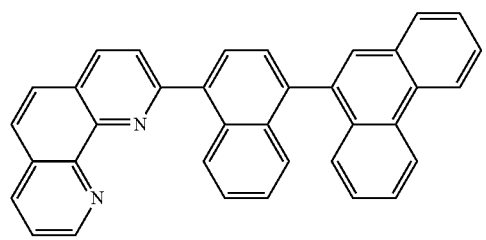

H6

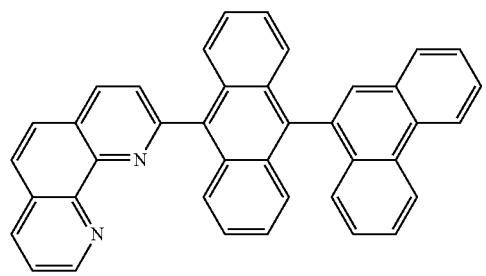

H7

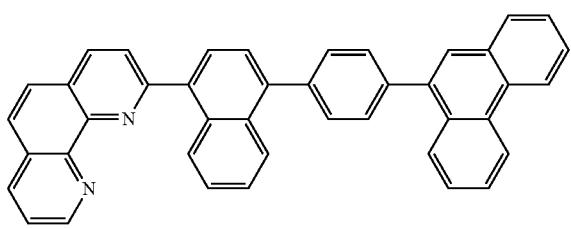

H8

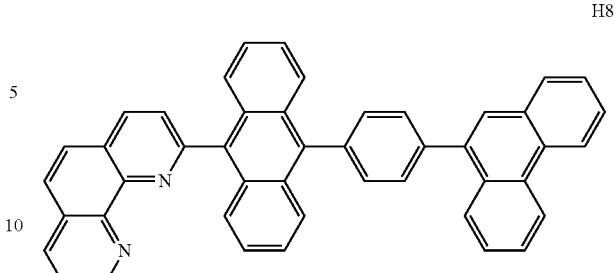

The EIL 250 can further include a dopant being one of alkali metal, e.g., Li, Na, K or Cs, and alkali earth metal, e.g., Mg, Sr, Ba or Ra. In this instance, the electron injection property of the EIL 250 can be improved. In the EIL 250, the dopant can have a weight % of 0.1 weight % to 10 weight %, preferably 0.5 weight % to 5 weight %.

The EBL can include at least one of tris(4-carbazoyl-9-yl-phenyl)amine (TCTA), tris[4-(diethylamino)phenyl]amine, N-(biphenyl-4-yl)-9,9-dimethyl-N-(4-(9-phenyl-9H-carbazol-3-yl)phenyl)-9H-fluoren-2-amine, TAPC, 4,4',4"-tris(3-methylphenylamino)triphenylamine (MTDATA), 1,3-bis(carbazol-9-yl)benzene (mCP), 3,3'-bis(N-carbazolyl)-1,1'-biphenyl (mCBP), copper phthalocyanine (CuPc), N,N'-bis[4-[bis(3-methylphenyl)amino]phenyl]-N,N'-diphenyl-[1,1'-biphenyl]-4,4'-diamine (DNTPD), 1,3,5-tris[4-(diphenylamino)phenyl]benzene (TDAPB), DCDPA, and 2,8-bis(9-phenyl-9H-carbazol-3-yl)dibenzo[b,d]thiophene), but it is not limited thereto. For example, the EBL can have a thickness of 10 to 350 Å, preferably 100 to 200 Å.

Alternatively, the EBL can include a compound in Formula 16 as an electron blocking material

[Formula 16]

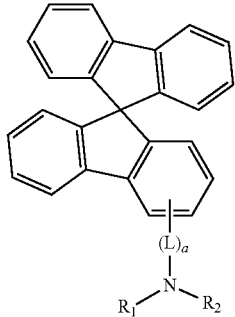

In Formula 16, L is C6 to C30 arylene group, and a is 0 or 1. Each of $R_1$ and $R_2$ is independently selected from the group consisting of C6 to C30 aryl group and C5 to C30 heteroaryl group, wherein each of the C6 to C30 aryl group and C5 to C30 heteroaryl group is optionally substituted with at least one of C1 to C10 alkyl group and C6 to C30 aryl group, respectively.

For example, L can be phenylene, and each of $R_1$ and $R_2$ can be independently selected from the group consisting of biphenyl, dimethyl-substituted fluorenyl, phenylcarbazolyl, carbazolylphenyl, dibenzothiophenyl and dibenzofuranyl.

Namely, the electron blocking material in Formula 16 is an amine derivative substituted with spirofluorene (e.g., spirofluorene-substituted amine derivative).

The electron blocking material in Formula 16 can be one of the compounds in Formula 17.
[Formula 17]
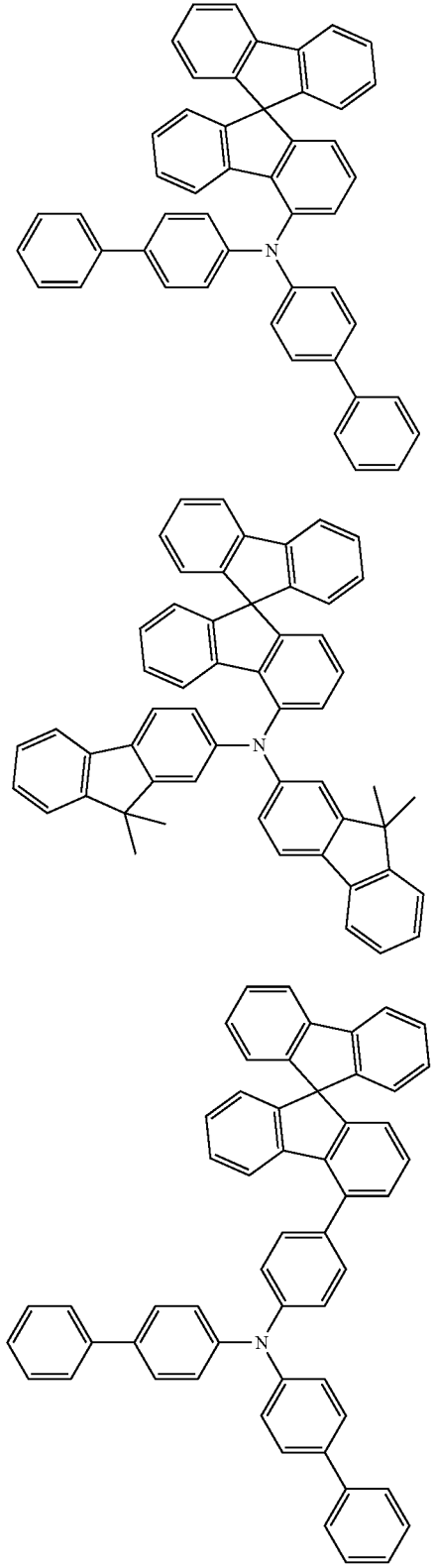

H6 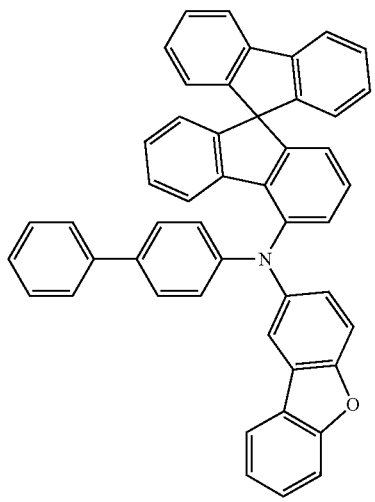

H7 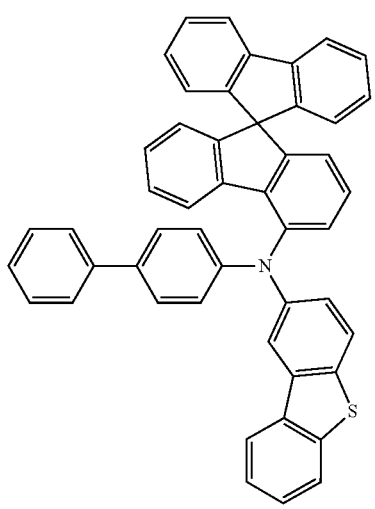

H8 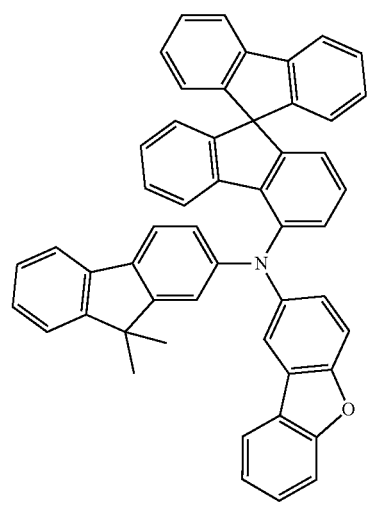

H9 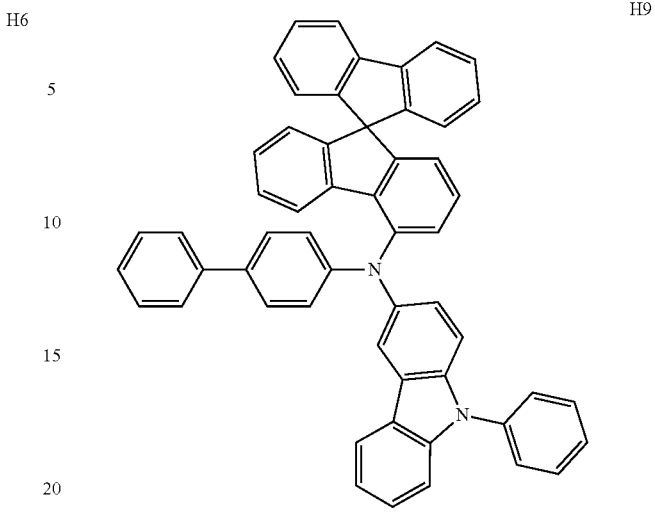

The HBL can include at least one of tris-(8-hydroxyquinoline) aluminum (Alq$_3$), 2-biphenyl-4-yl-5-(4-t-butylphenyl)-1,3,4-oxadiazole (PBD), spiro-PBD, lithium quinolate (Liq), 2,2',2"-(1,3,5-Benzenetriyl)-tris(1-phenyl-1-H benzimidazole) (TPBi), bis(2-methyl-8-quinolinolato-N1,O8)-(1, 1'-biphenyl-4-olato)aluminum (BAlq), 4,7-diphenyl-1,10-phenanthroline (Bphen), 2,9-bis(naphthalene-2-yl)4,7-diphenyl-1,10-phenanthroline (NBphen), 2,9-dimethyl-4,7-diphenyl-1,10-phenathroline (BCP), 3-(4-biphenyl)-4-phenyl-5-tert-butylphenyl-1,2,4-triazole (TAZ), 4-(naphthalen-1-yl)-3,5-diphenyl-4H-1,2,4-triazole (NTAZ), 1,3,5-tri(p-pyrid-3-yl-phenyl)benzene (TpPVPB), 2,4,6-tris(3'-(pyridin-3-yl)biphenyl-3-yl)1,3,5-triazine (TmPPPyTz), Poly[9,9-bis(3'-((N,N-dimethyl)-N-ethylammonium)-propyl)-2,7-fluorene-alt-2,7-(9,9-dioctylfluorene)] (PFNBr), tris(phenylquinoxaline) (TPQ), and diphenyl-4-triphenylsilyl-phenylphosphine oxide (TSPO1), but it is not limited thereto. For example, the HBL can have a thickness of 10 to 350 Å, preferably 100 to 200 Å.

As described above, in the OLED D disposed in the green pixel region, the green EML 230 includes the first host 232 having a fused-hetero ring moiety and a second host 234 having a biscarbazole moiety, and at least one of the fused-hetero ring moiety of the first host 232 and the biscarbazole moiety of the second host 234 is partially or wholly deuterated. As a result, the lifespan of the OLED D and the organic light emitting display device 100 including the OLED D is significantly increased.

In addition, when only the fused-hetero ring moiety in the first host 232 is deuterated and/or only the biscarbazole moiety in the second host 234 is deuterated, the emitting efficiency and the lifespan of the OLED D and the organic light emitting display device 100 are further improved.

[Organic Light Emitting Diode]

On the anode (ITO), the HIL (the compound E3 in Formula 8 and the compound 11 in Formula 9 (10 wt %), 50 Å), the HTL (the compound E3 in Formula 8, 250 Å), the green EML (a first host, a second host and a dopant (the compound S1 in Formula 6, 12 wt %), 300 Å), the ETL (the compound G1 in Formula 11, 200 Å), the EIL (the compound H1 in Formula 15 and L$_1$ (2 wt %), 200 Å), and the cathode (AgMg (weight ratio=10:1)) was sequentially deposited. An encapsulation film is formed by using an UV curable epoxy and a moisture getter to form the OLED.

1. Comparative Example

(1) Comparative Example 1 (Ref1)

In the green EML, the compound Host1-1 in Formula 3 and the compound Host3-1 in Formula 4 are used as the first host and the second host, respectively. (the first host:the second host=3:7 (weight ratio))

(2) Comparative Example 2 (Ref2)

In the green EML, the compound Host2-1 in Formula 3 and the compound Host3-1 in Formula 4 are used as the first host and the second host, respectively. (the first host:the second host=3:7 (weight ratio))

2. Example

(1) Examples 1 to 4 (Ex1 to Ex4)

In the green EML, the compound Host3-1 in Formula 4 is used as the second host, and the compounds Host1-2, Host1-3, Host1-4 and Host1-5 in Formula 3 are used as the first host. (the first host:the second host=3:7 (weight ratio))

(2) Examples 5 to 8 (Ex5 to Ex8)

In the green EML, the compound Host3-1 in Formula 4 is used as the second host, and the compounds Host2-2, Host2-3, Host2-4 and Host2-5 in Formula 3 are used as the first host. (the first host:the second host=3:7 (weight ratio))

(3) Examples 9 to 13 (Ex9 to Ex13)

In the green EML, the compound Host3-2 in Formula 4 is used as the second host, and the compounds Host1-1, Host1-2, Host1-3, Host1-4 and Host1-5 in Formula 3 are used as the first host. (the first host:the second host=3:7 (weight ratio))

(4) Examples 14 to 18 (Ex14 to Ex18)

In the green EML, the compound Host3-2 in Formula 4 is used as the second host, and the compounds Host2-1, Host2-2, Host2-3, Host2-4 and Host2-5 in Formula 3 are used as the first host. (the first host:the second host=3:7 (weight ratio))

(5) Examples 19 to 23 (Ex19 to Ex23)

In the green EML, the compound Host3-3 in Formula 4 is used as the second host, and the compounds Host1-1, Host1-2, Host1-3, Host1-4 and Host1-5 in Formula 3 are used as the first host. (the first host:the second host=3:7 (weight ratio))

(6) Examples 24 to 28 (Ex24 to Ex28)

In the green EML, the compound Host3-3 in Formula 4 is used as the second host, and the compounds Host2-1, Host2-2, Host2-3, Host2-4 and Host2-5 in Formula 3 are used as the first host. (the first host:the second host=3:7 (weight ratio))

(7) Examples 29 to 33 (Ex29 to Ex33)

In the green EML, the compound Host3-4 in Formula 4 is used as the second host, and the compounds Host1-1, Host1-2, Host1-3, Host1-4 and Host1-5 in Formula 3 are used as the first host. (the first host:the second host=3:7 (weight ratio))

(8) Examples 34 to 38 (Ex34 to Ex38)

In the green EML, the compound Host3-4 in Formula 4 is used as the second host, and the compounds Host2-1, Host2-2, Host2-3, Host2-4 and Host2-5 in Formula 3 are used as the first host. (the first host:the second host=3:7 (weight ratio))

The properties, e.g., the driving voltage (V), the efficiency (cd/A), the lifespan (hr) and the color coordinate, of the OLED of Ref1 and Ref2 and Ex1 to Ex38 are measured and listed in Tables 1 to 3. The driving voltage and the efficiency were measured at a current density of 10 mA/cm$^2$, and the lifespan is the time until a luminance of 95% of the initial luminance is achieved at a current density of 22.5 mA/cm$^2$ and a temperature condition of 40° C.

TABLE 1

| | G-EML | | | | lifespan | | |
|---|---|---|---|---|---|---|---|
| | Host 2 | Host 1 | V | cd/A | (hr) | CIEx | CIEy |
| Ref 1 | Host 3-1 | Host 1-1 | 3.15 | 79.01 | 145 | 0.356 | 0.619 |
| Ex 1 | Host 3-1 | Host 1-2 | 3.15 | 79.01 | 160 | 0.356 | 0.619 |
| Ex 2 | Host 3-1 | Host 1-3 | 3.15 | 79.01 | 161 | 0.356 | 0.619 |
| Ex 3 | Host 3-1 | Host 1-4 | 3.15 | 78.93 | 189 | 0.356 | 0.619 |
| Ex 4 | Host 3-1 | Host 1-5 | 3.15 | 78.85 | 184 | 0.356 | 0.619 |
| Ref 2 | Host 3-1 | Host 2-1 | 3.45 | 75.06 | 138 | 0.356 | 0.619 |
| Ex 5 | Host 3-1 | Host 2-2 | 3.45 | 74.98 | 152 | 0.356 | 0.619 |
| Ex 6 | Host 3-1 | Host 2-3 | 3.45 | 74.98 | 152 | 0.356 | 0.619 |
| Ex 7 | Host 3-1 | Host 2-4 | 3.45 | 74.98 | 181 | 0.356 | 0.619 |
| Ex 8 | Host 3-1 | Host 2-5 | 3.45 | 74.98 | 177 | 0.356 | 0.619 |
| Ex 9 | Host 3-2 | Host 1-1 | 3.15 | 79.01 | 167 | 0.356 | 0.619 |
| Ex 10 | Host 3-2 | Host 1-2 | 3.15 | 79.01 | 184 | 0.356 | 0.619 |
| Ex 11 | Host 3-2 | Host 1-3 | 3.15 | 79.01 | 184 | 0.356 | 0.619 |
| Ex 12 | Host 3-2 | Host 1-4 | 3.15 | 78.93 | 217 | 0.356 | 0.619 |
| Ex 13 | Host 3-2 | Host 1-5 | 3.15 | 78.85 | 207 | 0.356 | 0.619 |

TABLE 2

| | G-EML | | | | lifespan | | |
|---|---|---|---|---|---|---|---|
| | Host 2 | Host 1 | V | cd/A | (hr) | CIEx | CIEy |
| Ex 14 | Host 3-2 | Host 2-1 | 3.45 | 75.06 | 159 | 0.356 | 0.619 |
| Ex 15 | Host 3-2 | Host 2-2 | 3.45 | 74.98 | 173 | 0.356 | 0.619 |
| Ex 16 | Host 3-2 | Host 2-3 | 3.45 | 74.98 | 174 | 0.356 | 0.619 |
| Ex 17 | Host 3-2 | Host 2-4 | 3.45 | 74.98 | 209 | 0.356 | 0.619 |
| Ex 18 | Host 3-2 | Host 2-5 | 3.45 | 74.98 | 202 | 0.356 | 0.619 |
| Ex 19 | Host 3-3 | Host 1-1 | 3.15 | 79.01 | 175 | 0.356 | 0.619 |
| Ex 20 | Host 3-3 | Host 1-2 | 3.15 | 79.01 | 191 | 0.356 | 0.619 |
| Ex 21 | Host 3-3 | Host 1-3 | 3.15 | 79.01 | 191 | 0.356 | 0.619 |
| Ex 22 | Host 3-3 | Host 1-4 | 3.15 | 78.93 | 225 | 0.356 | 0.619 |
| Ex 23 | Host 3-3 | Host 1-5 | 3.15 | 78.85 | 216 | 0.356 | 0.619 |
| Ex 24 | Host 3-3 | Host 2-1 | 3.45 | 75.06 | 165 | 0.356 | 0.619 |
| Ex 25 | Host 3-3 | Host 2-2 | 3.45 | 74.98 | 181 | 0.356 | 0.619 |
| Ex 26 | Host 3-3 | Host 2-3 | 3.45 | 74.98 | 181 | 0.356 | 0.619 |
| Ex 27 | Host 3-3 | Host 2-4 | 3.45 | 74.98 | 218 | 0.356 | 0.619 |
| Ex 28 | Host 3-3 | Host 2-5 | 3.45 | 74.98 | 210 | 0.356 | 0.619 |

TABLE 3

| | G-EML | | | | lifespan | | |
|---|---|---|---|---|---|---|---|
| | Host 2 | Host 1 | V | cd/A | (hr) | CIEx | CIEy |
| Ex 29 | Host 3-4 | Host 1-1 | 3.15 | 79.01 | 189 | 0.356 | 0.619 |
| Ex 30 | Host 3-4 | Host 1-2 | 3.15 | 79.01 | 206 | 0.356 | 0.619 |

TABLE 3-continued

| | G-EML | | | | lifespan | | |
|---|---|---|---|---|---|---|---|
| | Host 2 | Host 1 | V | cd/A | (hr) | CIEx | CIEy |
| Ex 31 | Host 3-4 | Host 1-3 | 3.15 | 79.01 | 207 | 0.356 | 0.619 |
| Ex 32 | Host 3-4 | Host 1-4 | 3.15 | 78.93 | 247 | 0.356 | 0.619 |
| Ex 33 | Host 3-4 | Host 1-5 | 3.15 | 78.85 | 235 | 0.356 | 0.619 |
| Ex 34 | Host 3-4 | Host 2-1 | 3.45 | 75.06 | 178 | 0.356 | 0.619 |
| Ex 35 | Host 3-4 | Host 2-2 | 3.45 | 74.98 | 197 | 0.356 | 0.619 |
| Ex 36 | Host 3-4 | Host 2-3 | 3.45 | 74.98 | 197 | 0.356 | 0.619 |
| Ex 37 | Host 3-4 | Host 2-4 | 3.45 | 74.98 | 236 | 0.356 | 0.619 |
| Ex 38 | Host 3-4 | Host 2-5 | 3.45 | 74.98 | 231 | 0.356 | 0.619 |

As shown in Tables 1 to 3, in comparison to the OLED of Ref1 and Ref2, in which the first and second hosts are not deuterated, the lifespan of the OLED of Ex1 to Ex38, in which at least one of the first and second hosts is deuterated, is significantly increased.

In addition, in the OLED of Ex3, Ex7, Ex12, Ex17. Ex22, Ex27, Ex32 and Ex37, in which the fused-hetero ring moiety of the first host is deuterated, and Ex19 to Ex28, in which the biscarbazole moiety of the second host is deuterated, the lifespan is further increased.

Namely, in comparison to the OLED using the first host, i.e., the compounds Host1-2, Host1-3, Host2-2 and Host2-3, in which the phenylene linker and/or the triazine moiety except the fused-hetero ring moiety is deuterated, the lifespan of the OLED using the first host, i.e., the compounds Host1-4 and Host2-4, in which only the fused-hetero ring moiety is deuterated, is improved. In addition, in comparison to the OLED using the second host, i.e., the compound Host3-2, in which the biphenyl moiety except the biscarbazole moiety is deuterated, the lifespan of the OLED using the second host, i.e., the compound Host3-3, in which only the biscarbazole moiety is deuterated, is improved.

Moreover, in comparison to the OLED using the first host, i.e., the compounds Host1-5 and Host2-5, which is wholly deuterated, the lifespan of the OLED using the first host, i.e., the compounds Host1-4 and Host2-4, in which only the fused-hetero ring moiety is deuterated, is improved. Accordingly, without additional increase of the production cost by the deuterium atom, the OLED has an advantage of increase of the lifespan.

Figure 4:
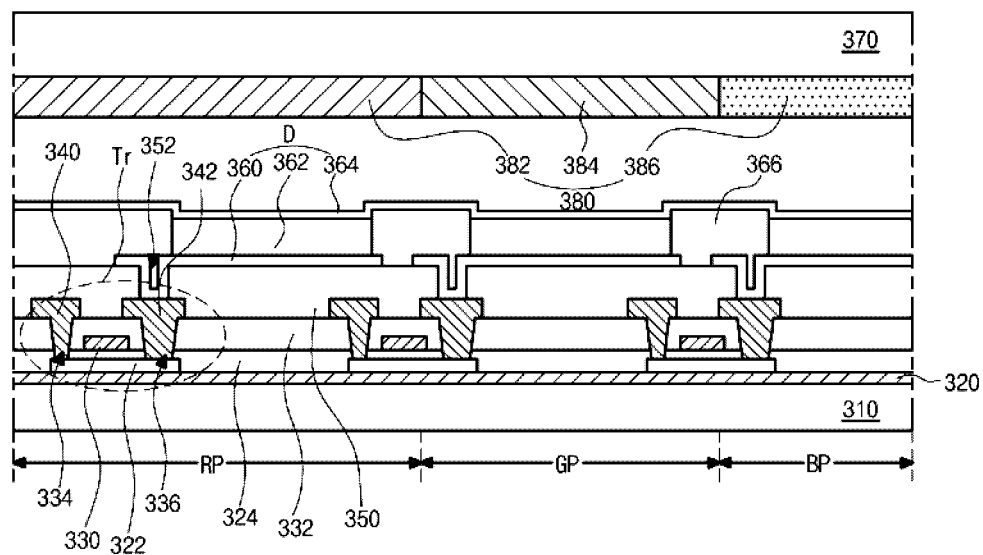
FIG. 4 is a schematic cross-sectional view illustrating an organic light emitting display device according to a third embodiment of the present disclosure.
Figure 5:
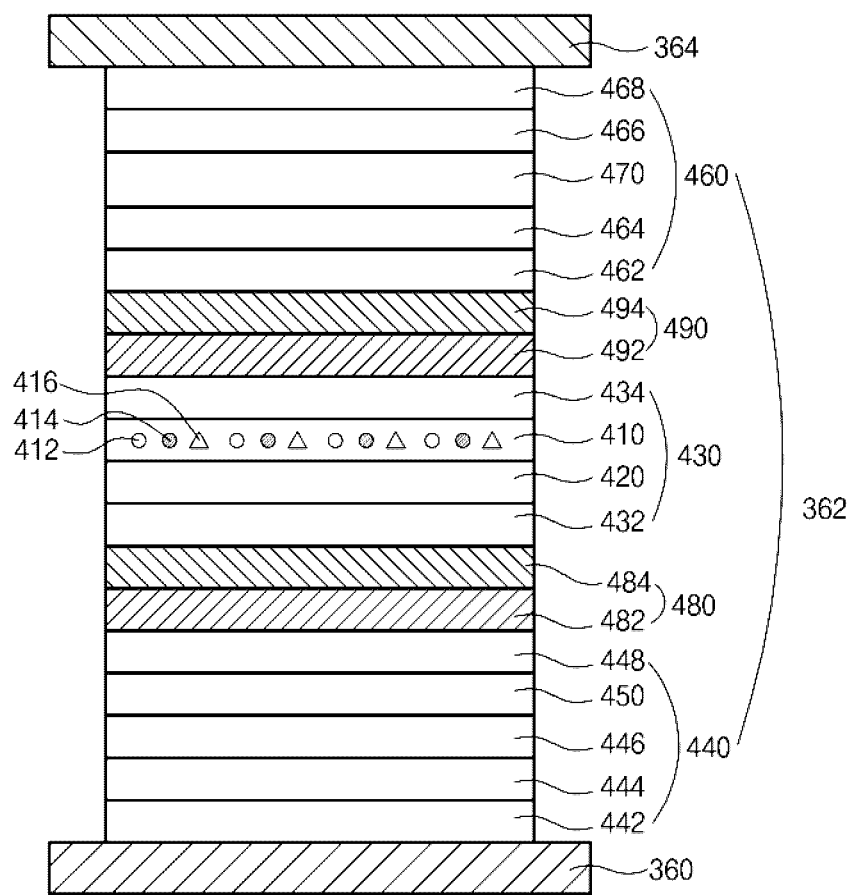
FIG. 5 is a schematic cross-sectional view illustrating an OLED according to a fourth embodiment of the present disclosure.
Figure 6:
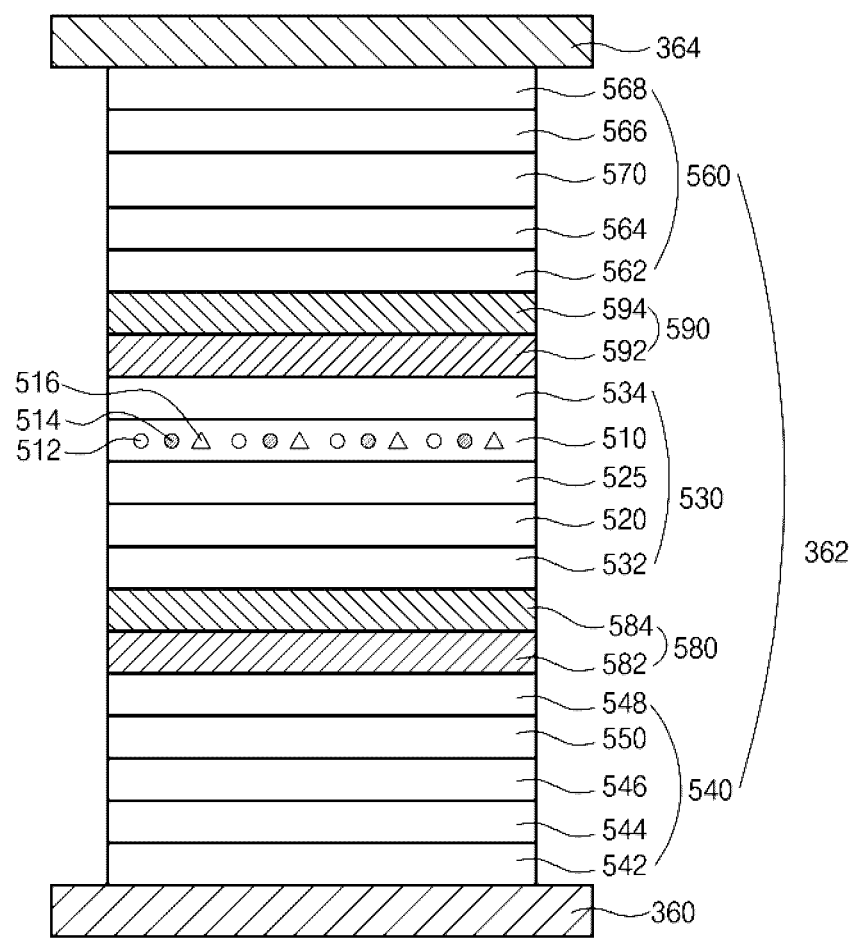
FIG. 6 is a schematic cross-sectional view illustrating an OLED according to a fifth embodiment.

FIG. 4 is a schematic cross-sectional view illustrating an organic light emitting display device according to a third embodiment of the present disclosure. FIG. 5 is a schematic cross-sectional view illustrating an OLED according to a fourth embodiment of the present disclosure, and FIG. 6 is a schematic cross-sectional view illustrating an OLED according to a fifth embodiment.

As shown in FIG. 4, the organic light emitting display device 300 includes a first substrate 310, where a red pixel region RP, a green pixel region GP and a blue pixel region BP are defined, a second substrate 370 facing the first substrate 310, an OLED D, which is positioned between the first and second substrates 310 and 370 and providing white emission, and a color filter layer 380 between the OLED D and the second substrate 370.

Each of the first and second substrates 310 and 370 can be a glass substrate or a flexible substrate. For example, the flexible substrate can be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 320 is formed on the first substrate 310, and the TFT Tr corresponding to each of the red, green and blue pixel regions RP. GP and BP is formed on the buffer layer 320. The buffer layer 320 can be omitted.

A semiconductor layer 322 is formed on the buffer layer 320. The semiconductor layer 322 can include an oxide semiconductor material or polycrystalline silicon.

A gate insulating layer 324 is formed on the semiconductor layer 322. The gate insulating layer 324 can be formed of an inorganic insulating material such as silicon oxide or silicon nitride.

A gate electrode 330, which is formed of a conductive material, e.g., metal, is formed on the gate insulating layer 324 to correspond to a center of the semiconductor layer 322.

An interlayer insulating layer 332, which is formed of an insulating material, is formed on the gate electrode 330. The interlayer insulating layer 332 can be formed of an inorganic insulating material, e.g., silicon oxide or silicon nitride, or an organic insulating material, e.g., benzocyclobutene or photo-acryl.

The interlayer insulating layer 332 includes first and second contact holes 334 and 336 exposing both sides of the semiconductor layer 322. The first and second contact holes 334 and 336 are positioned at both sides of the gate electrode 330 to be spaced apart from the gate electrode 330.

A source electrode 340 and a drain electrode 342, which are formed of a conductive material, e.g., metal, are formed on the interlayer insulating layer 332.

The source electrode 340 and the drain electrode 342 are spaced apart from each other with respect to the gate electrode 330 and respectively contact both sides of the semiconductor layer 322 through the first and second contact holes 334 and 336.

The semiconductor layer 322, the gate electrode 330, the source electrode 340 and the drain electrode 342 constitute the TFT Tr. The TFT Tr serves as a driving element. Namely, the TFT Tr can correspond to the driving TFT Td (of FIG. 1).

The gate line and the data line cross each other to define the pixel region, and the switching TFT is formed to be connected to the gate and data lines. The switching TFT is connected to the TFT Tr as the driving element.

In addition, the power line, which can be formed to be parallel to and spaced apart from one of the gate and data lines, and the storage capacitor for maintaining the voltage of the gate electrode of the TFT Tr in one frame can be further formed.

A planarization layer 350, which includes a drain contact hole 352 exposing the drain electrode 342 of the TFT Tr, is formed to cover the TFT Tr.

A first electrode 360, which is connected to the drain electrode 342 of the TFT Tr through the drain contact hole 352, is separately formed in each pixel region and on a planarization layer 350. The first electrode 360 can be an anode and can include a transparent conductive layer being formed of a conductive material having a relatively high work function, e.g., a transparent conductive oxide (TCO). The first electrode 360 can further include a reflection electrode or a reflection layer. For example, the reflection electrode or the reflection layer can be formed of silver (Ag) or aluminum-palladium-copper (APC) alloy. In the top-emission organic light emitting display device 30), the first electrode 360 can have a triple-layered structure of ITO/Ag/ITO or ITO/APC/ITO.

A bank layer 366 covering an edge of the first electrode 360 is formed on the planarization layer 350. The bank layer 366 is positioned at a boundary of the red, green and blue pixel regions RP, GP and BP and exposes a center of the first electrode 360 in the red, green and blue pixel regions RP, GP and BP. Since the OLED D emits the white light in the red, green and blue pixel regions RP, GP and BP, the organic emitting layer 362 can be formed as a common layer in the red, green and blue pixel regions RP, GP and BP without separation in the red, green and blue pixel regions RP, GP and BP. The bank layer 366 can be formed to prevent the current leakage at an edge of the first electrode 360 and can be omitted.

An organic emitting layer 362 is formed on the first electrode 360.

Referring to FIG. 5, the organic emitting layer 362 includes a first emitting part 430 including a green EML 410, a second emitting part 440 including a first blue EML 450 and a third emitting part 460 including a second blue EML 470. In addition, the organic emitting layer 362 can further include a first charge generation layer (CGL) 480 between the first and second emitting parts 430 and 440 and a second CGL 490 between the first and third emitting parts 430 and 460. Moreover, the first emitting part 430 can further include a red EML 420.

The second emitting part 440 is positioned between the first electrode 360 and the first emitting part 430, and the third emitting part 460 is positioned between the first emitting part 430 and the second electrode 364. In addition, the second emitting part 440 is positioned between the first electrode 360 and the first CGL 480, and the third emitting part 460 is positioned between the second CGL 490 and the second electrode 364. Namely, the second emitting part 440, the first CGL 480, the first emitting part 430, the second CGL 490 and the third emitting part 460 are sequentially stacked on the first electrode 360.

In the first emitting part 430, the red EML 420 can be disposed under the green EML 410. In addition, the first emitting part 430 can further include at least one of a first HTL 432 and a first ETL 434.

For example, in the first emitting part 430, the red EML 420 can be positioned between the first HTL 432 and the green EML 410, and the green EML 410 can be positioned between the red EML 420 and the first ETL 434.

The second emitting part 440 can further include at least one of a second HTL 444 under the first blue EML 450 and a second ETL 448 on the first blue EML 450. In addition, the second emitting part 440 can further include an HIL 442 between the first electrode 360 and the second HTL 444. Moreover, the second emitting part 440 can further include a first EBL 446 between the second HTL 444 and the first blue EML 450.

The second emitting part 440 can further include a first HBL between the second ETL 448 and the first blue EML 450.

The third emitting part 460 can further include at least one of a third HTL 462 under the second blue EML 470 and a third ETL 466 on the second blue EML 470. In addition, the third emitting part 460 can further include an EIL 468 between the second electrode 364 and the third ETL 466. Moreover, the third emitting part 460 can further include a second EBL 464 between the third HTL 462 and the second blue EML 470.

The third emitting part 460 can further include a second HBL between the third ETL 466 and the second blue EML 470.

As described above, the green EML 410 includes the first host 412 being the first compound and the second host 414 being the second compound. In addition, the green EML 410 can further include the green dopant 416, e.g., the emitter. In the green EML 410, a weight % of each of the first and second hosts 412 and 414 can be greater than that of the green dopant 416. For example, the green dopant can be one of a green phosphorescent compound, a green fluorescent compound and a green delayed fluorescent compound.

In the green EML 410, the first host 412 is represented by Formula 1-1, and the second host 414 is represented by Formula 2-1. In this instance, at least one of the first host 412 and the second host 414 is deuterated. In addition, the green dopant 416 can be represented by Formula 5.

When the green EML 410 includes the first host 412, the second host 414 and the green dopant 416, a weight ratio of the first host 412 to the second host 414 can be 1:9 to 9:1, preferably 2:8 to 8:2, and more preferably 3:7 to 7:3. For example, the weight % of the first host 412 can be smaller than that of the second host 414. The weight ratio of the first host 412 to the second host 414 can be 2:8 to 4:6, preferably 3:7. In addition, in the green EML 410, the green dopant 416 can have a weight % of 3 weight % to 30 weight %, preferably 5 weight % to 15 weight %.

The red EML 420 can include a red host and a red dopant.

For example, the red host can be a spirofluorene-based organic compound, e.g., a spiro-fluorene derivative, in Formula 7-1. Alternatively, the red host can be a quinazoline-carbazole-based organic compound, e.g., a quinazoline-carbazole derivative, in Formula 18.

[Formula 18]

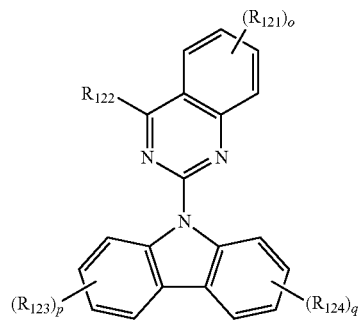

In Formula 18, $R_{121}$ is selected from the group consisting of deuterium. C1 to C20 alkyl group and C6 to C30 aryl group, and $R_{122}$ is C6 to C30 aryl group. Each of $R_{123}$ and $R_{124}$ is selected from the group consisting of deuterium and C10 to C30 heteroaryl group, or adjacent two $R_{123}$ or adjacent two $R_{124}$ are connected to each other to form a C6 to C10 aromatic ring. At least one of $R_{123}$ and $R_{124}$ is C10 to C30 heteroaryl group. Each of o, p and q, which are a number of substituents, is independently an integer of 0 to 4.

For example, the aryl group and the heteroaryl group can be unsubstituted or substituted with C6 to C20 aryl.

The red host in Formula 18 can be one of the compounds in Formula 19.

[Formula 19]
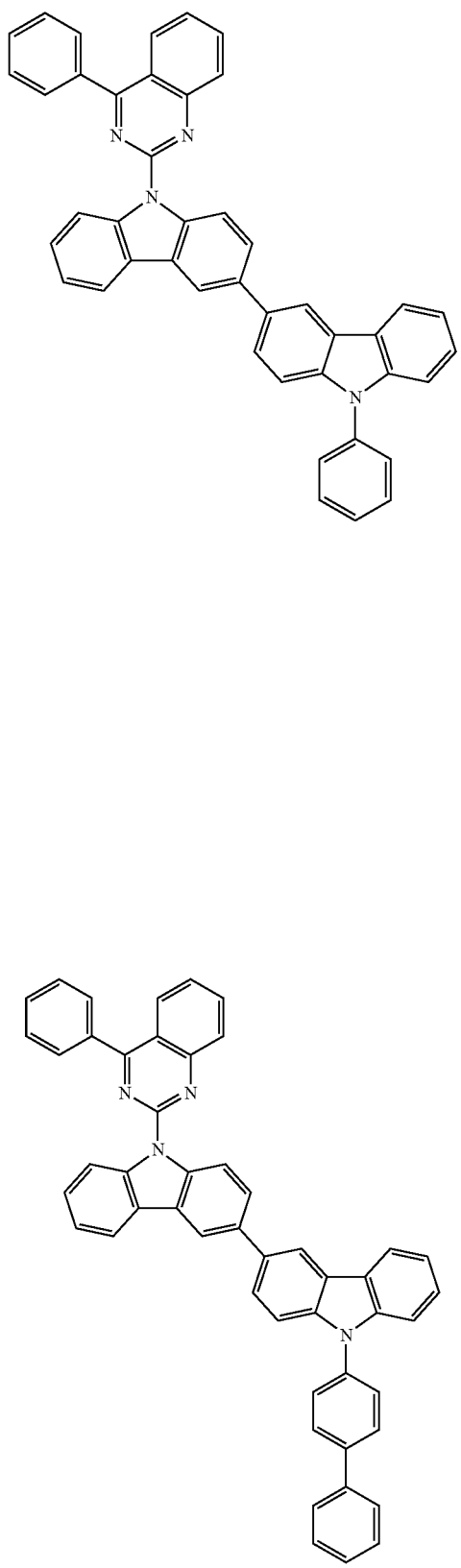
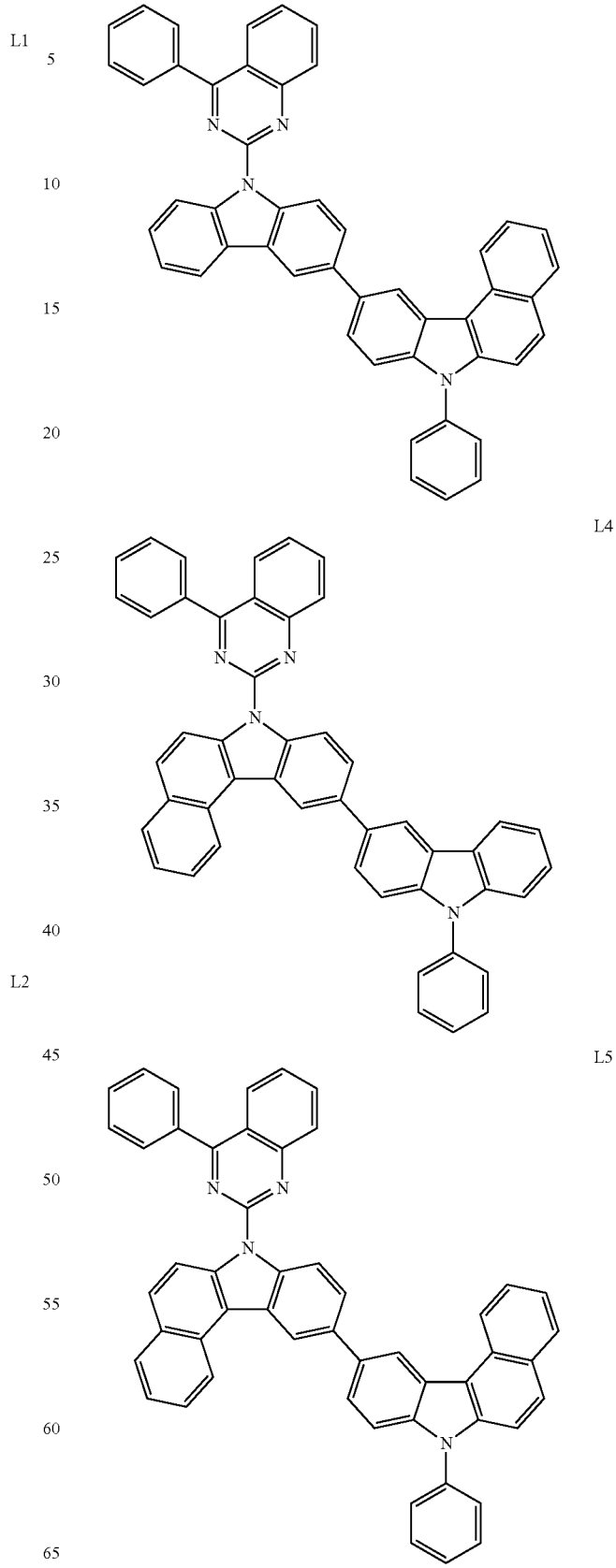

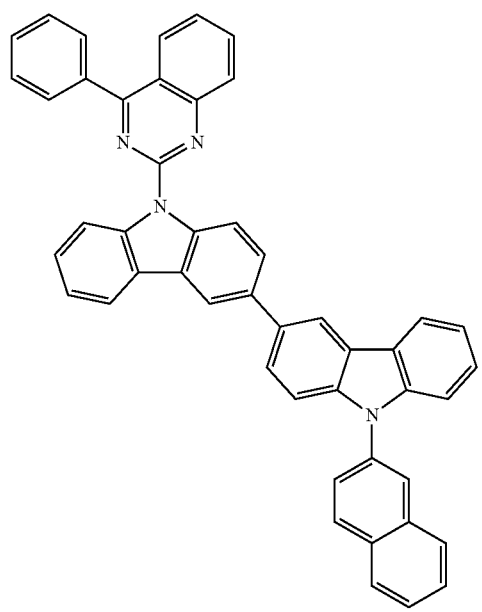
L6
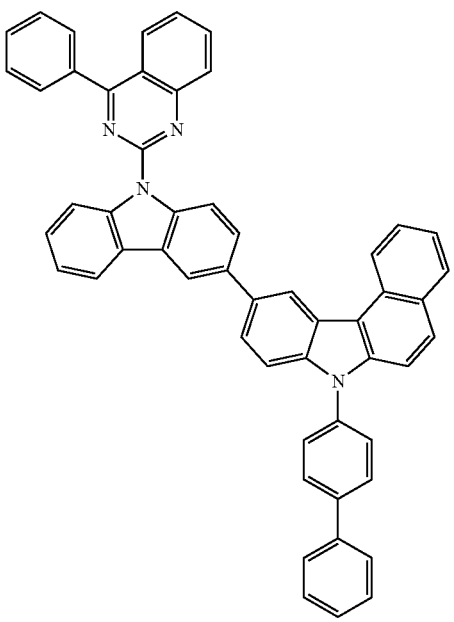
L8
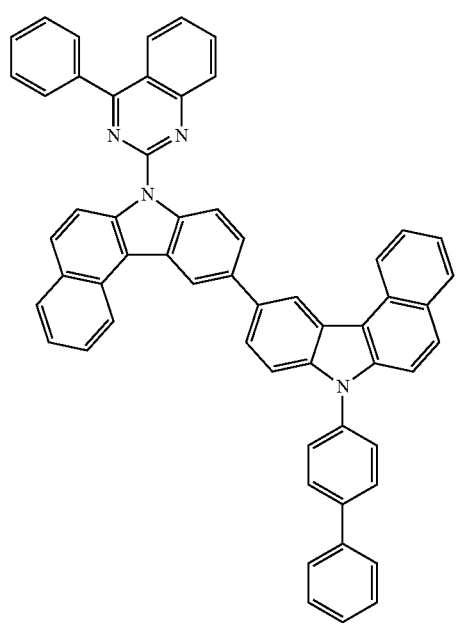
L7
L9

L10

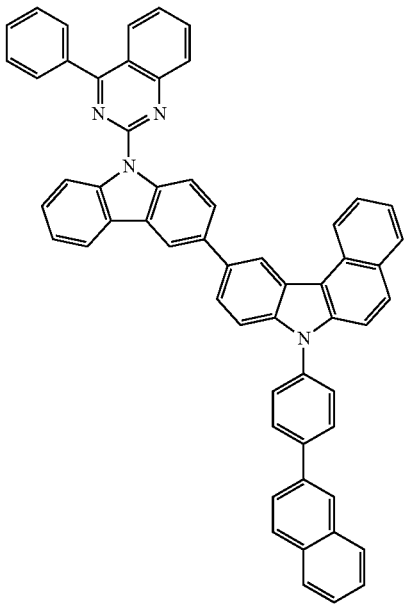

L11

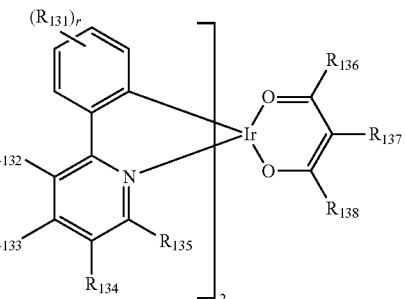

[Formula 20]

In Formula 20, $R_{131}$ is selected from the group consisting of deuterium, halogen atom. C1 to C6 alkyl group, C3 to C6 cycloalkyl group. C6 to C10 aryl group and C3 to C10 heteroaryl group, and r is an integer of 0 to 4. Each of $R_{132}$ to $R_{135}$ is independently selected from the group consisting of hydrogen, deuterium, halogen atom, C1 to C6 alkyl group. C3 to C6 cycloalkyl group, C6 to C10 aryl group and a C3 to C10 heteroaryl group, and at least adjacent two of $R_{132}$ to $R_{135}$ are connected to form a C6 to C10 aromatic ring (e.g., a fused ring). Each of $R_{36}$ to $R_{138}$ is independently selected from the group consisting of hydrogen, deuterium and C1 to C6 alkyl group.

The red dopant can be one of the compounds in Formula 21.

[Formula 21]

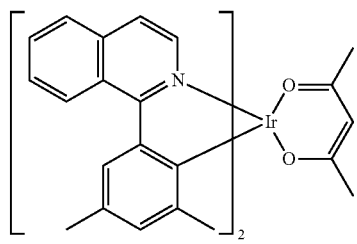

M1

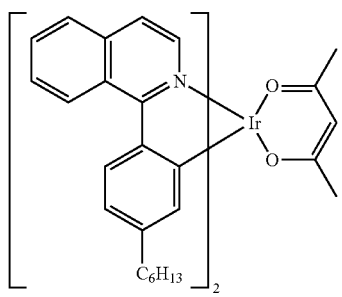

M2

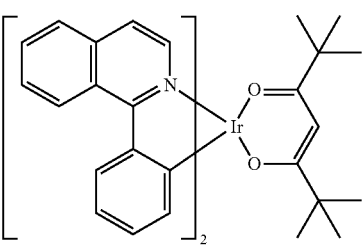

M3

The red host in the red EML 420 can include the compound in formula 7-1 as a p-type red host and the compound in Formula 18 as an n-type red host. In this instance, the p-type red host and the n-type red host can have a weight ratio of 1:9 to 9:1, preferably 2:8 to 8:2, and more preferably 3:7 to 7:3. For example, the weight % of the p-type red host can be smaller than that of the n-type red host. A weight ratio of the p-type red host to the n-type red host can be 1:9 to 4:6, preferably 3:7.

The red dopant can include at least one of a red phosphorescent compound, a red fluorescent compound and a red delayed fluorescent compound. For example, the red dopant can be represented by Formula 20.

-continued

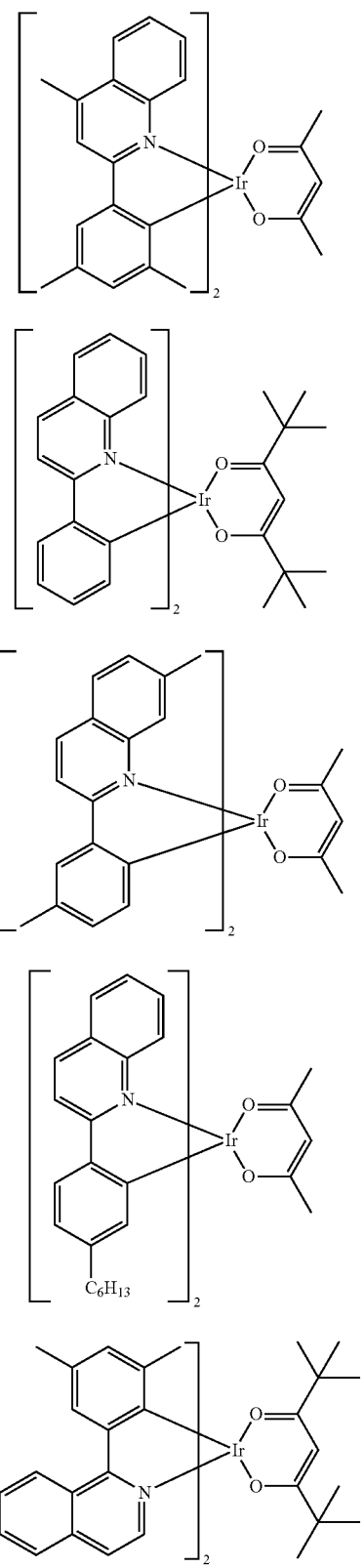

M4

M5

M6

M7

M8

In the red EML 420, the red dopant can be doped with a weight % of 1 weight % to 10 weight %, preferably 1 weight % to 5 weight %.

For example, in the first emitting part 430, a thickness of the green EML 410 can be greater than that of the red EML 420. In addition, a weight % of the green dopant 416 in the green EML 410 can be greater than that of the red dopant in the red EML 420.

The first blue EML 450 in the second emitting part 440 includes a first blue host and a first blue dopant, and the second blue EML 470 in the third emitting part 460 includes a second blue host and a second blue dopant. Each of the first and second blue hosts can be an anthracene derivative, and each of the first and second blue dopants can be a boron derivative.

For example, each of the first and second blue hosts can be represented by Formula 22-1.

[Formula 22-1]

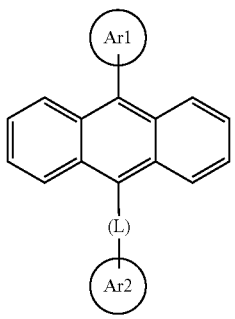

In Formula 22-1, each of Ar1 and Ar2 is independently C6 to C20 aryl group, and L is C6 to C20 arylene group.

For example, in Formula 22-1, each of Ar1 and Ar2 can be selected from the group consisting of phenyl, naphthyl and anthracenyl, and L can be selected from the group consisting of phenylene and naphthylene. Ar1 can be 1-naphtyl, Ar2 can be 2-naphthyl, and L can be phenylene.

In this instance, a part or all of hydrogens can be substituted by deuterium. Namely, the anthracene derivative can be partially or wholly deuterated. The first blue host included in the first blue EML 450 being closer to the first electrode 360 as the anode is an anthracene derivative having a first deuteration ratio, and the second blue host included in the second blue EML 470 being closer to the second electrode 364 as the cathode is an anthracene derivative having a second deuteration ratio. For example, the second deuteration ratio can be smaller than the first deuteration ratio.

Namely, in the OLED D, the first blue EML 450 in the second emitting part 440 includes the first blue host being the anthracene derivative, which has a first deuteration ratio, and the second blue EML 470 in the third emitting part 460 includes the second blue host being the anthracene derivative, which has a second deuteration ration being smaller than the first deuteration ratio.

The first blue host in the first blue EML 450 can be represented by Formula 22-2, and the second blue host in the second blue EML 470 can be represented by Formula 22-3.

[Formula 22-2]

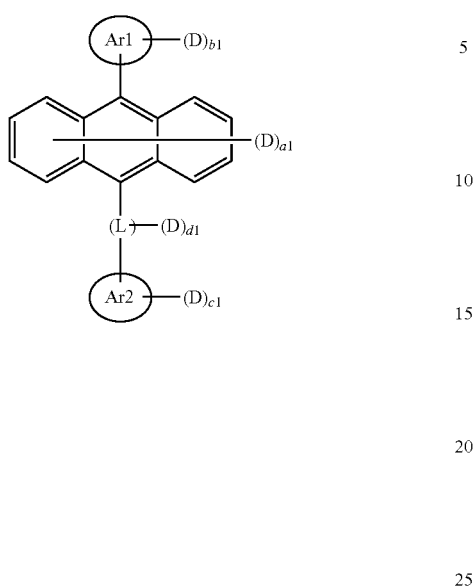

[Formula 22-3]

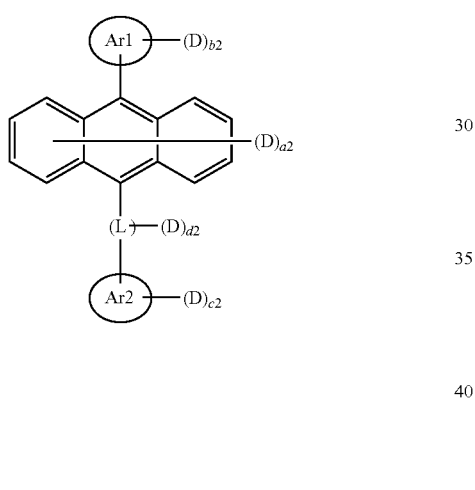

[Formula 22-4]

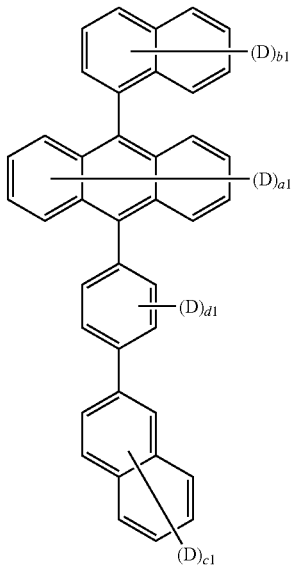

[Formula 22-5]

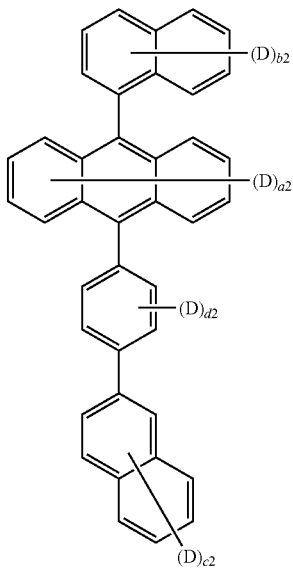

In Formulas 22-2 and 22-3, each of a1 and a2 is independently an integer of 0 to 8, and each of b1, b2, c1, c2, d1 and d2 is independently an integer of 0 to 20. A summation of a1, b1, c1 and d1 is greater than a summation of a2, b2, c2 and d2. Here, D is deuterium, and each of a1, a2, b1, b2, c1, c2, d1 and d2 is a number of deuterium.

Namely, the first blue host in the first blue EML 450 and the second blue host in the second blue EML 470 can be an anthracene derivative having the same chemical structure (or chemical formula) and have a difference in a deuteration ratio. In other words, the first blue host in the first blue EML 450 has a first deuteration ratio, and the second blue host in the second blue EML 470 has a second deuteration ratio being smaller than the first deuteration ratio.

The first blue host in the first blue EML 450 can be represented by Formula 22-4, and the second blue host in the second blue EML 470 can be represented by Formula 22-5.

In Formulas 22-4 and 22-5, each of a1 and a2 is independently an integer of 0 to 8, each of b1, b2, c1 and c2 is independently an integer of 0 to 7, and each of d1 and d2 is independently an integer of 0 to 4. A summation of a1, b1, c1 and d1 is greater than a summation of a2, b2, c2 and d2.

For example, in Formula 22-4, a1 is 8, b1 is 7, c1 is 7, and d1 is 4, thus the first blue host in the first blue EML 450 can be a compound in Formula 23-1. Namely, the first blue host in the first blue EML 450 can be an anthracene derivative, in which all hydrogens are deuterated (e.g., a wholly-deuterated anthracene derivative).

[Formula 23-1]

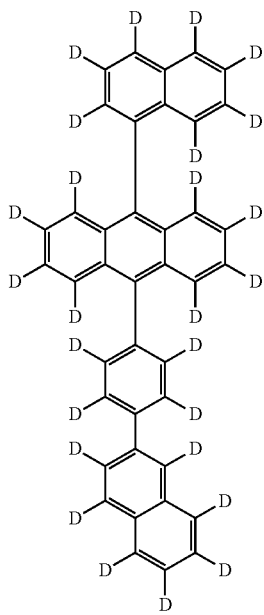

Host 1-5

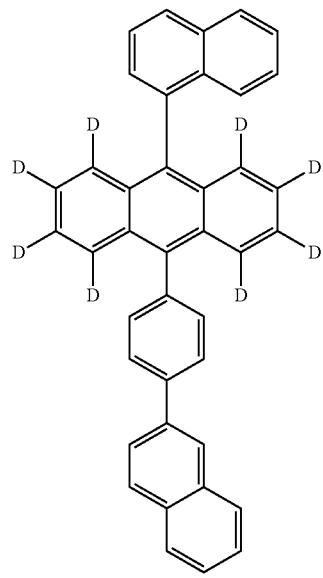

Host1-2

For example, in Formula 22-5, at least one of a2, b2, c2 and d2 is 0, thus the second blue host in the second blue EML 470 can be one of compounds in Formula 23-2. Namely, the second blue host in the second blue EML 470 can be an anthracene derivative, in which no hydrogen is deuterated (e.g., a non-deuterated anthracene derivative) or a part of hydrogens are deuterated (e.g., a partially-deuterated anthracene derivative).

[Formula 23-2]

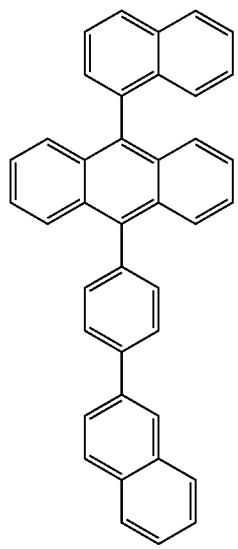

Host1-1

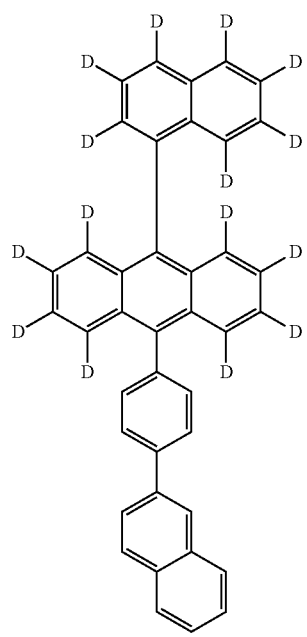

Host1-3

Host1-4

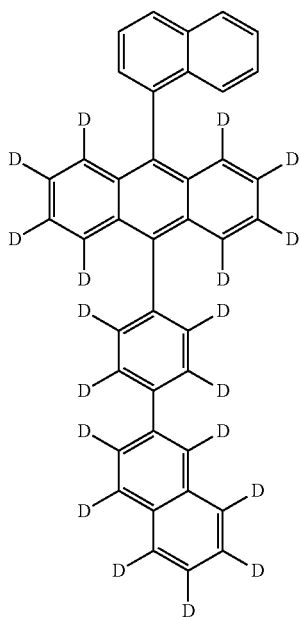

Namely, the first blue host in the first blue EML 450 being closer to the first electrode 360 as the anode can have a first deuteration ratio, e.g., 100%, and the second blue host in the second blue EML 470 being closer to the second electrode 364 as the cathode can have a second deuteration ratio, e.g., 0%, about 30%, about 52%, or about 70%, being smaller than the first deuteration ratio.

Each of the first blue dopant in the first blue EML 450 and the second blue dopant in the second blue EML 470 can be a boron derivative represented by Formula 24.

[Formula 24]

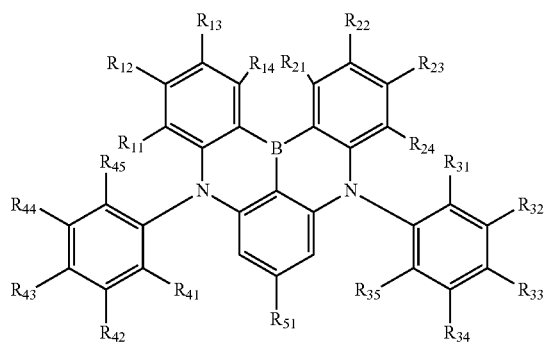

In Formula 24, each of $R_{11}$ to $R_{14}$, each of $R_{21}$ to $R_{24}$, each of $R_{31}$ to $R_{35}$ and each of $R_{41}$ to $R_{45}$ is selected from the group of hydrogen, deuterium (D), C1 to C10 alkyl group, C6 to C30 aryl group unsubstituted or substituted with C1 to C10 alkyl group, C12 to C30 arylamine group and C5 to C30 heteroaryl group, or adjacent two of $R_{11}$ to $R_{14}$, adjacent two of $R_{21}$ to $R_{24}$, adjacent two of $R_{31}$ to $R_{35}$ and adjacent two of $R_{41}$ to $R_{45}$ are connected (combined) to each other to form a fused ring unsubstituted or substituted with C1 to C10 alkyl group, e.g., an aryl ring or a heteroaryl ring. $R_{51}$ is selected from the group consisting of hydrogen, D, C1 to C10 alkyl group and C3 to C15 cycloalkyl group, C6 to C30 aryl group, C5 to C30 heteroaryl group and C6 to C30 arylamine group unsubstituted or substituted with C1 to C10 alkyl group.

Each of $R_{11}$ to $R_{14}$, each of $R_{21}$ to $R_{24}$, each of $R_{31}$ to $R_{35}$ and each of $R_{41}$ to $R_{45}$ can be same or different.

In the boron derivative being the first and second blue dopant, the benzene ring, which is connected to boron atom and two nitrogen atoms, is substituted with unsubstituted or deuterium-substituted (e.g., D-substituted) C12 to C30 arylamine group or unsubstituted or D-substituted C5 to C30 heteroaryl group such that the emitting property of the OLED D can be further improved. Namely, when $R_{51}$ in Formula 24 is unsubstituted or D-substituted C12 to C30 arylamine group or unsubstituted or D-substituted C5 to C30 heteroaryl group, e.g., carbazole, the emitting property of the OLED D can be further improved.

For example, C1 to C10 alkyl group can be one of methyl, ethyl, propyl, butyl, and pentyl (amyl). The substituted or unsubstituted C6 to C30 aryl group can be one of phenyl and naphthyl and can be substituted with D or C1~C10 alkyl. In addition, C12 to C30 arylamine group can be one of diphenylamine group, phenyl-biphenylamine group, phenyl-naphthylamine group, and dinaphthylamine group, and C5 to C30 heteroaryl group can be one of pyridyl, quinolinyl, carbazolyl, dibenzofuranyl, and dibenzothiophenyl. In this instance, arylamine group, aryl group, alkyl group, and heteroaryl group can be substituted with D.

Each of $R_{11}$ to $R_{14}$, each of $R_{21}$ to $R_{24}$, each of $R_{31}$ to $R_{35}$ and each of $R_{41}$ to $R_{45}$ can be independently selected from the group consisting of H, D, methyl, ethyl, propyl, butyl, and pentyl (amyl). $R_{51}$ can be selected from the group consisting of unsubstituted or D-substituted diphenylamine group, unsubstituted or D-substituted phenyl-biphenylamine group, unsubstituted or D-substituted phenyl-naphthylamine group, unsubstituted or D-substituted biphenyl-naphthylamine group, and unsubstituted or D-substituted carbazoyl.

In one embodiment, one of $R_{11}$ to $R_{14}$, one of R-n to $R_{24}$, one of $R_{31}$ to $R_{35}$ and one of $R_{41}$ to $R_{45}$ can be tert-butyl or tert-pentyl (or tert-amyl), and the rest of $R_{11}$ to $R_{14}$, the rest of $R_1$ to $R_{24}$, the rest of R to $R_{35}$ and the rest of $R_{41}$ to $R_{45}$ can be hydrogen or deuterium, and $R_{51}$ can be D-substituted diphenylamine group. When the compound is used as the first and second blue dopants, the emitting efficiency and the color sense of the OLED are improved.

The first and second blue dopants can be same or different and can be independently one of the compounds in Formula 25.

[Formula 25]
Dopant 1
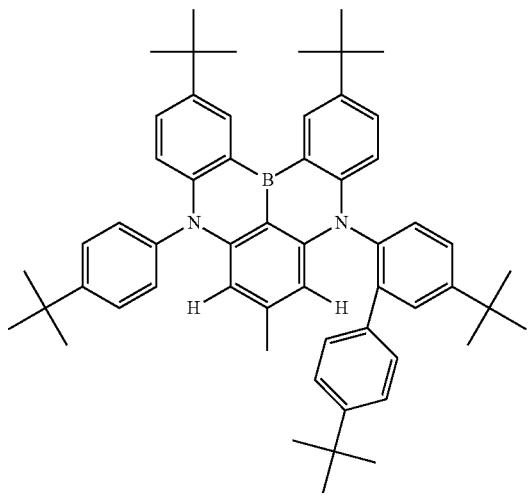
Dopant 2
Dopant 3
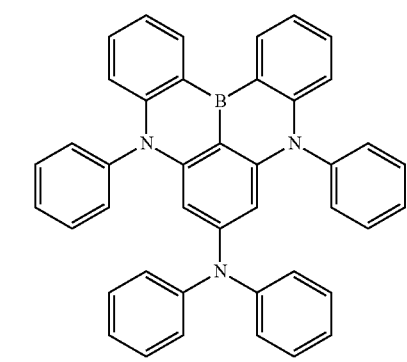
Dopant 4
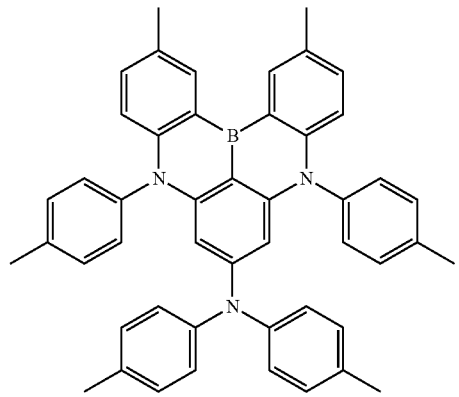
Dopant 5
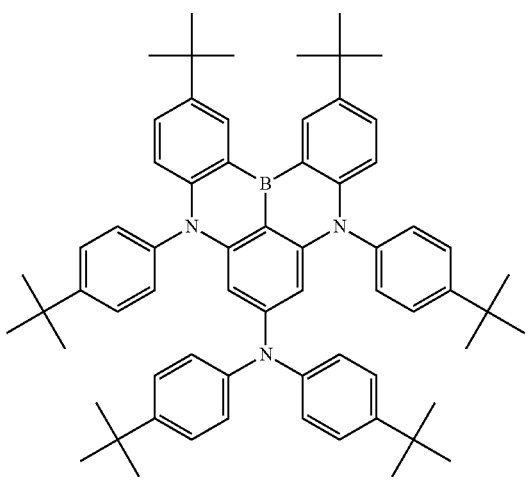
Dopant 6
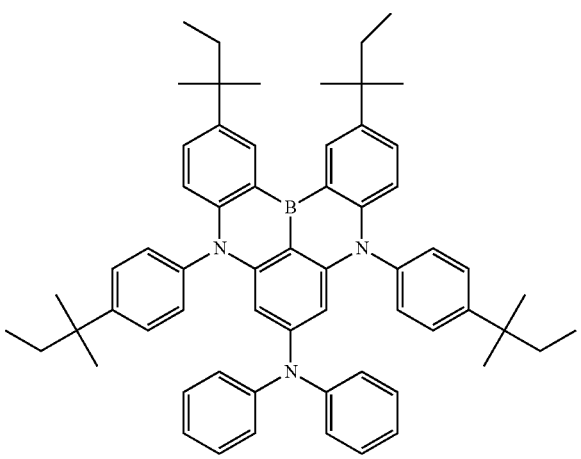

Dopant 7
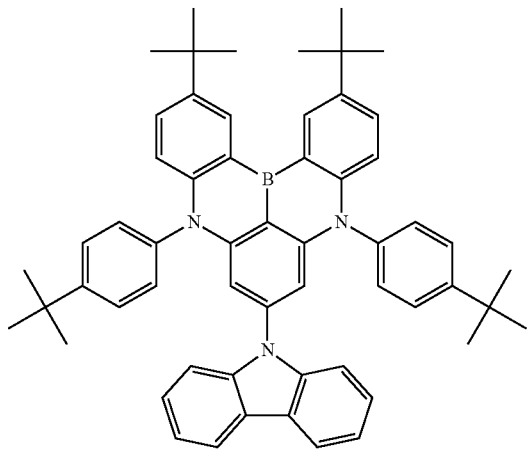
Dopant 10
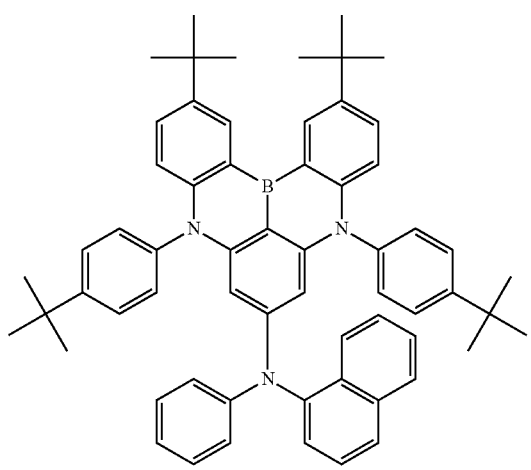
Dopant 8
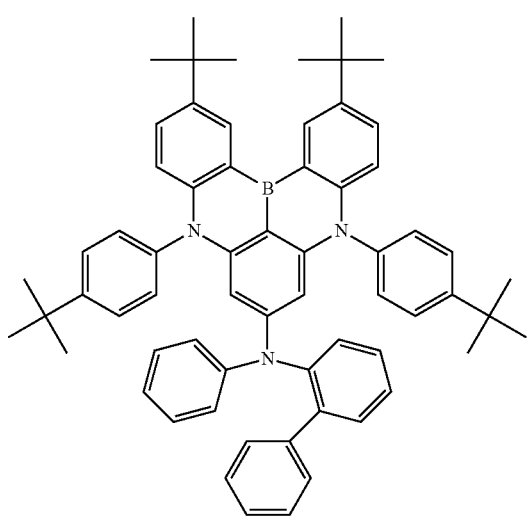
Dopant 11
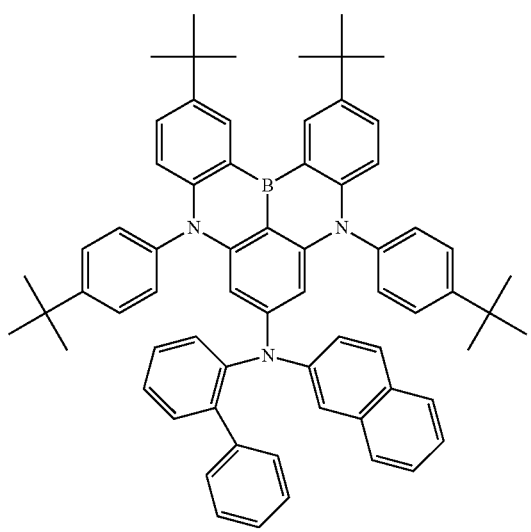
Dopant 12
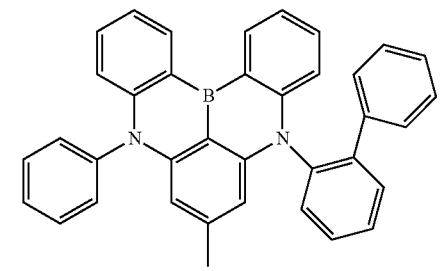
Dopant 9
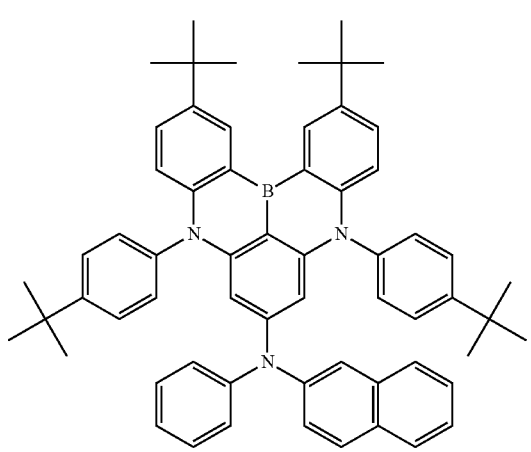
Dopant 13
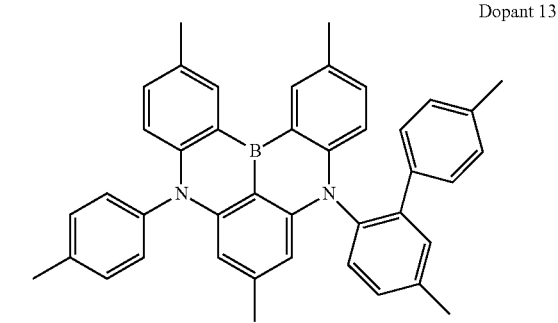

Dopant 14

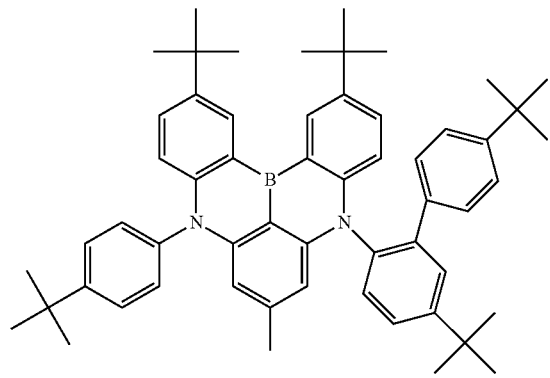

Dopant 15

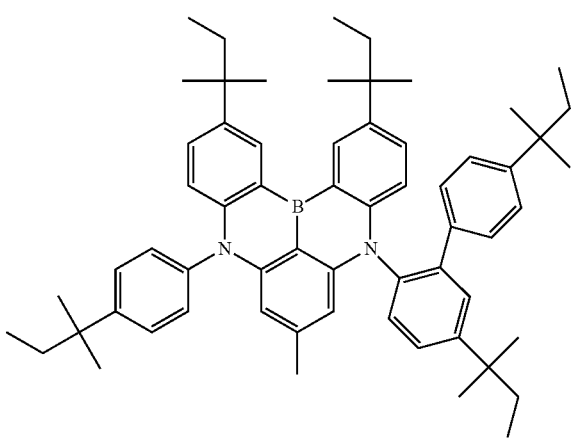

Dopant 16

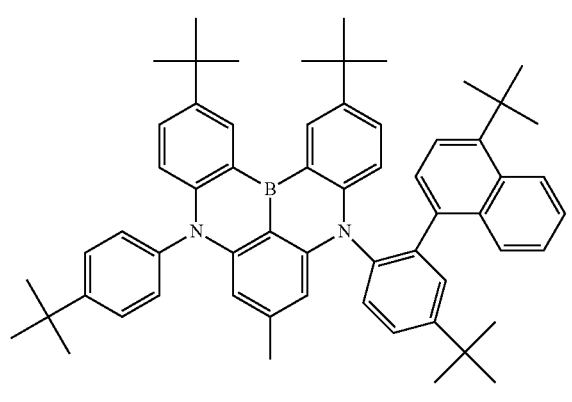

Dopant 17

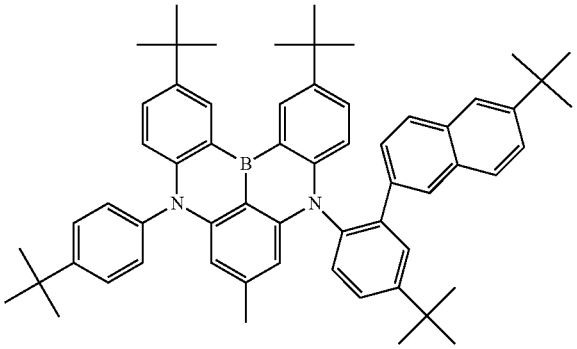

Dopant 18

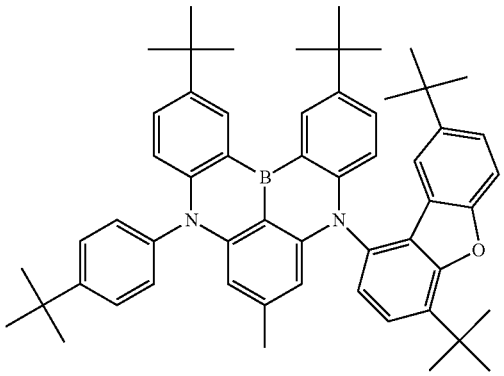

Dopant 19

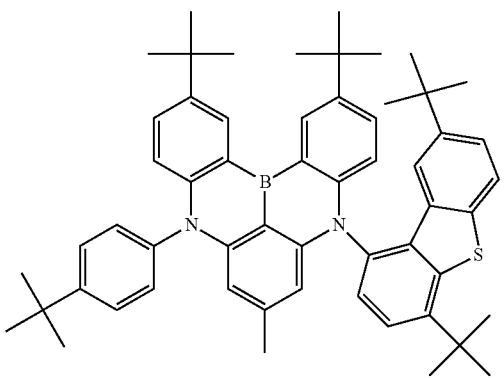

The first blue dopant can have a weight % of 0.1 weight % to 10 weight %, e.g., 1 weight % to 5 weight %, in the first blue EML 450, and the second blue dopant can have a weight % of 0.1 weight % to 10 weight %. e.g., 1 weight % to 5 weight %, in the second blue EML 470. For example, the weight % of the first blue dopant in the first blue EML 450 can be equal to or greater than that of the second blue dopant in the second blue EML 470.

Each of the first and second blue EMLs 450 and 470 can have a thickness of 10 Å to 1000, e.g., 100 to 500 Å, but it is not limited thereto. For example, the thickness of the first blue EML 450 can be equal to or smaller than that of the second blue EML 470.

For example, the thickness of the first blue EML 450 can be smaller than that of the second blue EML 470, and the weight % of the first blue dopant in the first blue EML 450 can be greater than that of the second blue dopant in the second blue EML 470.

The HIL 442 in the second emitting part 440 includes the compound in Formula 7-1, e.g., a hole injection material. In addition, the HIL 442 can further include one of the compounds in Formula 9 as a p-type dopant.

The first HTL 432 in the first emitting part 430, the second HTL 444 in the second emitting part 440 and the third HTL 462 in the third emitting part 460 can include the compound in Formula 7-1, e.g., a hole transporting material.

For example, a thickness of the third HTL 462 can be equal to or smaller than that of the second HTL 444 and can be greater than the first HTL 432. The first HTL 432 can have a thickness of about 10 to 150 Å, the second HTL 444 can have a thickness of about 50) to 1000 Å, and the third HTL 462 can have a thickness of about 500 to 900 Å.

In the HIL 442, a weight ratio of the first hole injection material to the second hole injection material can be 8:2 to 5:5, and the HIL 442 can have a thickness of about 10 to 100 Å.

Each of the first to third ETL 434, 448 and 466 can include at least one of the benzimidazole-based organic compound in Formula 10 and the azine-based organic compound in Formula 12.

For example, each of the first and third ETL 434 and 466 can include the electron transporting material in Formula 10, and the second ETL 448 can include the electron transporting material in Formula 12. The third ETL 466 can further include the electron transporting material in Formula 12. Namely, the first ETL 434 can include a single material of the electron transporting material in Formula 10, the second ETL 448 can include a single material of the electron transporting material in Formula 12, while the third ETL 466 can include two materials of the electron transporting materials in Formulas 10 and 12. In the third ETL 466, the electron transporting material in Formula 10 and the electron transporting material in Formula 12 can have the same weight %.

The EIL 468 can include the electron injection material being the compound in Formula 14. In addition, the EIL 468 can further include a dopant being one of alkali metal, e.g., Li, Na, K or Cs, and alkali earth metal, e.g., Mg, Sr, Ba or Ra.

Each of the first EBL 446 in the second emitting part 440 and the second EBL 464 in the third emitting part 460 can include the electron blocking material being the compound in formula 16.

The first CGL 480 is positioned between the first emitting part 430 and the second emitting part 440, and the second CGL 490 is positioned between the first emitting part 430 and the third emitting part 460. Namely, the first and second emitting parts 430 and 440 are connected through the first CGL 480, and the first and third emitting parts 430 and 460 are connected through the second CGL 490. The first CGL 480 can be a P-N junction CGL of an N-type CGL 482 and a P-type CGL 484, and the second CGL 490 can be a P-N junction CGL of an N-type CGL 492 and a P-type CGL 494.

In the first CGL 480, the N-type CGL 482 is positioned between the first HTL 432 and the second ETL 448, and the P-type CGL 484 is positioned between the N-type CGL 482 and the first HTL 432.

In the second CGL 490, the N-type CGL 492 is positioned between the first ETL 434 and the third HTL 462, and the P-type CGL 494 is positioned between the N-type CGL 492 and the third HTL 462.

Each of the N-type CGL 482 in the first CGL 480 and the N-type CGL 492 in the second CGL 490 can include a phenanthroline-based compound of Formula 14 as an N-type charge generation material.

Each of the N-type CGL 482 in the first CGL 480 and the N-type CGL 492 in the second CGL 490 can further include a dopant being at least one of alkali metal, e.g., Li, Na, K or Cs, and alkali earth metal, e.g., Mg, Sr, Ba or Ra. In this instance, the electron generation property and/or the electron injection property of the N-type CGLs 482 and 492 can be improved. In each of the N-type CGLs 482 and 492, the dopant can have a weight % of 0.1 weight % to 10 weight %. In addition, each of the N-type CGLs 482 and 492 can have a thickness of 30 to 500 Å, preferably 50 to 300 Å. For example, the weight % of the dopant in the N-type CGL 482 in the first CGL 480 can be greater than that of the dopant in the N-type CGL 492 in the second CGL 490, and the thickness of the N-type CGL 482 in the first CGL 480 can be smaller than that of the N-type CGL 492 in the second CGL 490.

Each of the P-type CGL 484 in the first CGL 480 and the P-type CGL 494 in the second CGL 490 can include the compound in Formula 7-1 as a p-type charge generation material.

In addition, each of the P-type CGL 484 in the first CGL 480 and the P-type CGL 494 in the second CGL 490 can include the compound in Formula 9 as a dopant.

In each of the P-type CGLs 484 and 494, the dopant can have a weight % of 1 weight % to 40 weight %, preferably 3 weight % to 30 weight %. In addition, each of the P-type CGLs 484 and 494 can have a thickness of 30 to 500 Å, preferably 50 to 200 Å.

For example, the weight % of the dopant in the P-type CGL 484 in the first CGL 480 can be equal to that of the dopant in the P-type CGL 494 in the second CGL 490, and the thickness of the P-type CGL 484 in the first CGL 480 can be smaller than that of the P-type CGL 494 in the second CGL 490.

As described above, the OLED D of the present disclosure includes the first emitting part 430, which includes the green EML 410 and the red EML 420, the second emitting part 440, which includes the first blue EML 450, and the third emitting part 460, which includes the second blue EML 470, so that the white light is provided from the OLED D.

The green EML 410 includes the first host 412 and the second host 414, and at least one of the first and second hosts 412 and 414 is deuterated. Accordingly, the emitting efficiency and the lifespan of the OLED D and the organic light emitting display device 300 are increased.

In addition, when only the fused-hetero ring moiety in the first host 412 is deuterated and/or only the biscarbazole moiety in the second host 414 is deuterated, the lifespan of the OLED D and the organic light emitting display device 300 is further improved.

Moreover, the first blue host of the first blue EML 450 is an anthracene derivative having a first deuteration ratio, and the second blue host of the second blue EML 470 is an anthracene derivative having a second deuteration ratio, which is smaller than the first deuteration ratio. Accordingly, the emitting efficiency and the lifespan of the OLED D and the organic light emitting display device 300 are further increased.

Referring to FIG. 6, the organic emitting layer 362 includes a first emitting part 530, which includes a green EML 510, a red EML 520 and a yellow-green EML 525, a second emitting part 540 including a first blue EML 550, and a third emitting part 560 including a second blue EML 570. In addition, the organic emitting layer 362 can further include a first CGL 580 between the first and second emitting parts 530 and 540 and a second CGL 590 between the first and third emitting parts 530 and 560.

The second emitting part 540 is positioned between the first electrode 360 and the first emitting part 530, and the third emitting part 560 is positioned between the first emitting part 530 and the second electrode 364. In addition, the second emitting part 540 is positioned between the first electrode 360 and the first CGL 580, and the third emitting part 560 is positioned between the second CGL 590 and the second electrode 364. Namely, the second emitting part 540, the first CGL 580, the first emitting part 530, the second CGL 590 and the third emitting part 560 are sequentially stacked on the first electrode 360.

In the first emitting part 530, the red EML 520 is disposed under the yellow-green EML 525, and the green EML 510 is disposed over the yellow-green EML 525. Namely, the EML having a double-layered structure is included in the first emitting part 430 of the OLED in FIG. 5, while the EML having a triple-layered structure is included in the first emitting part 530 of the OLED in FIG. 6.

In addition, the first emitting part 530 can further include at least one of a first HTL 532 and a first ETL 534.

The second emitting part 540 can further include at least one of a second HTL 544 under the first blue EML 550 and a second ETL 548 on the first blue EML 550. In addition, the second emitting part 540 can further include an HIL 542 between the first electrode 360 and the second HTL 544. Moreover, the second emitting part 540 can further include a first EBL 546 between the second HTL 544 and the first blue EML 550.

The second emitting part 540 can further include a first HBL between the second ETL 548 and the first blue EML 550.

The third emitting part 560 can further include at least one of a third HTL 562 under the second blue EML 570 and a third ETL 566 on the second blue EML 570. In addition, the third emitting part 560 can further include an EIL 568 between the second electrode 364 and the third ETL 566. Moreover, the third emitting part 560 can further include a second EBL 564 between the third HTL 562 and the second blue EML 570.

The third emitting part 560 can further include a second HBL between the third ETL 566 and the second blue EML 570.

As described above, the green EML 510 includes the first host 512 being the first compound and the second host 514 being the second compound. In addition, the green EML 510 can further include the green dopant 516, e.g., the emitter. In the green EML 510, a weight % of each of the first and second hosts 512 and 514 can be greater than that of the green dopant 516. For example, the green dopant can be one of a green phosphorescent compound, a green fluorescent compound and a green delayed fluorescent compound.

In the green EML 510, the first host 512 is represented by Formula 1-1, and the second host 514 is represented by Formula 2-1. In this instance, at least one of the first host 512 and the second host 514 is deuterated. In addition, the green dopant 516 can be represented by Formula 5.

When the green EML 510 includes the first host 512, the second host 514 and the green dopant 516, a weight ratio of the first host 512 to the second host 514 can be 1:9 to 9:1, preferably 2:8 to 8:2, and more preferably 3:7 to 7:3. For example, the weight % of the first host 512 can be smaller than that of the second host 514. The weight ratio of the first host 512 to the second host 514 can be 2:8 to 4:6, preferably 3:7. In addition, in the green EML 510, the green dopant 516 can have a weight % of 3 weight % to 30 weight %, preferably 5 weight % to 15 weight %.

The red EML 520 can include a red host and a red dopant. For example, the red host can be a spirofluorene-based organic compound, e.g., a spiro-fluorene derivative, in Formula 7-1 and can be one of the compounds in Formula 8. Alternatively, the red host can be a quinazoline-carbazole-based organic compound. e.g., a quinazoline-carbazole derivative, in Formula 18 and can be one of the compounds in Formula 19. The red EML 520 can include both the compound in Formula 7-1 as a first red host and the compound in Formula 18 as a second red host.

The red dopant can include at least one of a red phosphorescent compound, a red fluorescent compound and a red delayed fluorescent compound. For example, the red dopant can be represented by Formula 20 and can be one of the compounds in Formula 21.

The yellow-green EML 525 can include a first yellow-green host and a yellow-green dopant. In addition, the yellow-green EML 525 can further include a second yellow-green host.

The first yellow-green host can be a P-type host and can be represented by Formula 27.

[Formula 27]

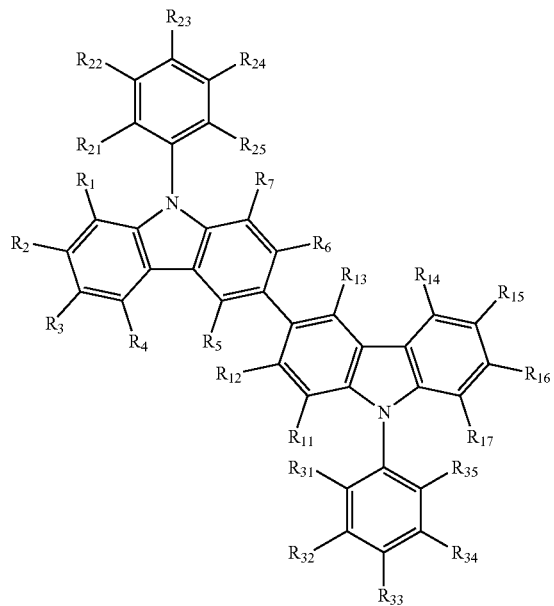

In Formula 27, each of $R_1$ to $R_7$ and $R_{11}$ to $R_{17}$ is independently hydrogen or deuterium. Each of $R_{21}$ to $R_{25}$ and $R_{31}$ to $R_{35}$ is independently selected from the group consisting of hydrogen, deuterium, C1 to C10 alkyl group and C6 to C30 aryl group unsubstituted or substituted with deuterium, or adjacent two of $R_{21}$ to $R_{25}$ and/or adjacent two of $R_{31}$ to $R_{35}$ are combined (or linked) to each other to form a fused ring. For example, the fused ring can be an aromatic ring.

The first yellow-green host in Formula 27 can be one of the compounds in Formula 28.

[Formula 28]
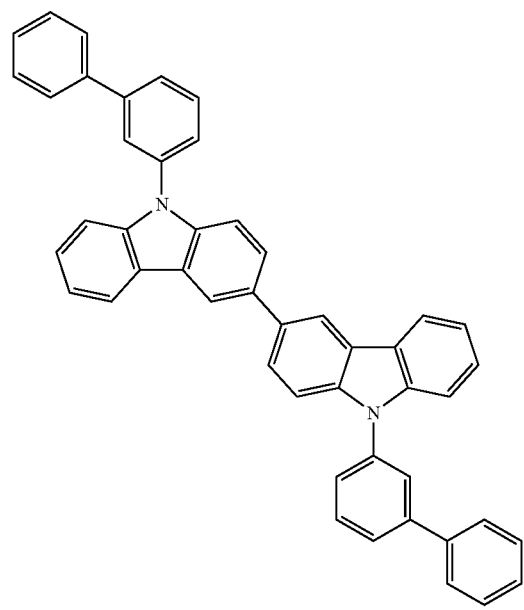
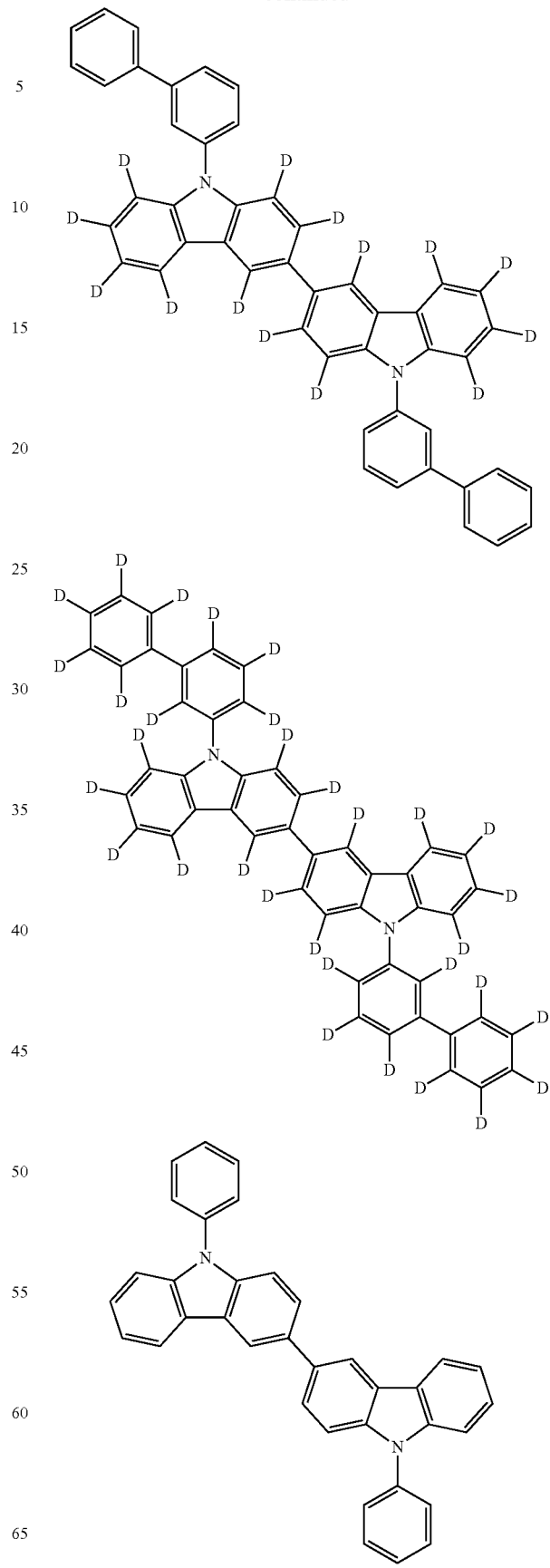

103
-continued
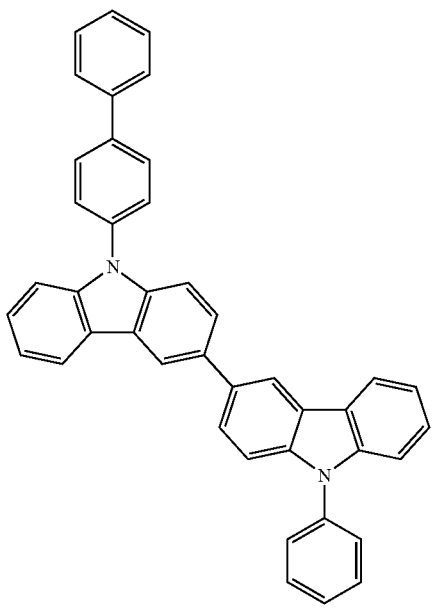
104
-continued
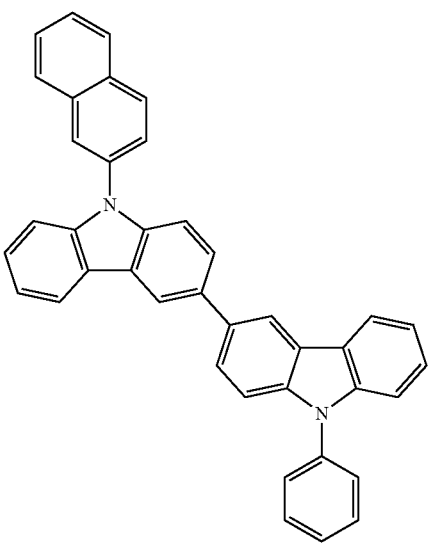
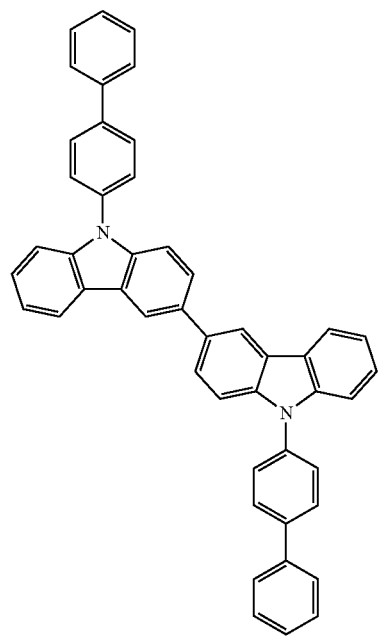
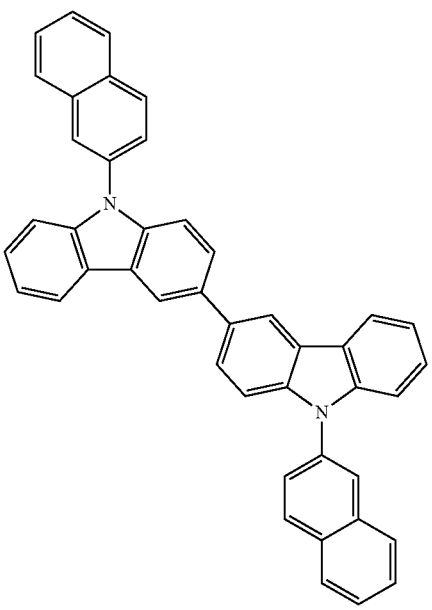

105
-continued
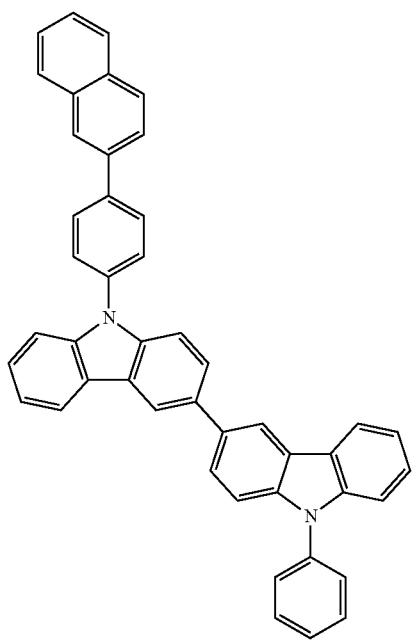
106
-continued
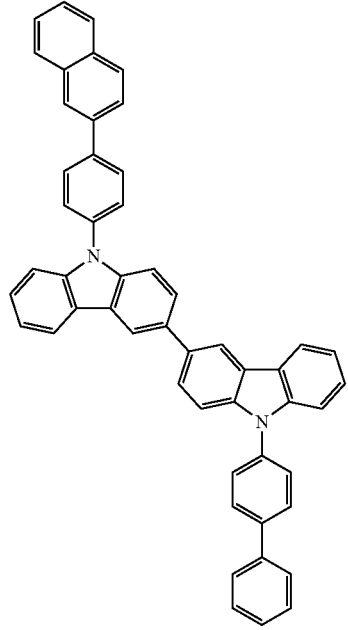
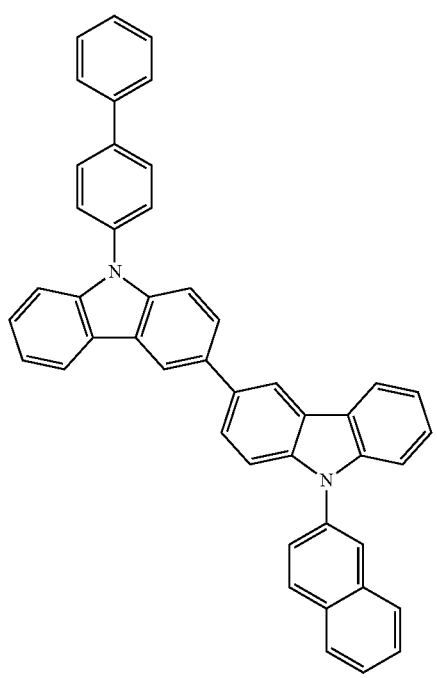
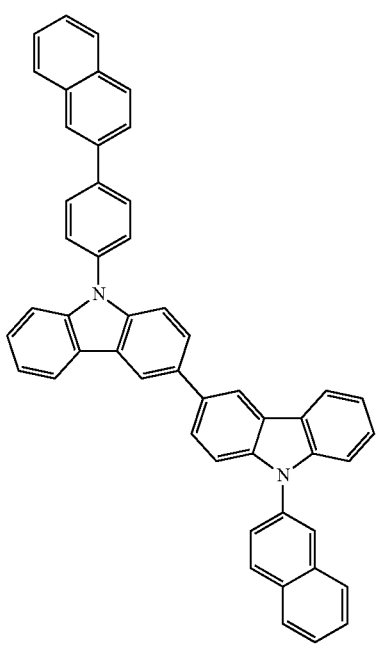 [SMILES: c1ccc2cc(-c3ccc(-n4c5ccccc5c5cc(-c6ccc7c(c6)c6ccccc6n7-c6ccc7ccccc7c6)ccc54)cc3)ccc2c1]

The second yellow-green host can be an N-type host and can be represented by Formula 29.

[Formula 29]

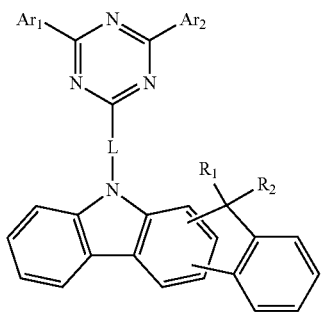

In Formula 29, each of Ar and Ar2 is independently C6 to C30 aryl group, each of $R_1$ and $R_2$ is independently selected from the group consisting of hydrogen. C1 to C10 alkyl group and C6 to C30 aryl group, and L is C6 to C30 arylene group.

For example, each of $Ar_1$ and $Ar_2$ can be independently phenyl or naphthyl, each of $R_1$ and $R_2$ can be C1 to C10 alkyl, and L can be phenylene or naphthylene.

The second yellow-green host in Formula 29 can be one of the compounds in Formula 30.

[Formula 30]

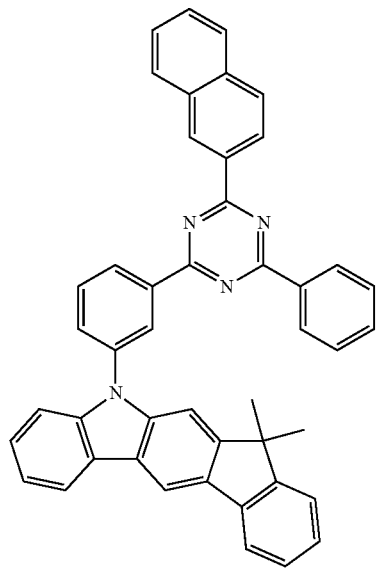

-continued

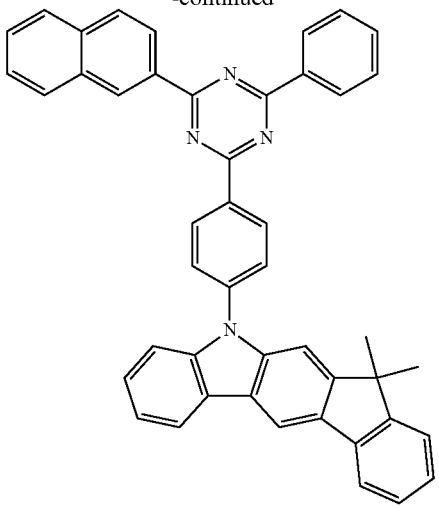

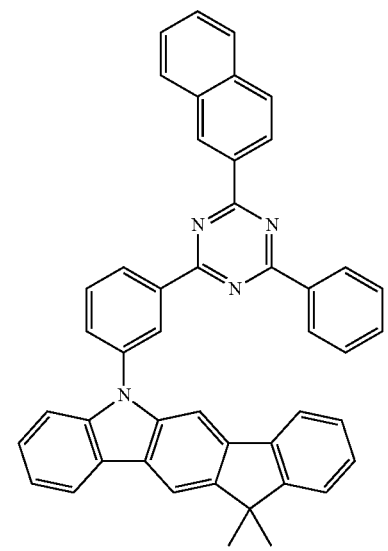

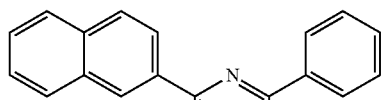

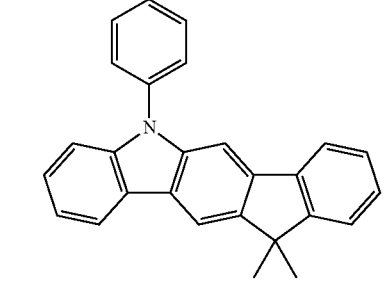

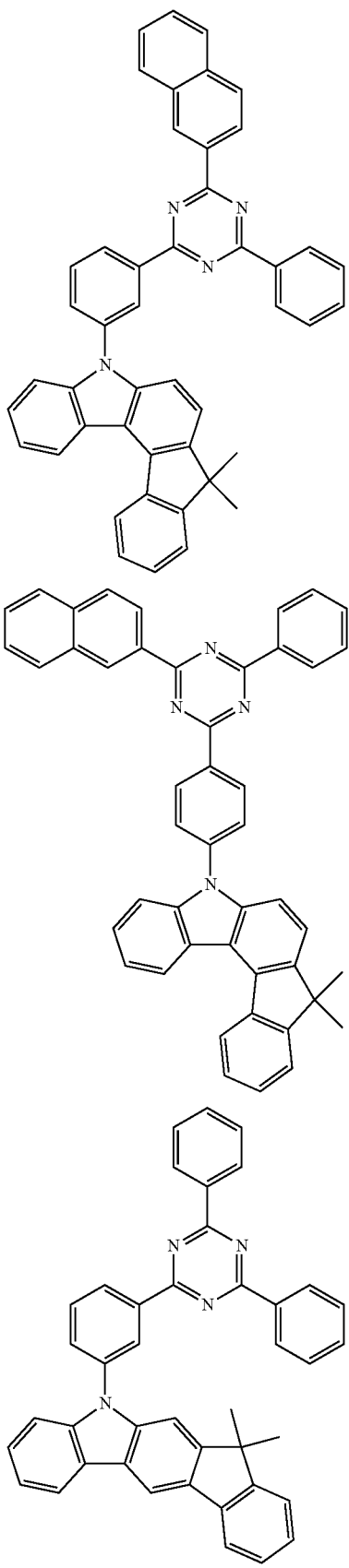

111
-continued
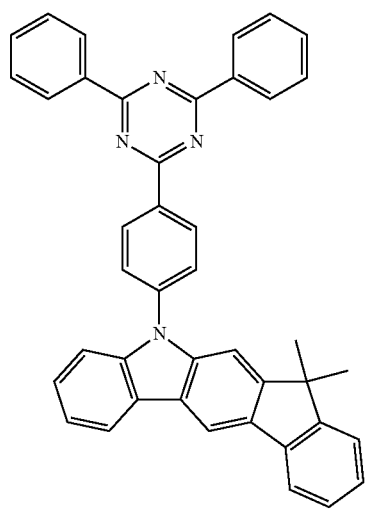
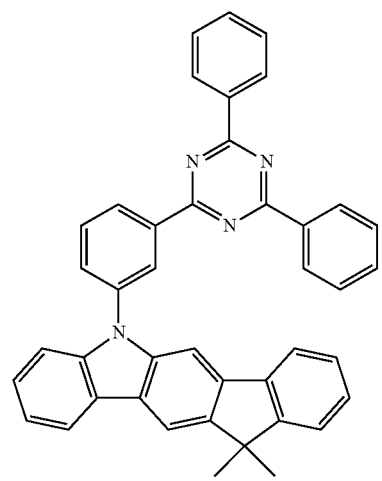
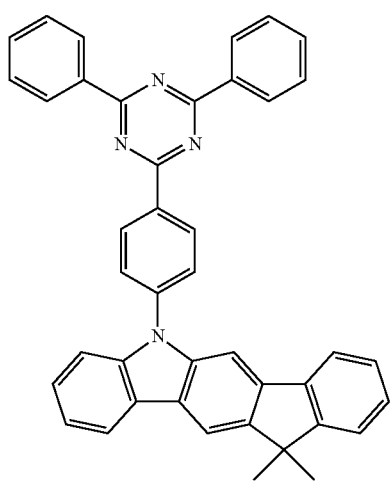
112
-continued
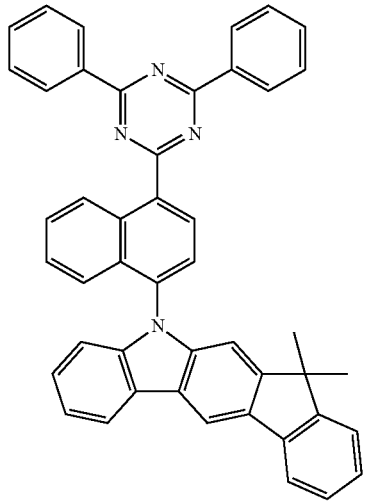
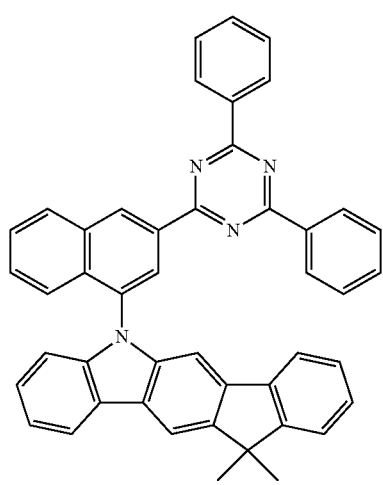
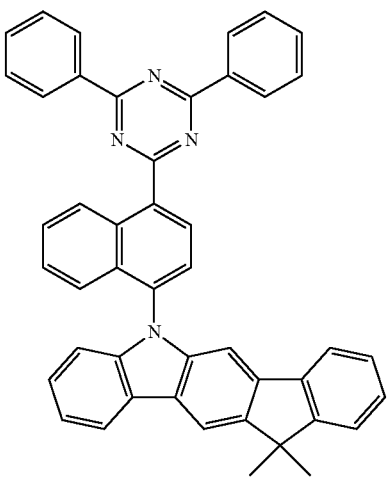

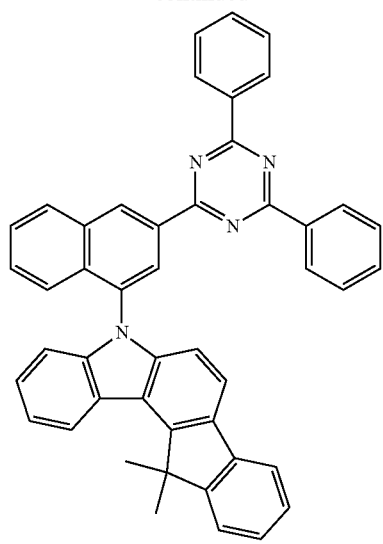
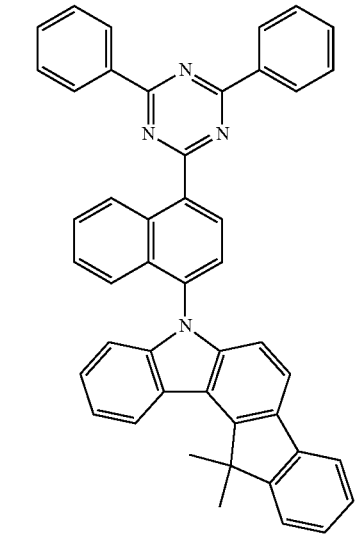
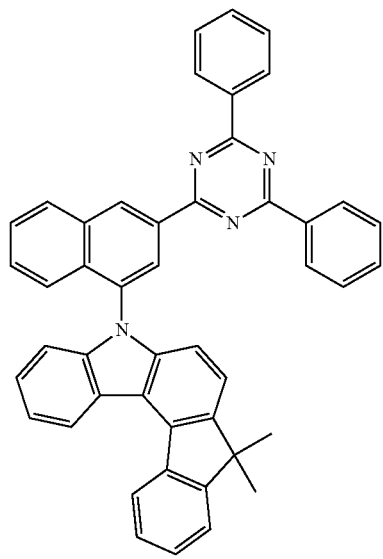
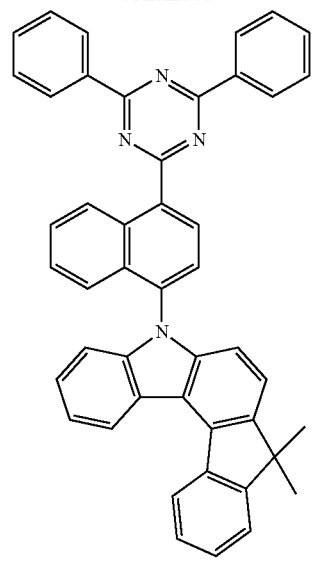
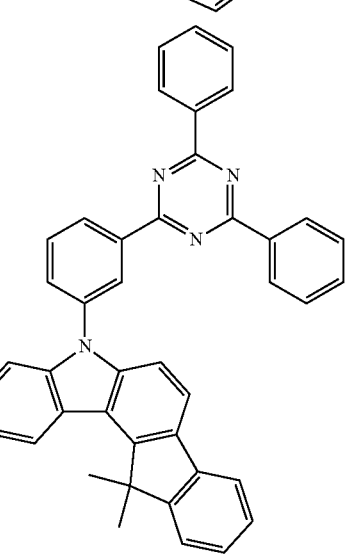
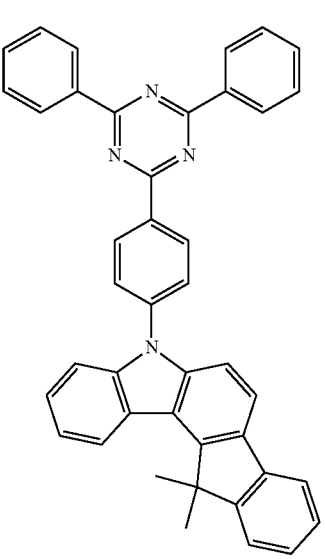

-continued

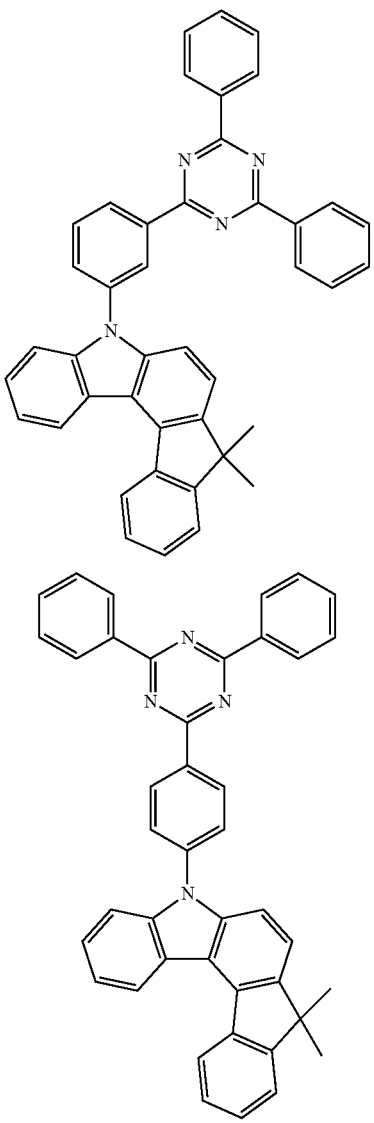

The yellow-green dopant can be represented by Formula 31.

[Formula 31]

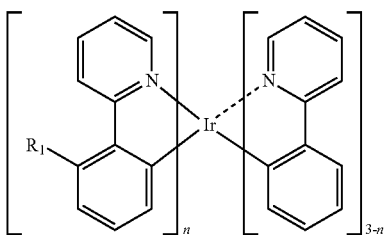

In Formula 31, $R_1$ is C6 to C30 aryl group, and n is an integer of 0 to 3.

The yellow-green dopant can be the compound in Formula 32.

[Formula 32]

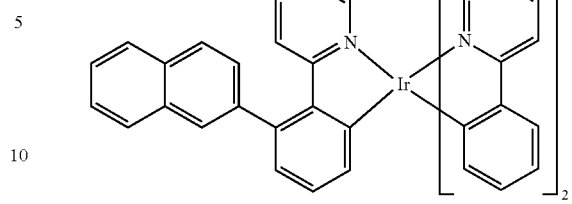

In the yellow-green EML 525, the yellow-green dopant can have a weight % of 3 weight % to 30 weight %. The yellow-green EML 525 can have a thickness of 50 to 400 Å.

When the yellow-green EML 525 includes the first yellow-green host and the second yellow-green host, a weight ratio of the first yellow-green host to the second yellow-green host can be 1:9 to 9:1, preferably 2:8 to 8:2, and more preferably 3:7 to 7:3. For example, the yellow-green EML 525 can have a thickness of 300 Å, the first yellow-green host and the second yellow-green host can have the same weight %, and the yellow-green dopant can be doped by 15 weight %.

The first blue EML 550 in the second emitting part 540 includes a first blue host and a first blue dopant, and the second blue EML 570 in the third emitting part 560 includes a second blue host and a second blue dopant. Each of the first and second blue hosts can be an anthracene derivative, and each of the first and second blue dopants can be a boron derivative.

For example, the first blue host in the first blue EML 550 can be represented by Formula 22-2 or Formula 22-4, and the second blue host in the second blue EML 570 can be represented by Formula 22-3 or Formula 22-5.

Namely, the first blue host in the first blue EML 550 and the second blue host in the second blue EML 570 can be the anthracene derivative having the same structure and can have a difference in a deuteration ratio. In other words, the first blue host in the first blue EML 550 can have a first deuteration ratio, and the second blue host in the second blue EML 570 can have a second deuteration ratio being smaller than the first deuteration ratio.

Each of the first blue dopant in the first blue EML 550 and the second blue dopant in the second blue EML 570 can be represented by Formula 25.

The first blue dopant can have a weight % of 0.1 to 10, e.g., 1 to 5, in the first blue EML 550, and the second blue dopant can have a weight % of 0.1 to 10, e.g., 1 to 5, in the second blue EML 570. For example, the weight % of the first blue dopant in the first blue EML 550 can be equal to or greater than that of the second blue dopant in the second blue EML 570.

Each of the first and second blue EMLs 550 and 570 can have a thickness of 100 Å to 1000 Å, e.g., 100 Å to 500 Å, but it is not limited thereto. For example, the thickness of the first blue EML 550 can be equal to or smaller than that of the second blue EML 570.

For example, the thickness of the first blue EML 550 can be smaller than that of the second blue EML 570, and the weight % of the first blue dopant in the first blue EML 550 can be greater than that of the second blue dopant in the second blue EML 570.

The HIL 542 in the second emitting part 540 can include the hole injection material in Formula 7-1. In addition, the HIL 542 can further include the compound in Formula 9 as a p-type dopant.

Each of the first HTL 532 in the first emitting part 530, the second HTL 544 in the second emitting part 540 and the third HTL 562 in the third emitting part 560 can include the compound in Formula 7-1 as a hole transporting material.

For example, a thickness of the third HTL 562 can be equal to or smaller than that of the second HTL 544 and can be greater than the first HTL 532. The first HTL 532 can have a thickness of about 10 to 150 Å, the second HTL 544 can have a thickness of about 500 to 1000 Å, and the third HTL 562 can have a thickness of about 500 to 900 Å.

Each of the first to third ETL 534, 548 and 566 can include at least one of the benzimidazole-based organic compound in Formula 10 and the azine-based organic compound in Formula 12.

For example, each of the first and third ETL 534 and 566 can include the electron transporting material in Formula 10, and the second ETL 548 can include the electron transporting material in Formula 12. The third ETL 566 can further include the electron transporting material in Formula 12. In the third ETL 566, the electron transporting material in Formula 10 and the electron transporting material in Formula 12 can have the same weight %.

The EIL 568 in the third emitting part 560 can include the compound in Formula 15 as an electron injection material. In addition, the EIL 568 can further include a dopant being at least one of alkali metal, e.g., Li, Na, K or Cs, and alkali earth metal, e.g., Mg, Sr, Ba or Ra.

Each of the first EBL 546 in the second emitting part 540 and the second EBL 564 in the third emitting part 560 can include the electron blocking material in formula 17.

The first CGL 580 is positioned between the first emitting part 530 and the second emitting part 540, and the second CGL 590 is positioned between the first emitting part 530 and the third emitting part 560. Namely, the first and second emitting parts 530 and 540 are connected through the first CGL 580, and the first and third emitting parts 530 and 560 are connected through the second CGL 590. The first CGL 580 can be a P-N junction CGL of an N-type CGL 582 and a P-type CGL 584, and the second CGL 590 can be a P-N junction CGL of an N-type CGL 592 and a P-type CGL 594.

In the first CGL 580, the N-type CGL 582 is positioned between the first HTL 532 and the second ETL 548, and the P-type CGL 584 is positioned between the N-type CGL 582 and the first HTL 532.

In the second CGL 590, the N-type CGL 592 is positioned between the first ETL 534 and the third HTL 562, and the P-type CGL 594 is positioned between the N-type CGL 592 and the third HTL 562.

Each of the N-type CGL 582 in the first CGL 580 and the N-type CGL 592 in the second CGL 590 can include the phenanthroline-based compound of Formula 14 and can include one of the compounds in Formula 15.

Each of the N-type CGL 582 in the first CGL 580 and the N-type CGL 592 in the second CGL 590 can further include a dopant being one of alkali metal, e.g., Li, Na, K or Cs, and alkali earth metal, e.g., Mg, Sr, Ba or Ra. In this instance, the electron generation property and/or the electron injection property of the N-type CGLs 582 and 592 can be improved. In each of the N-type CGLs 582 and 592, the dopant can have a weight % of 0.1 weight % to 10 weight %. In addition, each of the N-type CGLs 582 and 592 can have a thickness of 30 to 500 Å, preferably 50 to 300 Å. For example, the weight % of the dopant in the N-type CGL 582 in the first CGL 580 can be greater than that of the dopant in the N-type CGL 592 in the second CGL 590, and the thickness of the N-type CGL 582 in the first CGL 580 can be smaller than that of the N-type CGL 592 in the second CGL 590.

Each of the P-type CGL 584 in the first CGL 580 and the P-type CGL 594 in the second CGL 590 can include the compound in Formula 7-1. In addition, each of the P-type CGL 584 in the first CGL 580 and the P-type CGL 594 in the second CGL 590 can further include the compound in Formula 9 as a dopant.

In each of the P-type CGL 584 in the first CGL 580 and the P-type CGL 594 in the second CGL 590, the dopant can have a weight % of 1 weight % to 40 weight %, preferably 3 weight % to 30 weight %. Each of the P-type CGL 584 in the first CGL 580 and the P-type CGL 594 in the second CGL 590 can have a thickness of 30 to 500 Å, preferably 50 to 200 Å.

For example, the weight % of the dopant in the P-type CGL 584 of the first CGL 580 can be equal to that of the dopant in the P-type CGL 594 of the second CGL 590, and the thickness of the P-type CGL 584 in the first CGL 580 can be smaller than that of the P-type CGL 594 in the second CGL 590.

As described above, the OLED D of the present disclosure includes the first emitting part 530, which includes the green EML 510, the red EML 520 and the yellow-green EML 525, the second emitting part 540, which includes the first blue EML 550, and the third emitting part 560, which includes the second blue EML 570, so that the white light is provided from the OLED D.

The green EML 510 includes the first host 512 and the second host 514, and at least one of the first and second hosts 512 and 514 is deuterated. Accordingly, the emitting efficiency and the lifespan of the OLED D and the organic light emitting display device 300 are increased.

In addition, when only the fused-hetero ring moiety in the first host 512 is deuterated and/or only the biscarbazole moiety in the second host 514 is deuterated, the lifespan of the OLED D and the organic light emitting display device 300 is further improved.

Moreover, the first blue host of the first blue EML 550 is an anthracene derivative having a first deuteration ratio, and the second blue host of the second blue EML 570 is an anthracene derivative having a second deuteration ratio, which is smaller than the first deuteration ratio. Accordingly, the emitting efficiency and the lifespan of the OLED D and the organic light emitting display device 300 are further increased.

Referring to FIG. 4 again, a second electrode 364 is formed over the first substrate 310 where the organic emitting layer 362 is formed.

In the organic light emitting display device 300, since the light emitted from the organic emitting layer 362 is incident to the color filter layer 380 through the second electrode 364, the second electrode 364 has a thin profile for transmitting the light.

The first electrode 360, the organic emitting layer 362 and the second electrode 364 constitute the OLED D.

The color filter layer 380 is positioned over the OLED D and includes a red color filter 382, a green color filter 384 and a blue color filter 386 respectively corresponding to the red, green and blue pixel regions RP, GP and BP. The red color filter 382 can include at least one of a red dye and a red pigment, the green color filter 384 can include at least one of a green dye and a green pigment, and the blue color filter 386 can include at least one of a blue dye and a blue pigment.

The color filter layer 380 can be attached to the OLED D by using an adhesive layer. Alternatively, the color filter layer 380 can be formed directly on the OLED D.

An encapsulation film can be formed to prevent penetration of moisture into the OLED D. For example, the encapsulation film can include a first inorganic insulating layer, an organic insulating layer and a second inorganic insulating layer sequentially stacked, but it is not limited thereto. The encapsulation film can be omitted.

A polarization plate for reducing an ambient light reflection can be disposed at an outer side of the second substrate 370. For example, the polarization plate can be a circular polarization plate.

In the organic light emitting display device 300 of FIG. 4, the first electrode 360 and the second electrode 364 are a reflective electrode and a transparent (semitransparent) electrode, respectively, and the color filter layer 380 is disposed over the OLED D. Alternatively, the first electrode 360 and the second electrode 364 are a transparent (semitransparent) electrode and a reflective electrode, respectively, and the color filter layer 380 can be disposed between the OLED D and the first substrate 310.

A color conversion layer can be formed between the OLED D and the color filter layer 380. The color conversion layer can include a red color conversion layer, a green color conversion layer and a blue color conversion layer respectively corresponding to the red, green and blue pixel regions RP, GP and BP. The white light from the OLED D is converted into the red light, the green light and the blue light by the red, green and blue color conversion layer, respectively. For example, the color conversion layer can include a quantum dot. The color purity of the organic light emitting display device 300 can be further improved due to the color conversion layer.

Alternatively, the color conversion layer can be included instead of the color filter layer 380.

As described above, the white light from the organic light emitting diode D passes through the red color filter 382, the green color filter 384 and the blue color filter 386 in the red pixel region RP, the green pixel region GP and the blue pixel region BP such that the red light, the green light and the blue light are provided from the red pixel region RP, the green pixel region GP and the blue pixel region BP, respectively.

In FIG. 4, the OLED D emitting the white light is used for a display device. Alternatively, the OLED D can be formed on an entire surface of a substrate without at least one of the driving element and the color filter layer to be used for a lightening device. The display device and the lightening device each including the OLED D of the present disclosure can be referred to as an organic light emitting device.

In the OLED D and the organic light emitting display device 300, the green EML includes the first host, which includes a fused-hetero ring moiety, and the second host, which includes a bis-carbazole moiety, and at least one of the first and second hosts is deuterated. Accordingly, the emitting efficiency and the lifespan of the OLED D and the organic light emitting display device 300 are increased.

In addition, when only the fused-hetero ring moiety in the first host is deuterated and/or only the biscarbazole moiety in the second host is deuterated, the lifespan of the OLED D and the organic light emitting display device 300 is further improved.

It will be apparent to those skilled in the art that various modifications and variations can be made in the embodiments of the present disclosure without departing from the spirit or scope of the present disclosure. Thus, it is intended that the modifications and variations cover this disclosure provided they come within the scope of the appended claims and their equivalents.

What is claimed is:

1. An organic light emitting diode, comprising:

a first electrode;

a second electrode facing the first electrode;

a first emitting part including a green emitting material layer and positioned between the first and second electrodes, the green emitting material layer including a first host, a second host and a dopant;

a second emitting part including a first blue emitting material layer and positioned between the first electrode and the first emitting part;

a first charge generation layer including a P-type charge generation material and positioned between the first emitting part and the second emitting part;

a third emitting part including a second blue emitting material layer and positioned between the first emitting part and the second electrode; and a second charge generation layer positioned between the first emitting part and the third emitting part, wherein the first host is represented by Formula 1-1:

[Formula 1-1]

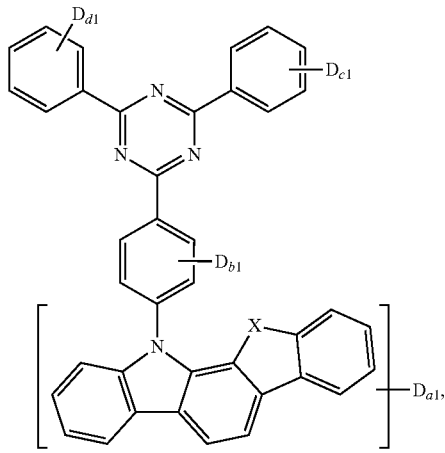

wherein

D denotes a deuterium atom,

X is oxygen or sulfur, a1 is an integer of 0 to 10, wherein b1 is an integer of 0 to 4, and each of c1 and d1 is independently an integer of 0 to 5, wherein the second host is represented by Formula 2-1:

[Formula 2-1]

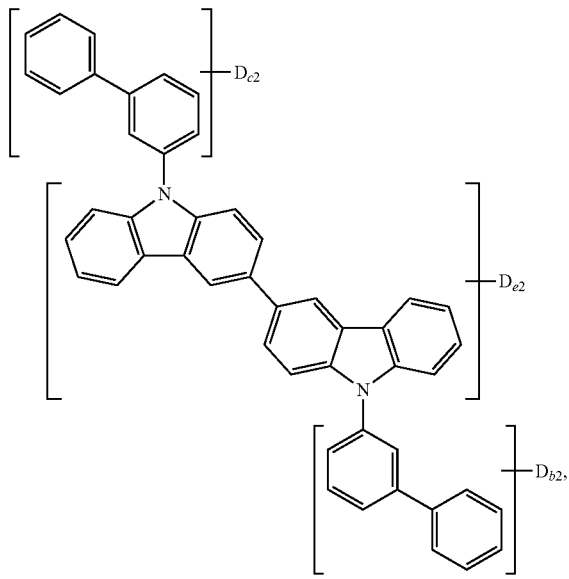

wherein a2 is an integer of 0 to 14, and each of b2 and c2 is independently an integer of 0 to 9, and wherein at least one of a1, a2, b1, b2, c1, c2 and d1 is a positive integer.

2. The organic light emitting diode according to claim 1, wherein a1 is an integer of 1 to 10 and each of b1, c1 and d1 is 0.

3. The organic light emitting diode according to claim 2, wherein the first host is one of following compounds host 1-4 and host 2-4, and the second host is one of compounds in Formula 4:

Host 1-4

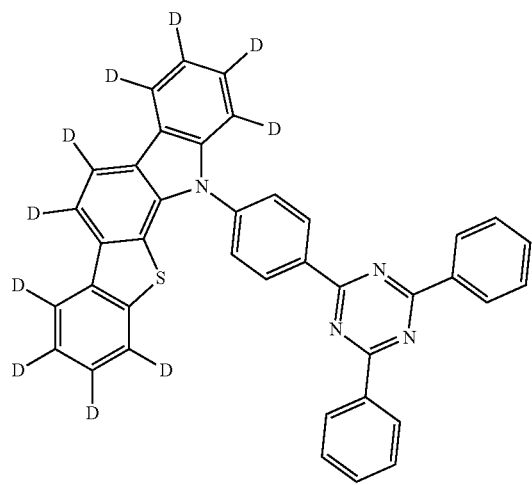

-continued

Host 2-4

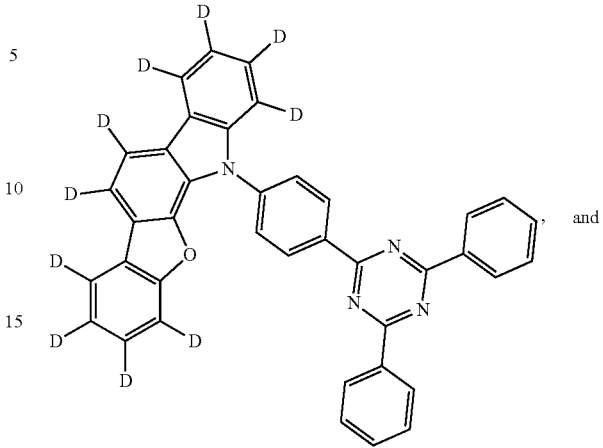

, and

[Formula 4]

Host 3-1

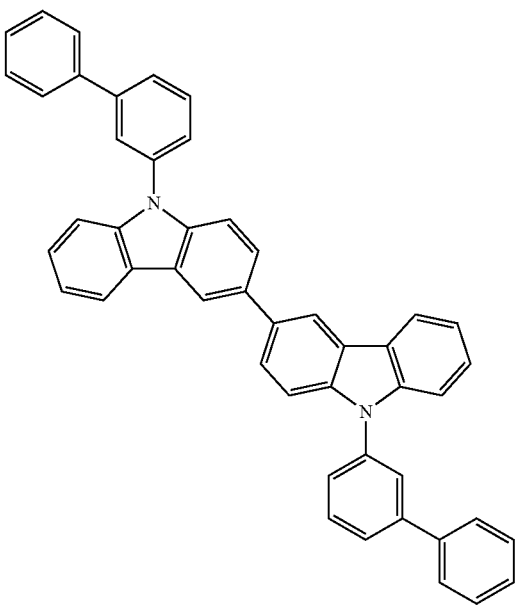

Host 3-2
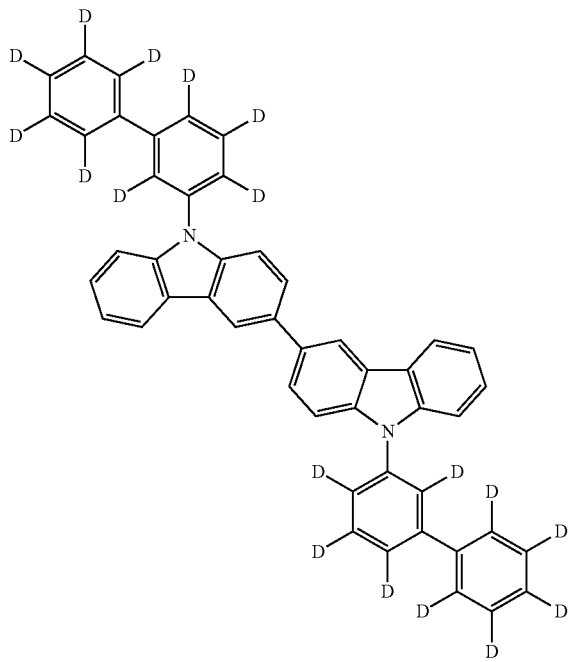
Host 3-3
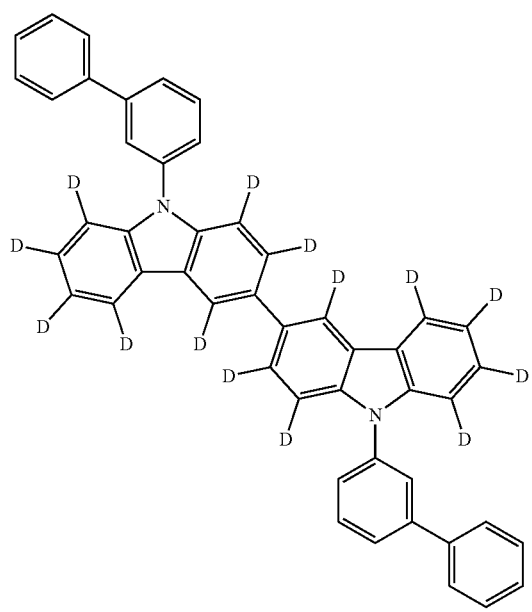
Host 3-4
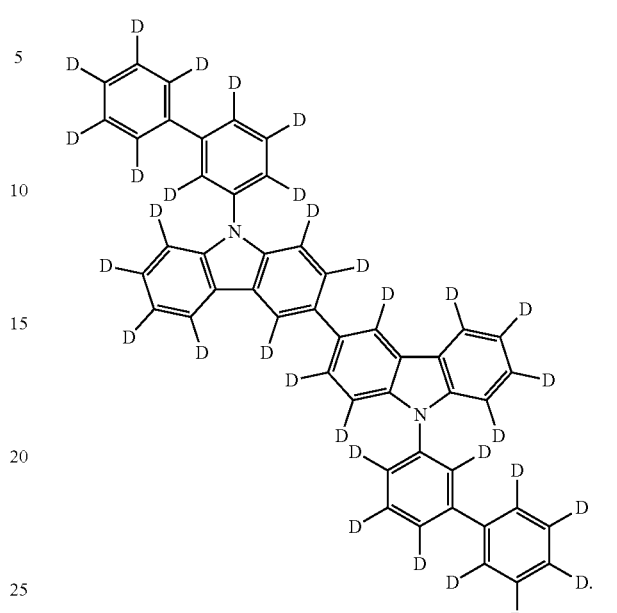
4. The organic light emitting diode according to claim 1, wherein a2 is an integer from 1 to 14, and each of b2 and c2 is 0.
5. The organic light emitting diode according to claim 4, wherein the first host is selected from compounds Host 1-1 to Host 1-5 and Host 2-1 to Host 2-5, and the second host is the following compound host 3-3:
[Formula 3]
Host 1-1
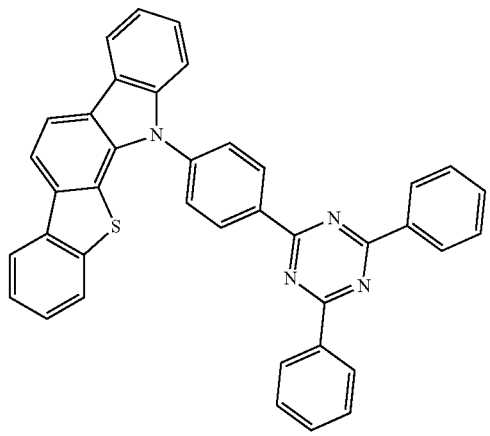

Host 1-2
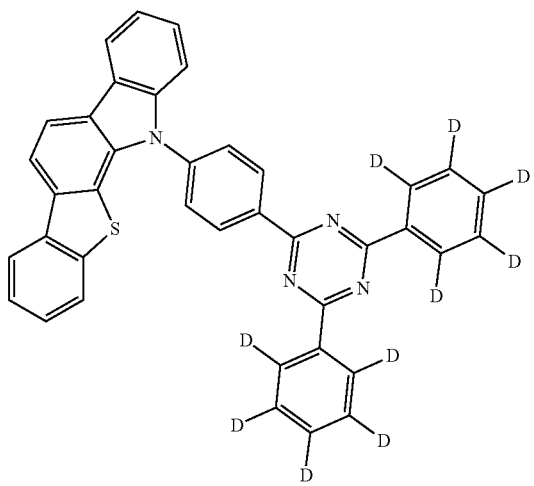
Host 1-5
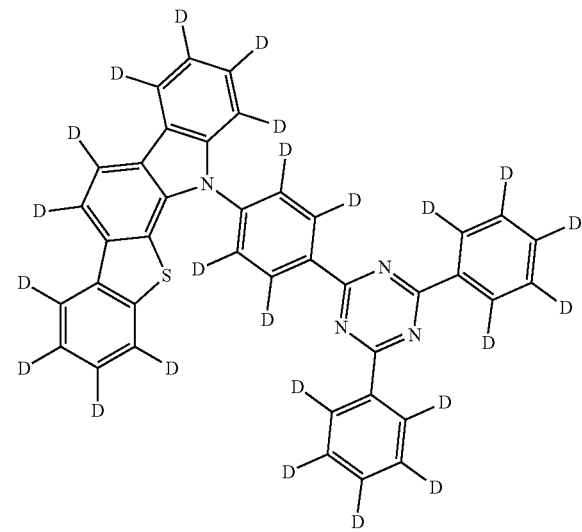
Host 1-3
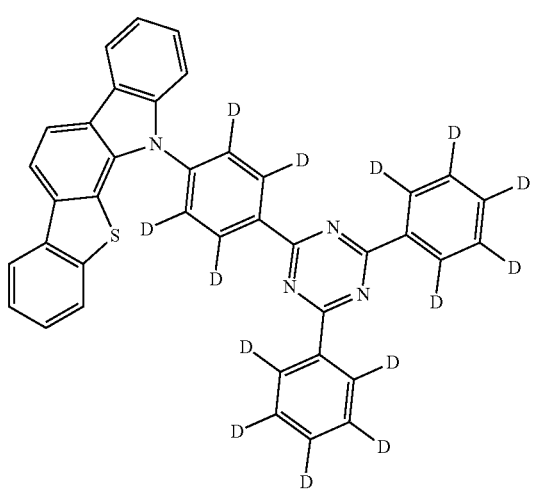
Host 2-1
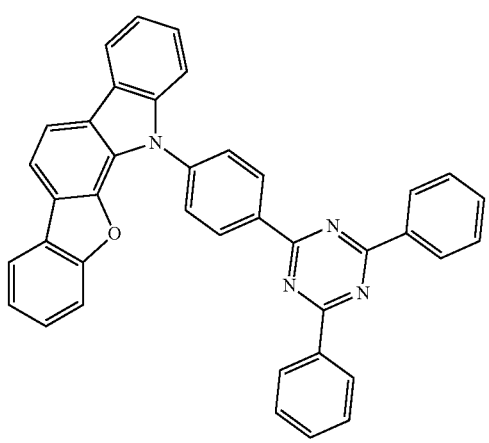
Host 1-4
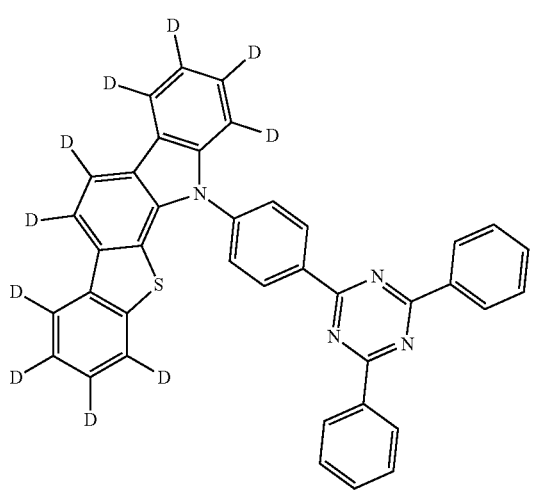
Host 2-2
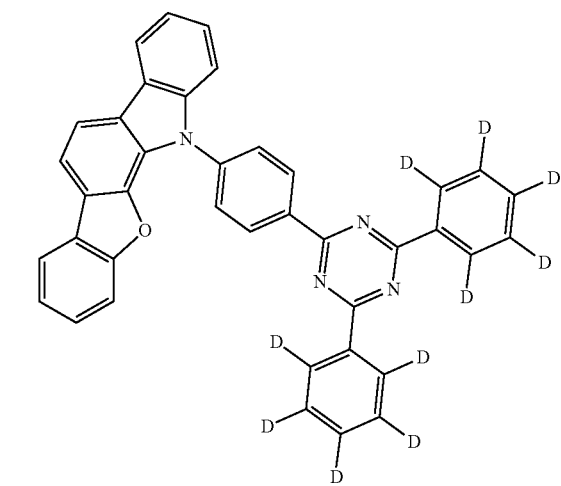

Host 2-3

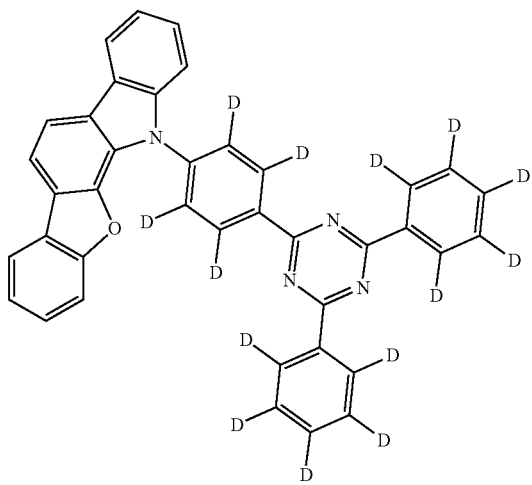

Host 2-4

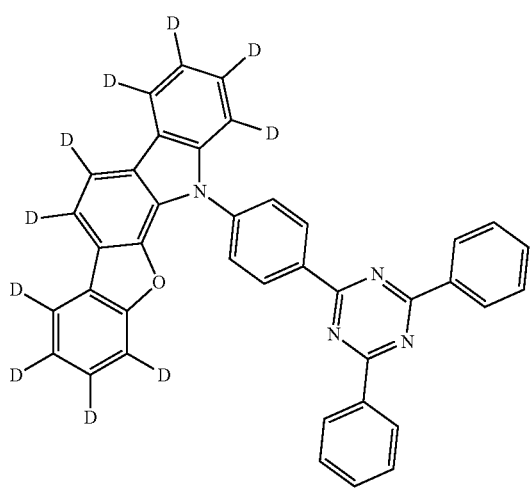

Host 2-5

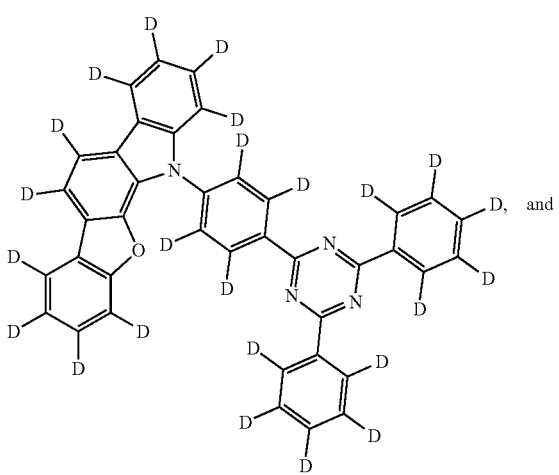, and

Host 3-3

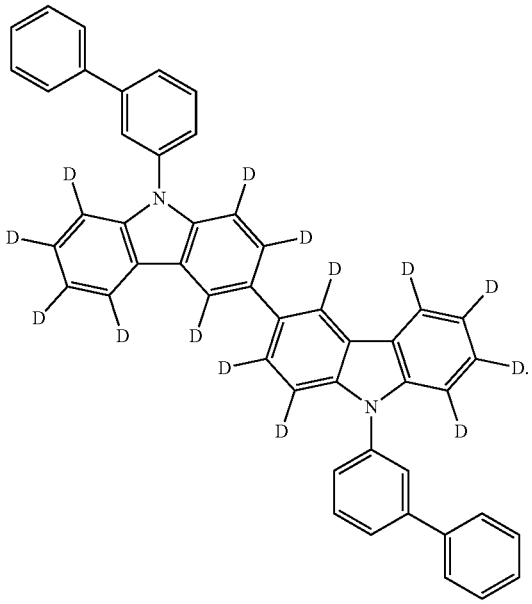

6. The organic light emitting diode according to claim 1, wherein the first blue emitting material layer includes a first blue host of Formula 22-2, and the second blue emitting material layer includes a second blue host of Formula 22-3:

[Formula 22-2]

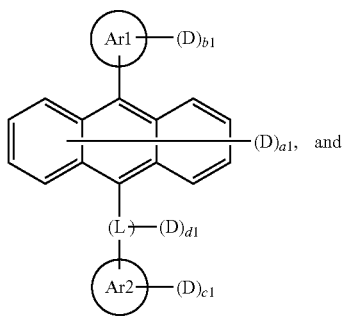, and

[Formula 22-3]

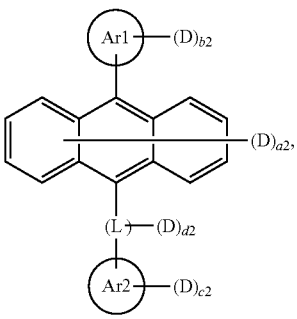

wherein each of Ar1 and Ar2 is independently C6 to C20 aryl group, and

L is C6 to C20 arylene group, wherein each of a1 and a2 is independently an integer of 0 to 8, and each of b1, b2, c1, c2, d1 and d2 is independently an integer of 0 to 20, and wherein a summation of a1, b1, c1 and d1 is greater than a summation of a2, b2, c2 and d2.

7. The organic light emitting diode according to claim 6, wherein the first blue host is represented by Formula 22-4, and the second blue host is represented by Formula 22-5:

[Formula 22-4]

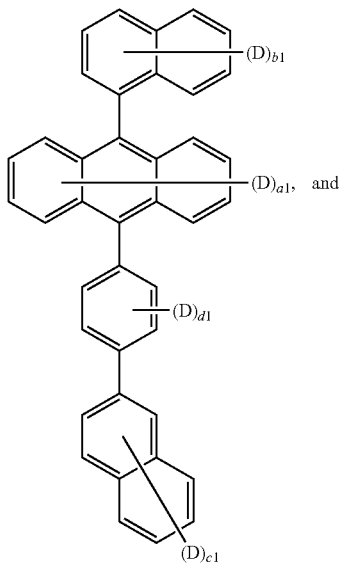

[Formula 22-5]

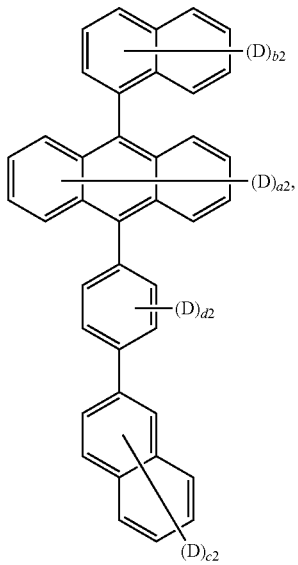

wherein each of a1 and a2 is independently an integer of 0 to 8, each of b1, b2, c1 and c2 is independently an integer of 0 to 7, wherein each of d1 and d2 is independently an integer of 0 to 4, and wherein a summation of a1, b1, c1 and d1 is greater than a summation of a2, b2, c2 and d2.

8. The organic light emitting diode according to claim 7, wherein the first blue host is a compound in Formula 23-1:

[Formula 23-1]

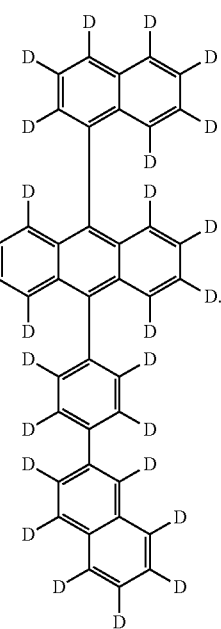

Host 1-5

9. The organic light emitting diode according to claim 7, wherein the second blue host is one of compounds in Formula 23-2:

[Formula 23-2]

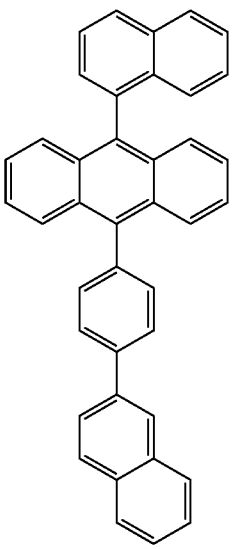

Host 1-1

Host 1-2

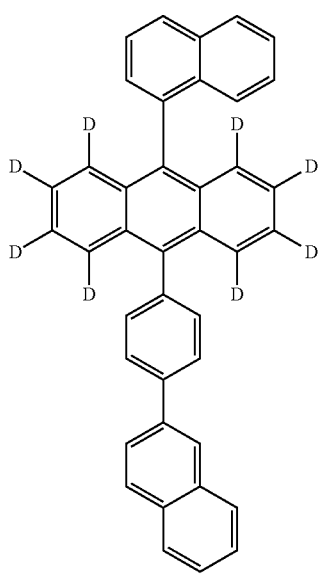

Host 1-3

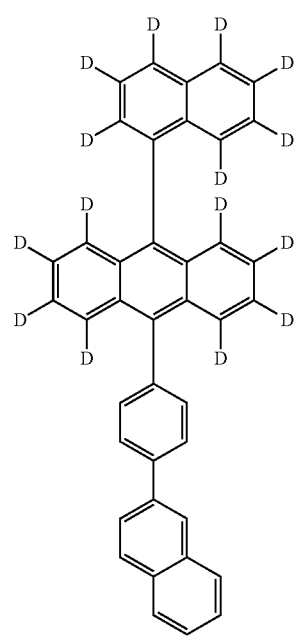

Host 1-4

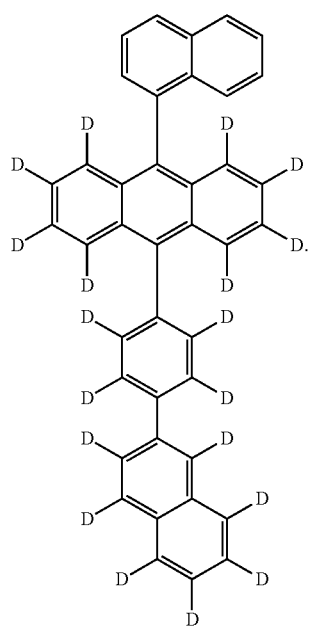

10. The organic light emitting diode according to claim 6, wherein the first blue emitting material layer includes a first blue dopant being a boron derivative, and the second blue emitting material layer includes a second blue dopant being a boron derivative.

11. The organic light emitting diode according to claim 10, wherein each of the first and second blue dopants is represented by Formula 24:

[Formula 24]

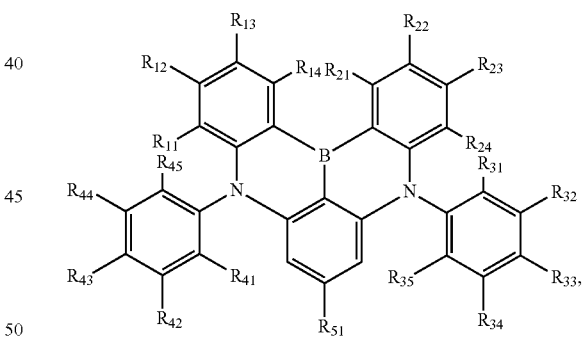

wherein each of $R_{11}$ to $R_{14}$, each of $R_{21}$ to $R_{24}$, each of $R_{31}$ to $R_{35}$ and each of $R_{41}$ to $R_{45}$ is selected from the group of hydrogen, deuterium, C1 to C10 alkyl group, C6 to C30 aryl group unsubstituted or substituted with C1 to C10 alkyl group, C12 to C30 arylamine group and C5 to C30 heteroaryl group, or adjacent two of $R_{11}$ to $R_{14}$, adjacent two of $R_{21}$ to $R_{24}$, adjacent two of $R_{31}$ to $R_{35}$ and adjacent two of $R_{41}$ to $R_{45}$ are connected to each other to form a fused ring unsubstituted or substituted with C1 to C10 alkyl group, and wherein $R_{51}$ is selected from the group consisting of hydrogen, deuterium, C1 to C10 alkyl group and C3 to C30 cycloalkyl group, C6 to C30 aryl group, C5 to C30 heteroaryl group and C6 to C30 arylamine group unsubstituted or substituted with C1 to C10 alkyl group.

12. The organic light emitting diode according to claim 11, wherein each of the first and second blue dopants is independently selected from compounds in Formula 25:
[Formula 25]
Dopant 1
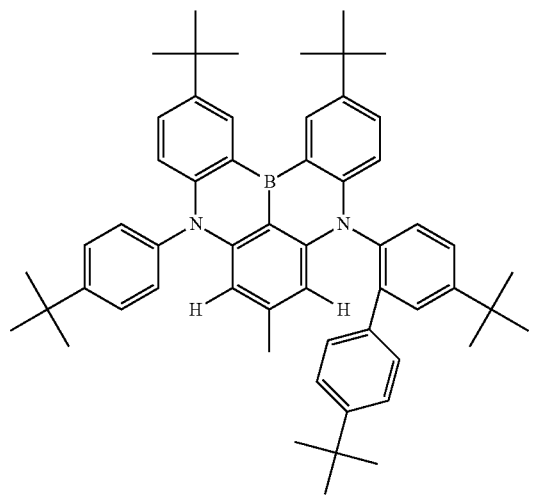
Dopant 2
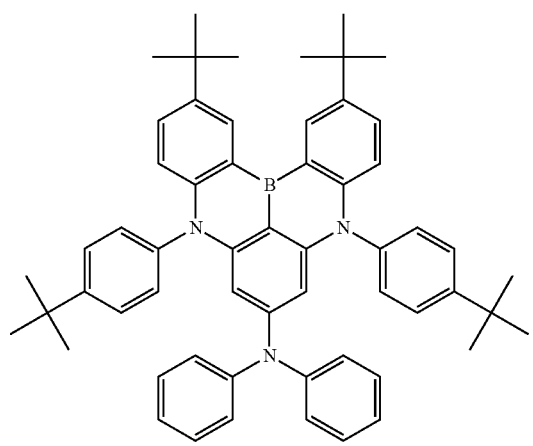
Dopant 3
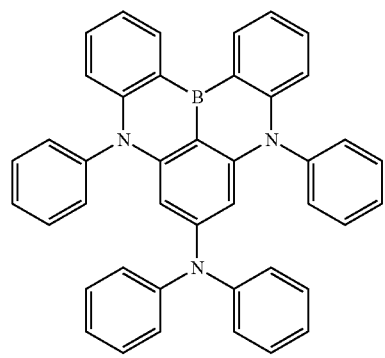
-continued
Dopant 4
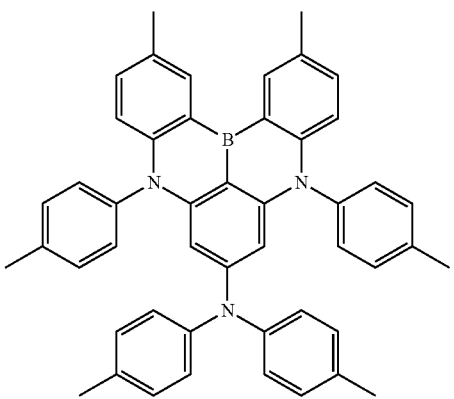
Dopant 5
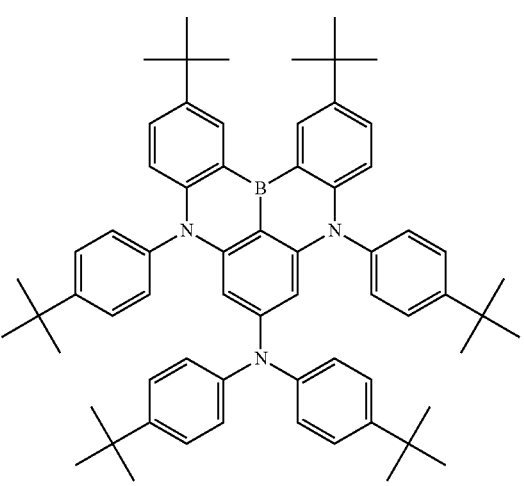
Dopant 6
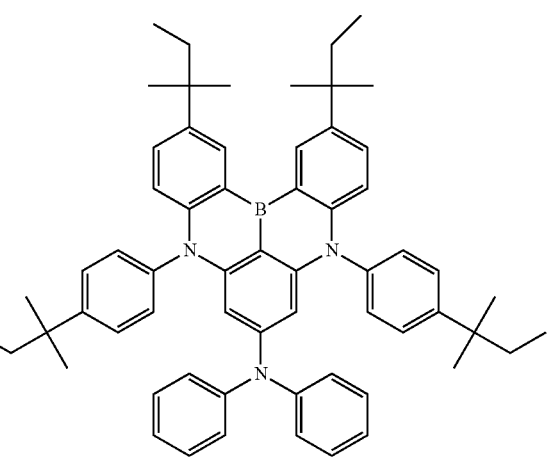

Dopant 7
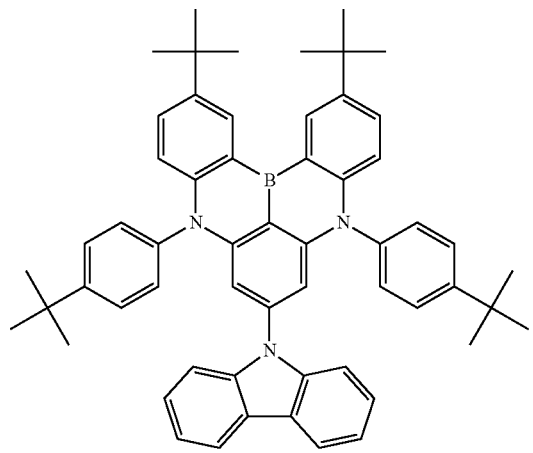
Dopant 8
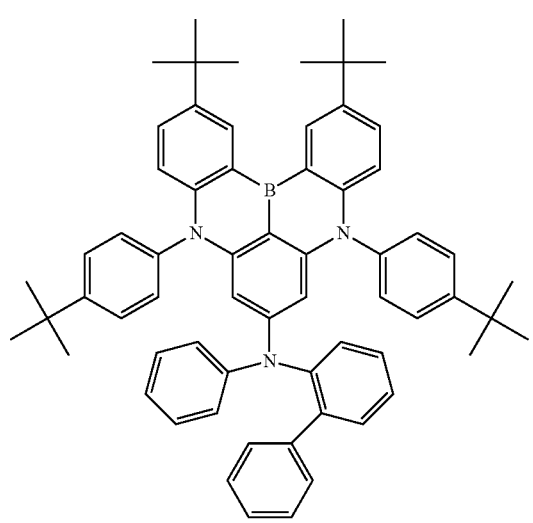
Dopant 9
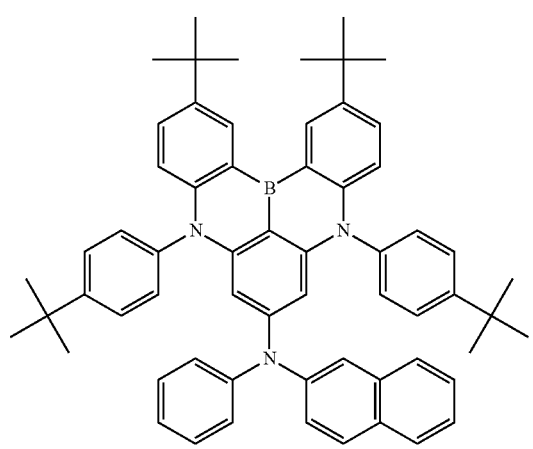
Dopant 10
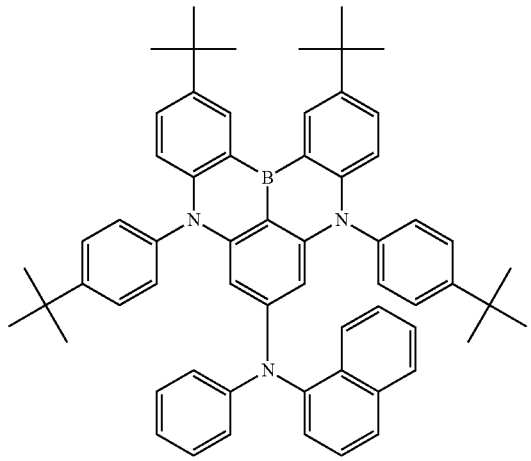
Dopant 11
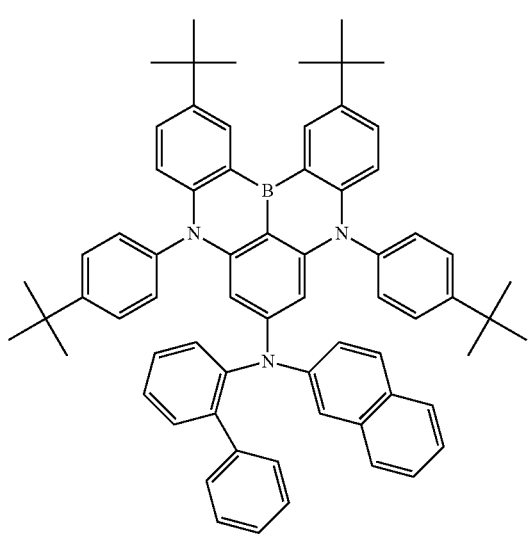
Dopant 12
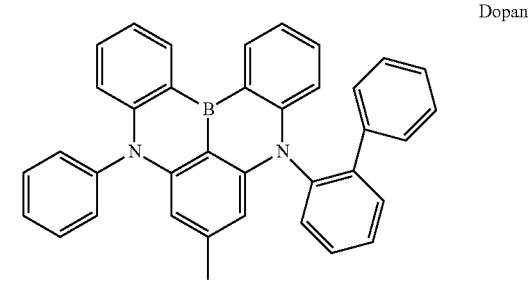
Dopant 13
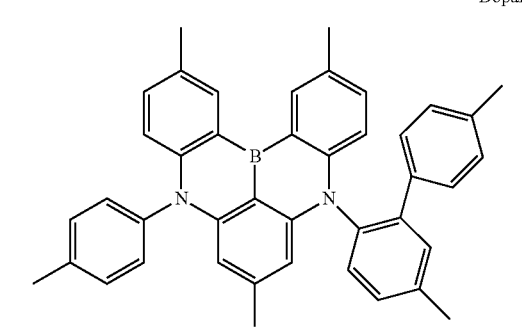

Dopant 14
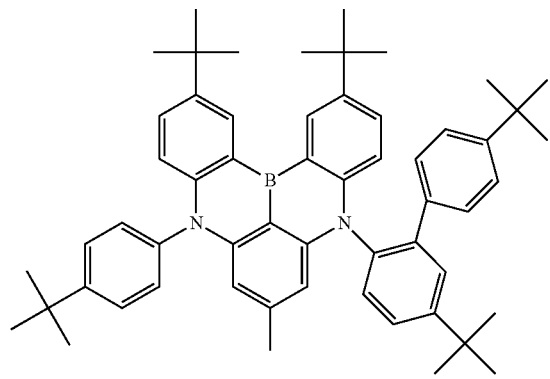

Dopant 15
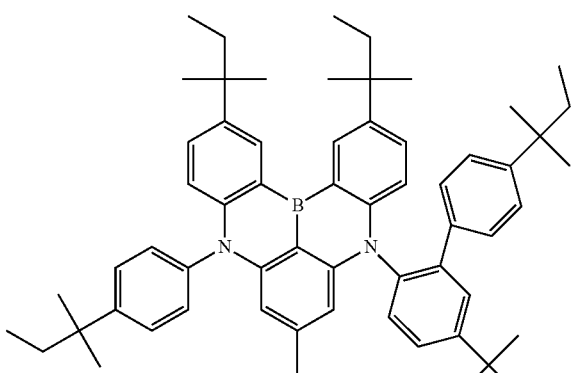

Dopant 16
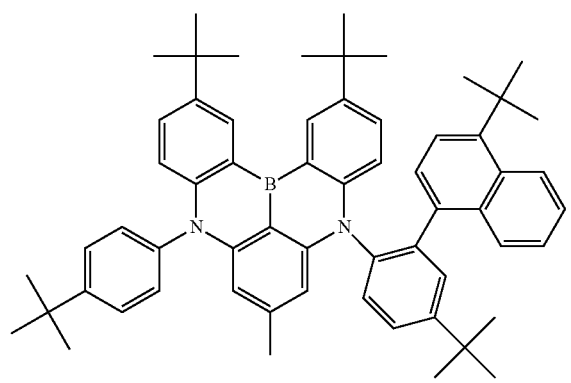

Dopant 17
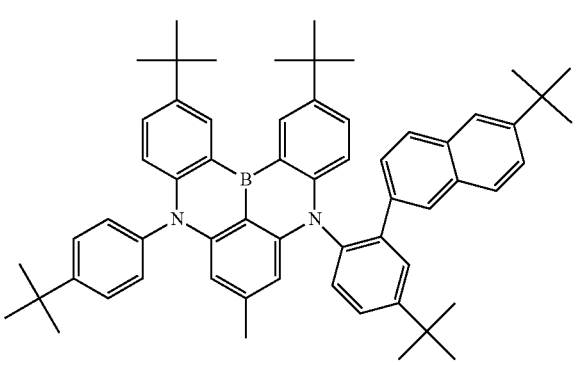

Dopant 18
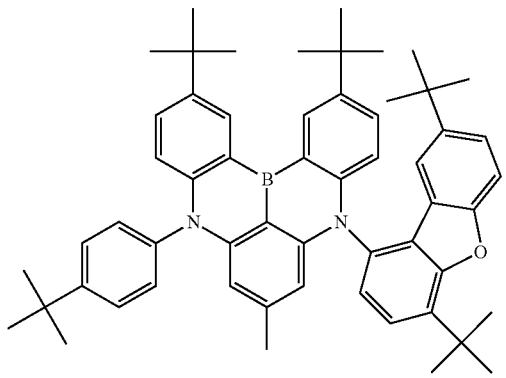

Dopant 19
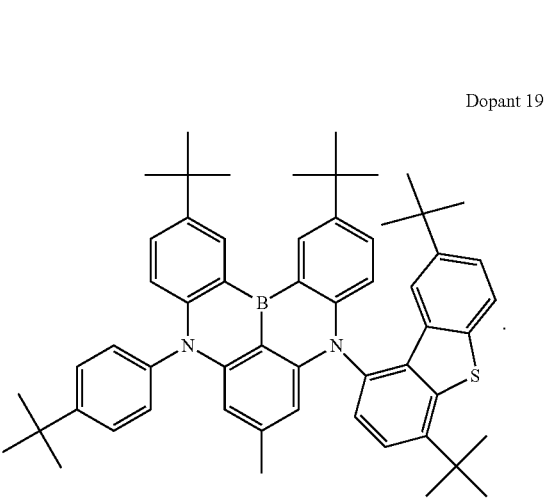

13. The organic light emitting diode according to claim 11, wherein a weight % of the first blue dopant in the first blue emitting material layer is equal to or greater than a weight % of the second blue dopant in the second blue emitting material layer.

14. The organic light emitting diode according to claim 13, wherein a thickness of the first blue emitting material layer is equal to or smaller than a thickness of the second blue emitting material layer.

15. The organic light emitting diode according to claim 1, wherein the first emitting part further includes a red emitting material layer between the green emitting material layer and the first charge generation layer.

16. The organic light emitting diode according to claim 15, wherein the first emitting part further includes a yellow-green emitting material layer between the red and green emitting material layers.

17. An organic light emitting device, comprising:
a substrate; and
an organic light emitting diode positioned on the substrate and including a first electrode, a second electrode facing the first electrode, a first emitting part including a green emitting material layer and positioned between the first and second electrodes, a second emitting part including a first blue emitting material layer and positioned between the first electrode and the first emitting part, a first charge generation layer including a P-type charge generation material and positioned between the first emitting part and the second emitting part, a third emitting part including a second blue emitting material layer and positioned between the first emitting part and the second electrode, and a second charge generation layer positioned between the first emitting part and the third emitting part, the green emitting material layer including a first host, a second host and a dopant, wherein the first host is represented by Formula 1-1:

[Formula 1-1]

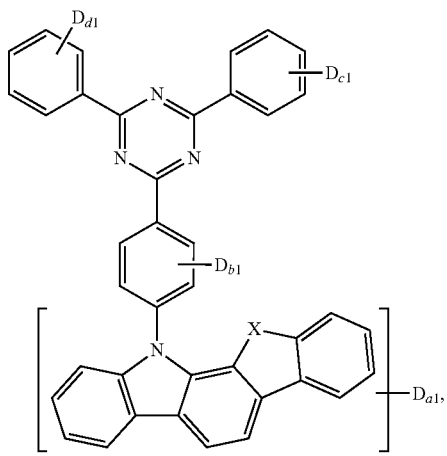

wherein X is oxygen or sulfur, a1 is an integer of 0 to 10, wherein b1 is an integer of 0 to 4, and each of c1 and d1 is independently an integer of 0 to 5, wherein the second host is represented by Formula 2-1:

[Formula 2-1]

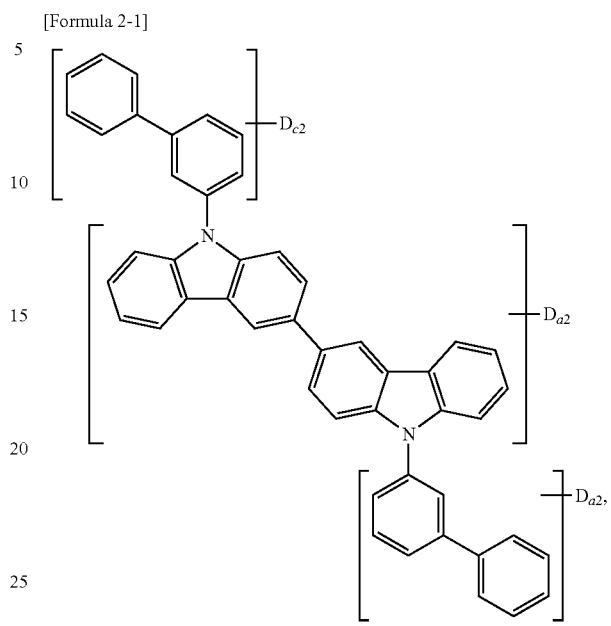

wherein a2 is an integer of 0 to 14, and each of b2 and c2 is independently an integer of 0 to 9, and wherein at least one of a1, a2, b1, b2, c1, c2 and d1 is a positive integer.

18. The organic light emitting device according to claim 17, wherein a1 is an integer from 1 to 10 and each of b1, c1 and d1 is 0.

19. The organic light emitting device according to claim 17, wherein a2 is an integer from 1 to 14, and each of b2 and c2 is 0.

* * * * *